United States Patent [19]

Smith et al.

[11] Patent Number: 5,610,011
[45] Date of Patent: Mar. 11, 1997

[54] VIRULENCE-ENCODING DNA SEQUENCES OF *STREPOCOCCUS SUIS* AND RELATED PRODUCTS AND METHODS

[75] Inventors: Hilda E. Smith, Cz Lelystad; Uri Vecht, As Ermelo, both of Netherlands

[73] Assignee: Centraal Diergeneeskundig Instituut, PH Lelystad, Netherlands

[21] Appl. No.: 119,125

[22] PCT Filed: Mar. 19, 1992

[86] PCT No.: PCT/NL92/00054

§ 371 Date: Sep. 20, 1993

§ 102(e) Date: Sep. 20, 1993

[87] PCT Pub. No.: WO92/16630

PCT Pub. Date: Jan. 10, 1992

[30] Foreign Application Priority Data

Mar. 21, 1991 [NL] Netherlands ............... 9100510

[51] Int. Cl.$^6$ ............... C12Q 1/68; C07H 21/04
[52] U.S. Cl. ............. 435/6; 435/252.3; 435/320.1; 435/885; 435/975; 536/23.1; 536/23.7; 536/24.32; 935/9
[58] Field of Search ................ 435/6, 885, 252.3, 435/320.1, 975; 514/44; 536/23.1, 23.7, 24.32; 424/234.1; 935/9

[56] References Cited

FOREIGN PATENT DOCUMENTS 0383509  8/1990  European Pat. Off. .
WO85/00832  2/1985  WIPO .

OTHER PUBLICATIONS

PL Felgner et al (1991) Science 349:351–352.
Watson et al (1987) Molecular Biology of the Gene 4th ed., p. 313.
Am. J. Vet. Res., vol. 50, No. 7, Jul. 1989, U. Vecht et al., pp. 1037–1043.
Abstracts of Papers, part I, 200th ACS National Meeting, Washington DC, 26–31 Aug. 1990, American Chemical Society, J. R. Lowe et al abstract No. 158.
Biological Abstracts, vol. 89, 1990, (Philadelphia, PA, US), G.
Frankel et al. p. 635, abstract No. 72068, Mol. Microbiol. 3(12): 1729–1734. 1989, see abstract.
Disserattion Abstracts Int'l B, vol. 52, No. 1, Jul. 1991, J. D. Mogollon Galvis: p. 102, see abstract.
Infection and Immunity, vol. 59, No. 9, Sep. 1991, U. Vecht et al.: pp. 3156–3162.

*Primary Examiner*—Bruce R. Campell
*Attorney, Agent, or Firm*—Handal & Morofsky

[57] ABSTRACT

The invention provides DNA sequences which code for polypeptides which are characteristic for the virulence of the pathogenic bacterium *Streptococcus suis* and parts thereof, and polypeptides and antibodies derived therefrom. The sequences code for a polypeptide of 90,000–120,000 daltons or a polypeptide of higher molecular weight containing such a polypeptide, and for a polypeptide of 135,000–136,000 daltons (muramidase released protein), or parts thereof. The sequences themselves, and also the polypeptides and antibodies derived therefrom, are used for diagnosis of and protection against infection by *S. suis* in mammals, including man.

9 Claims, 13 Drawing Sheets

Fig. 4A

```
3415 - A A G G T G G C G A C A G A C G C T A T T G A T   left
4447 - C C A A A C T T G A C A G A C G C A G A G A A G   right
     - A A G G T G G C G A C A G A C G C A G A G A A G   junction
```

Fig. 4B

```
2848 - G C T A T T A A C C A G G C G A A G G A A A A A   left
5216 - C A A C A A G T C C A G T C G A A G C G C A A T   right
     - G C T A T T A A C C A G T C G A A G C G C A A T   junction
``` pMR7-1
pMR7-2
pMR9-1
pMR9-2
pMR10-1
pMR10-2

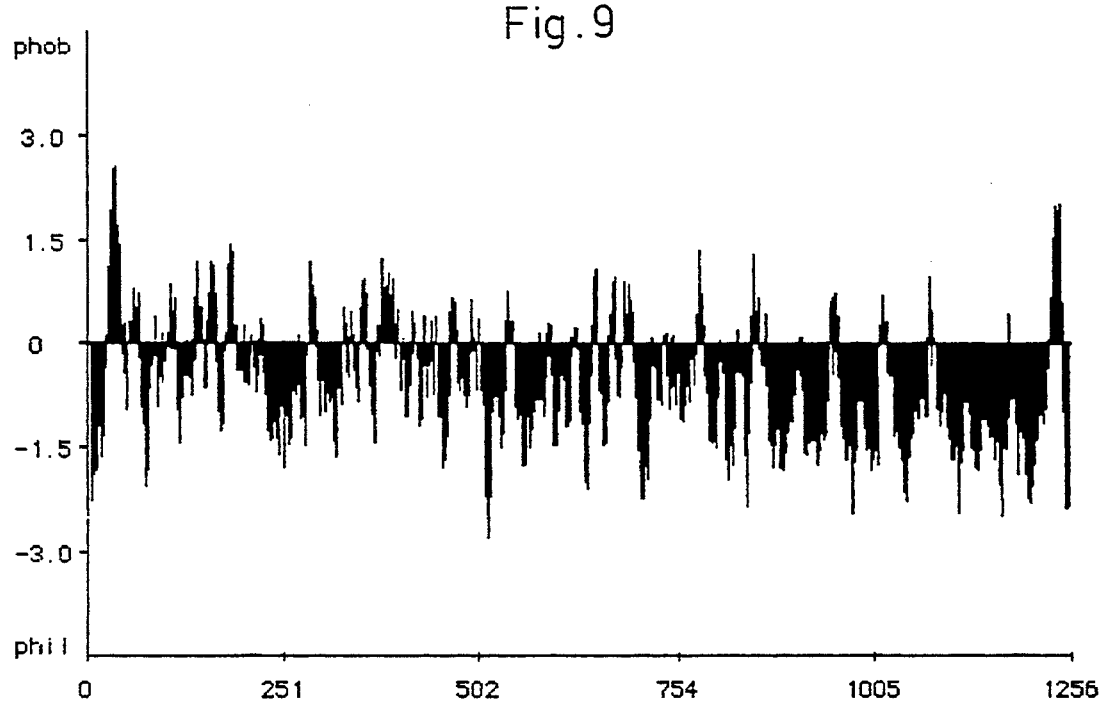

VIRULENCE-ENCODING DNA SEQUENCES OF *STREPOCOCCUS SUIS* AND RELATED PRODUCTS AND METHODS

FIELD OF THE INVENTION

The invention is in the field of veterinary and human preventive medicine, in particular that of the diagnosis of and protection against infection by pathogenic strains of the bacterium *Streptococcus suis*.

Infections with *Streptococcus suis* serotype 2 in young pigs at about the time of weaning have been a growing problem in the Netherlands since 1983. The disease is characterised by meningitis, arthritis, sepsis and death (Clifton-Hadley 1983, ref. 6; Vecht et al. 1985, ref. 44; Windsor 1977, ref. 50). It is estimated that 5–10 per cent of farms have problems of this type. The mortality is estimated at 2.5% and the morbidity in affected farms is on average 2–5%. Therapeutic and preventive measures have only a limited effect. The economic damage is accordingly appreciable. The disease is a zoonosis. Humans are also susceptible to this infection, with the risk of sepsis and meningitis with possibly permanent side-effects; rare cases of death have been reported (Arends and Zanen 1988, ref. 2). This related mostly to cases of people with a skin wound coming into contact with infected pork. In particular, pig farmers and slaughterhouse staff belong to the risk group.

There are indications that the increased rate of illness on pig farms in the Netherlands since 1983 is to be ascribed to the import of breeding animals which are carriers of *S. suis* type 2. Carriers are often healthy adult pigs which harbour the streptococci in the tonsils and mucosa of the upper respiratory tract. The infection is transmitted via these carriers to susceptible animals, frequently piglets at weaning age. Diagnosis of animals which are already sick or have died is based on isolation and determination of *S. suis* type 2 from clinical samples or organs after necropsy. Detection of carriers is based on bacteriological examination of nose or throat swabs or tonsil biopsies using a selective/elective medium (Van Leengoed et al. 1987, ref. 27). On the basis of diagnostic testing to detect carriers, it should be possible to set up a control programme. However, testing for carriers using the conventional becteriological techniques is time-consuming, which complicates the processing of large numbers of samples; there is also a risk of false negative results due to overgrowth with contaminants. Finally, interpretation of the test demands a great deal of experience. Moreover, diagnosis and possible control on the basis of diagnosis are further complicated by the occurrence of differences in pathogenicity within the *S. suis* type 2 species. Regular testing for carriers within a control programme is sensible only if truly virulent strains of *S. suis* type 2 can be differentiated from avirulent strains. Current diagnostic techniques do not make such discrimination. Consequently, control based on the detection of carriers of virulent *S. suis* type 2 strains is not yet possible.

Differences in virulence are ascribed, inter alia, to the presence or absence of virulence factors. In 1984, Arends and Zanen (ref. 1) described "lysozyme-positive proteins" in human strains. In a study with experimental animals it was found that a "lysozyme-positive" strain (D-282) was pathogenic for gnotobiotic pigs, in contrast to a "lysozyme-negative" strain (T-15) (Vecht et al. 1989, ref. 43). The "lysozyme-positive protein " is probably identical to the muramidase-released protein (MRP) of strain D-282.

The pig industry in the Netherlands and many other countries has a pyramid structure, with a small number of breeding herds at the top, from where animals are distributed to replication herds. These supply a large number of fattening herds, supplying animal products to slaughterhouses. A control program based on diagnosis (certification of farms, elimination of positive carriers, import requirements) should primarily aim at creating herds which are free of *S. suis* type 2 high in this pyramid. A vaccine would primarily be useful in affecting herds lower in the pyramid. Furthermore, means and methods for diagnosing infections by *Streptococcus suis* in human medicine can be of value.

SUMMARY OF THE INVENTION

The object of the invention is to provide methods and means which make it possible, in a more effective manner than hitherto, to detect infections by *Streptococcus suis* on the one hand and to prevent such infections by elimination of infected pigs and carrier pigs on the other hand.

This object is achieved by using a DNA sequence from the gene which codes for a virulence characteristic of *S. suis*. In this context, a virulence characteristic is defined as a polypeptide whose presence is associated with the virulence of an organism, in this case the bacterium *S. suis*, in particular serotype 2.

Two genes of virulent strains of *S. suis* type 2 have been found which code for two proteins, which are designated MRP (muramidase released protein) and EF (extracellular factor) and which appear to be characteristic for virulence (virulence factors). MRP and EF are high molecular weight proteins. MRP (136kd) is a protein associated with the cell envelope and can be released from the cell wall by muramidase. EF (110kD) is an extracellular product which is secreted by the bacterium into the growth medium. EF has higher molecular weight counterparts which are denoted herein as EF*.

The invention provides new diagnostic methods which are able to differentiate between virulent and avirulent strains. These methods are based on the genes encoding MRP, EF and EF* and their expression products. On the basis of the expression of one or both proteins by said genes, three different phenotypes of *S. suis* type 2 have been found to date: i.e. the MRP+ EF+ phenotype, the MRP+ EF− phenotype and the MRP− EF− phenotype. 77% (N=111) of strains isolated from organs of pigs showing clinical symptoms of disease were found to possess the MRP+ EF+phenotype, while 86% (n=42) of isolates from tonsils of non-suspect normal slaughter pigs were found to possess the MRP− EF− phenotype. The MRP+ EF− phenotype was most frequently found (74%) (n=27) in isolates from human patients with infections of *S. suis* type 2 (see FIG. 10). Hence infected animals and carriers of virulent strains can be detected, and a vaccine based on MRP, EF and/or EF* can be developed. Using the diagnostic methods for detecting carriers and infected pig herds and/or using vaccines based on MRP, EF and/or EF* , a program for controlling infection by *S. suis* type 2 in pig herds can be developed.

The invention therefore also relates to the DNA sequence of the gene which, apart from coding for specific high molecular weight polypeptides, codes for the 90–120 kDa polypeptide which is a characteristic of *S. suis* virulence, which gene, hereinafter designated the ef gene has the nucleotide sequence according to SEQ ID No: 1 for *S. suis* serotype D-282, and to equivalent sequences and to parts of said sequences. The nucleotide sequence of the entire region coding for EF and the flanking sequences have been determined. Analysis of the sequence of the ef gene SEQ ID NO: 1 provides an open reading frame of 2529 nucleotides which codes for a polypeptide of 843 amino acids (calculated molecular weight 90,014). Monoclonal antibodies generated against the 110 kDa EF protein recognised proteins with a higher molecular weight in culture supernatants of all 38 strains with a MRP+EF– phenotype. This indicates that certain of the 110 kDA EF and the high molecular weight proteins are identical. None of the 91 strains with a MRP+ EF+ phenotype was found to produce these high molecular weight proteins. At the same time, DNA probes based on the gene which codes for the 110 kDa EF were found to hybridise with genes which code for the high molecular weight proteins of MRP+ EF– strains. This indicates that the 110 kDa EF and the high molecular weight proteins are related, which implies that at least part of the ef gene, from strains with a MRP+ EF– phenotype, is identical to the ef gene of strains with the MRP+ EF+ phenotype. The higher molecular weight counterpart of the protein EF is designated herein as EF*, and the gene encoding it as the ef* gene. The corresponding nucleotide and amino acid sequences are represented in SEQ ID NO: 2

The invention also relates to the DNA sequence of the gene which codes for the 135–136 kDa polypeptide which is also a virulence characteristic of *S. suis*, which gene, hereinafter designated the mrp gene, has the nucleotide sequence according to SEQ ID NO: 3 for *S. suis* serotype 2 strain D-282, and to equivalent sequences and to parts of said sequences. The nucleotide sequence of the entire region coding for MRP and the flanking sequences have been determined. Analysis of the sequence and the flanking sequences have been determined. Analysis of the sequence of the mrp gene SEQ ID NO: 3 shows an open reading frame of 3768 nucleotides which codes for a polypeptide of 1256 amino acids (calculated molecular weight 135,794).

In this context, an equivalent sequence comprises a sequence which is essentially the same as the sequence shown but can display slight differences, such as point mutations, or other modifications which may be caused by substitution, deletion, insertion or additional. Similarly, an equivalent sequence also comprises a sequence which, despite any differences in nucleotide sequence, hybridises with the sequence shown or with its complement, and also comprises a related sequence which means that it codes for the same amino acid sequence despite differences in nucleotide sequence.

The invention also relates to a recombinant polynucleotide which contains an ef/ef* gene and/or mrp gene sequence as described above, in the presence of a regulating sequence. A recombinant of this type, such as a virus vector, a plasmid or a bacterium, can be used for expression of the gene or of relevant parts thereof in a desired environment, for example for the production of immunogenic peptides intended for the diagnosis of an infection, or for controlling infection with virulent strains of *S. suis* by vaccination.

Polynucleotide probes which contain a sequence as described above, derived from a gene which codes for a virulence characteristic of *S. suis*, also form part of the invention. A probe of this type in particular corresponds with part of the nucleotide sequence of one of the two said genes. The probe can be used for direct detection of the presence of sequences of virulent strains of *S. suis*. The probe can also be used as a basis for a primer for the multiplication of polynucleotides (for example in a polymerase chain reaction) as part of a diagnostic method or a protection method.

A suitable polynucleotide probe was found to be a partial sequence containing at least 10 nucleotides, preferably at least 15 nucleotides, up to 835 nucleotides from the sequence 1100–1934 of the mrp gene. Another suitable polynucleotide probe was found to be a partial sequence containing 10–417, in particular 15–417 nucleotides from the sequence 2890–3306 of the ef* gene. These probes differentiate effectively between pathogenic and non-pathogenic strains of *S. suis*. A combination of such an mrp based probe and an ef* based probe is an especially powerful diagnostic tool.

The invention also relates to polypeptides which are derived from a polynucleotide sequence described above. A polypeptide of this type is either coded by said sequence or obtained by expression of said sequence and essentially corresponds to a *S. suis* protein characteristic of virulence, or to a part thereof. A polypeptide of this type can, for example, be used as an antigen in an immunoassay, as an immunogen in the immunisation of mammals or as an immunogen for the production of antibodies for diagnostic purposes. The antibodies generated in this way also form part of the invention. Such antibodies can be polyclonal or monoclonal and can be conjugated with a marker (enzyme, isotope, luminescent substance or complex-forming agent); the antibody can also be bound to solid carriers or substrates.

The invention also relates to methods for the detection of an infection by a pathogenic strain or by a non-pathogenic strain of *S. suis*, in which one or more polynucleotide probes, polypeptides and/or antibodies as described above are used. "Infection" signifies here the presence of the pathogenic organism, both in the case where there are clinical signs of disease (infection in a narrow sense) and in the case where there are no clinical signs of disease (infection in a broad sense, of contamination). For immunoassays, such as a determination of the presence of antigens of and/or antibodies against *S. suis* in a sample or in clinical material, it is possible, for example, to use on a microtiter plate a polypeptide (110 kDa) which is encoded by the ef/ef* gene or a part thereof, and/or an antibody which has been generated against such a polypeptide. In addition, it is also possible to use a polypeptide (136 kDa) encoded by the mrp gene or a part thereof, and/or an antibody which has been generated against such a polypeptide. The diagnostic methods can be carried out using procedures known per se. Examples are Enzyme-Linked Immunosorbent Assays (ELISA) and Double Antibody Sandwich (DAS)-ELISA.

The methods described above can be carried out with the aid of diagnostic kits. A diagnostic kit according to the invention contains, respectively, at least one polynucleotide or a polypeptide which corresponds to or is derived from a sequence of the ef/ef* gene or mrp gene or a part thereof or contains an antibody which has been generated against the polypeptide derived from one of the said ef/ef* and mrp sequences. It is also possible to use combinations of probes and the like, in particular of ef* diagnostic agents and mrp diagnostic agents, or combinations of primers, for example for carrying out PCR. The kits can also contain the components required for carrying out diagnoses, such as reagents (labelling substances, dyes and the like), supports (filters, plates and the like), media and calibrating agents as well as a manual for carrying out the diagnosis.

The invention also relates to a method for protecting mammals against infection by *Streptococcus suis*, in which method a polynucleotide, a polypeptide or an antibody as described above is used. When an antibody is used, the method is a passive immunisation, that is to say there is direct provision of antibodies against the pathogenic organism; since antibodies which are derived from EF, EF* and MRP are directed against the most virulent forms of *S. suis*, a procedure of this type can be an effective method for protecting against, or controlling, infection, especially if the animal to be protected is not itself able to produce sufficient antibodies, for example if infection has already taken place or in the case of young animals.

Another form of passive immunisation in the case of pigs is the administration of antibodies to the piglets via the colostrum from the sow. In this case the dam is actively immunised with one or both polypeptides during pregnancy, that is to say before the birth of the piglets. When a polypeptide or a polynucleotide (optionally in the form of a recombinant organism) is used, the procedure is an active immunisation, the animal to be protected being stimulated, by means of the immunogenic polypeptide which is administered directly or in the form of a gene for expression, to produce antibodies.

Another suitable method of immunisation is the administration of a polypeptide from which the activity responsible for virulence has been neutralised. Such a polypeptide should then no longer be pathogenic, while immunogenic characteristics are retained. It can be obtained, for example, by expression of a gene which has been modified with respect to the original ef/ef* or mrp gene, such as by means of deletion.

Vaccines for protecting mammals against an infection by *S. suis*, which vaccines contain a polynucleotide, a polypeptide or an antibody as described above, also form part of the invention.

A particular vaccine according to the invention is a vaccine which contains a *S. suis* material which does not or does not completely bring to expression at least one of the polypeptides corresponding to EF and MRP. This material can originate from or can be formed by a possible live strain which is not virulent or is less virulent.

The role of virulence factors which are involved in the pathogenesis of *S. suis* type 2 has been studied in vivo by means of gnotobiotic/germ-free piglets with *S. suis* type 2 strains defined in respect of virulence factors (MRP and EF). The animal experiments were monitored by means of haematological, bacteriological and (histo)pathological analytical techniques.

BRIEF DESCRIPTION OF THE SEQUENCE LISTING

SEQ ID NO: 1

Nucleotide sequence of the ef gene and the adjacent sequences and the EF amino acid sequence derived therefrom. The presumed ribosome binding site, the −35 and −10 regions of the presumed promoters, and the regions with complementary symmetry are marked. The possible cleaving site for signal peptidase is between nucleotides 498–499.

SEQ ID NO: 2

Nucleotide sequence of the fragment encoding the *S. suis* type 2 ef* gene of strain 1890 and the deduced amino acid sequence of the EF* protein of class I. The putative ribosome binding site, the −35 and −10 regions of the putative promoter sequences, the repetitive regions R1–R11, and the putative termination signals are indicated. The region between the nucleotides 2859 and 5228 is absent in the gene encoding the 110 kDa EF protein. The region between the nucleotides 3423 and 4456 is absent in the genes encoding the call IV and class V EF* proteins.

SEQ ID NO: 3

Nucleotide sequence of the 4.6 kb EcoRI-HindIII fragment with the mrp gene of *S. suis* type 2 and the MRP amino acid sequence derived therefrom. The probable ribosome binding site, the −35 and −10 regions of the presumed promoter sequences, the region of complementary symmetry beyond the mrp gene, the repeating amino acid sequences and the envelope anchor region are indicated.

BRIEF DESCRIPTION OF THE DRAWINGS

FIG. 1: Restriction maps of ef containing fragments, subcloned into the plasmid vector pKUN19 (24). The open reading frames are boxed. Restriction sites: B:BamHI; Bg:BglII; E:EcoRI; KKpnI; N;NarI; P;PstI; S;SnaBI; Sa:SalI, Sp:SpeI.

FIG. 2: Schematic representation of the gene encoding the 110 kDa EF protein and the flanking regions. EF is encoded by the open reading frame 1 (ORF1). The 3' end of ORF1 is overlapping with the 5' end of ORF2. ORF2 and ORF3 are separated by a TAA stop codon. Restriction sites of interest are indicated.

FIG. 3: Schematic representation of the PstI-SnaBI fragment of the ef* genes of 5 different classes of the ef gene. The arrows indicate the repeated amino acid units. The lines indicate regions present in the different strains. The gaps indicate the regions lacking in the different strains.

FIGS. 4A–4B: Nucleotide sequences near the ends of the fragments lacking in the ef* genes of class IV and V (A) and in the ef gene (B). The uppermost and middle sequences represent regions flanking the left and right ends of the lacking fragments. The bottom sequences show the junctions as found in the class IV and V ef* genes (A) and in the ef gene (B). Directly repeated sequences are shown in boxes. The bold nucleotides indicate the first bases of the translational triplets. The numbers refer to the nucleotide positions in the ef* gene of class I (SEQ ID NO: 2).

FIGS. 5A–5B: A. Restriction maps of the DNA inserts of putative MRP-positive recombinant bacteriophages. The thick line indicates the DNA region which is present in all of these clones. Restriction sites: E:EcoRI; H:HindIII; X:XbaI; K:KpnI; S:SacI. B. Parts of the DNA inserts subcloned in the plasmid vector pKUN19 (24).

FIG. 6: Western blot analysis of proteins, encoded by recombinant plasmids and recombinant bacteriophages, which have been selected with monoclonal antibodies against MRP. Lane 1: negative control; proteins extracted from the cell wall of a MRP-negative strain of *S. suis*. Lane 2: crude MRP preparation which contains proteins extracted from the cell wall of strain D282. Lane 3: PMR10-1. Lane 4: pMR7-2. Lane 5: pMR9-1. Lane 6: pMR9-2. Lane 7: pMR10-1. Lane 8: pMR10-2. Lane 9: lambda GEM11 with control insert. Lane 10: lambda clone 7. Lane 11: lambda clone 9. Lane 12: lambda clone 10. Lane 13: lambda clone 11.

FIG. 7: Western blot of the protoplast supernatant (PPS), culture supernatant (Cult. Sup.), and membrane vesicle (Membr.) fractions probed with anti-MRP/EF rabbit K191 serum (diluted 1:500). The lane designations are numbered strain designations.

FIG. 8: Western blot of cell culture supernatants of selected *S. suis* type 2 strains probed with rabbit anti-MRP/EF serum (K191), anti-MRP serum, and anti-EF serum (1:500 diluted). The PAbs revealed three *S. suis* type 2 phenotypes: MRP+EF+, MRP+EF− and MRP− EF−. The lane designations are strain designations. Reference strain 1 (D-282) and strains 3 to 9 (MRP+EF+) were isolated from pigs with *S. suis* meningitis. Reference strain 2 (T-15) and strains 10, 12, 16, and 17 were isolated from the tonsils of healthy pigs. Strains 22, 23, 24, 25, 26, 28, and 29 were isolated from human patients.

FIG. 9: Hydropathy profile (25) of MRP. Sequences above and below the line represent hydrophobic and hydrophilic regions respectively.

FIG. 10: Homology between the amino acid sequences at the C terminus of MRP and several cell-envelope associated proteins of gram-positive bacteria. The amino acid sequence of S. suis MRP was compared with M6 protein of Streptococcus pyogenes (20), protein A of Staphylococcus aureus (16), protein G of group G streptococci (10), AP4 of S. pyogenes (13), LP of Lactococcus lactis (46), WAP4 of S. mutans (11), T6 of S. pyogenes (38), and Fn-BP of S. aureus (39).

FIG. 11: Comparison of the amino acid sequence of the repeat units in MRP. Homologous regions are enclosed in boxes.

FIGS. 12A–12C: Fragments of the mrp and ef genes that were used as a probe. On top of each figure is the localisation of restriction sites that were used to create the probes. The fragments which were used as probes are indicated with solid bars. Left of the solid bar is the abbreviation of the probe. The arrow indicates the open reading frame (ORF) of each gene.

FIG. 12A: Probes of the mrp gene. The SacI and HindIII sites are not authentic but are generated by subcloning fragments of the mrp gene.

FIG. 12B: Probes of the ef gene.

FIG. 12C: Probe of the ef* gene. The open bar indicates the insert sequence of ef* that is not part of the ef gene.

FIG. 13: Specificity of PCR. 10 ng of chromosomal DNA of S. suis type 2 strains was used in the PCR with the primers p-15, p-16, p-34, and p-35. Lanes 1 to 4 contained amplified DNA of MRP$^+$EF$^+$ strains (D282, 3, 10, and 22), lanes 5, 6, 7, and 9 of MRP$^+$EF* strains (17, 24, 26, 28), lanes 10 to 14 of MRP$^-$EF$^-$ strains (T15, 12, 16, 18, and 25), and lane 15 contained the negative control; all ingredients except DNA. Lanes 8 and 16 contained 300 ng size marker Lambda DNA digested with HindIII and EcoRI.

FIG. 14: Dot spot hybridization of 13 S. suis type 2 strains with the mrp and ef probes. In each experiment, row A contains 1 μg/spot DNA of four MRP$^+$EF$^+$ strains; D282, 3, 10 and 22, and one positive control. Row B contains four MRP$^+$EF* strains: strain 17, 24, 26 and 28; and row C five MRP$^-$EF$^-$ strains; T15, 12, 16, 18 and 25.

DETAILED DESCRIPTION OF THE INVENTION

EXAMPLE 1

Figure 1:
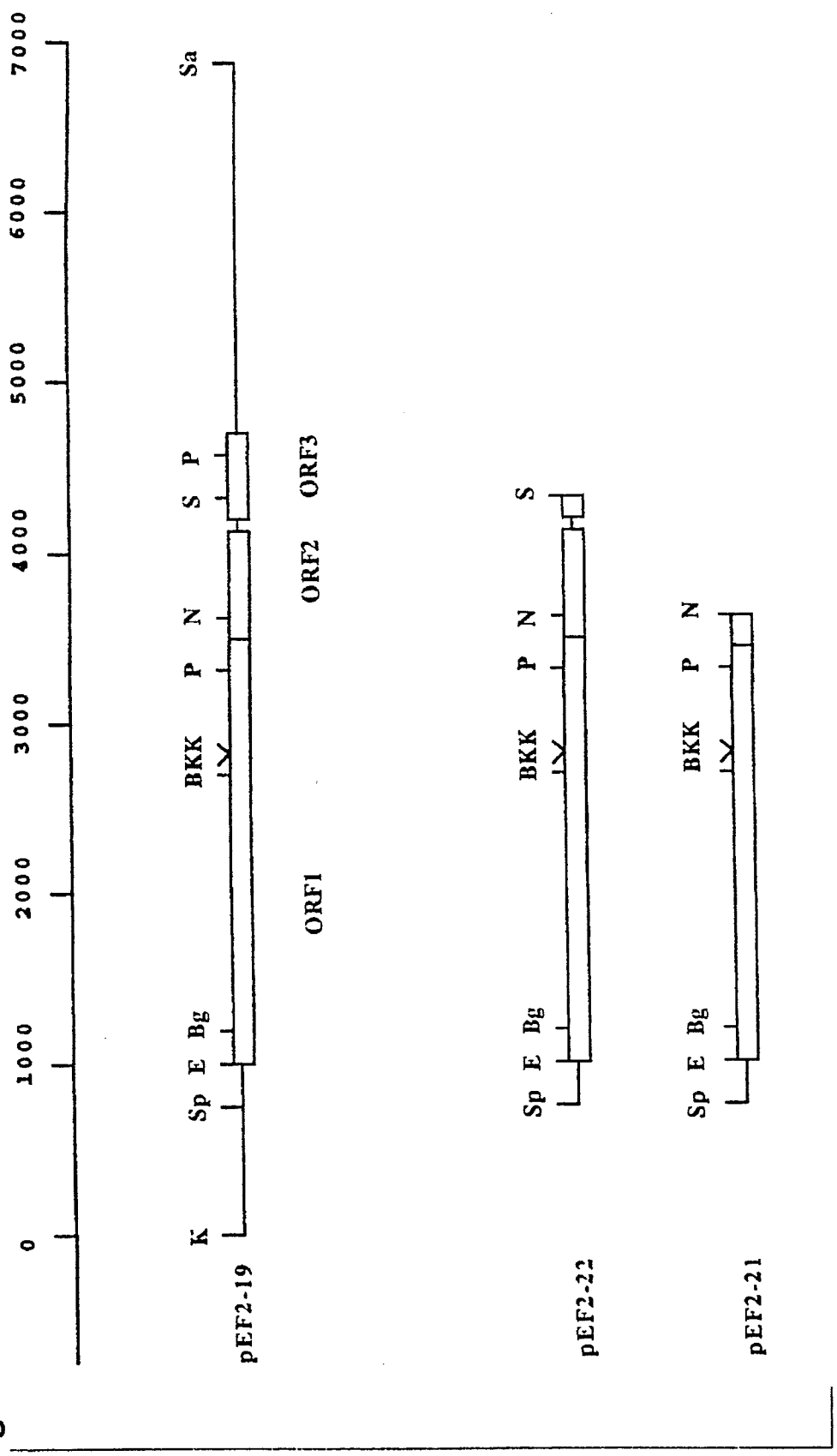
Figure 2:
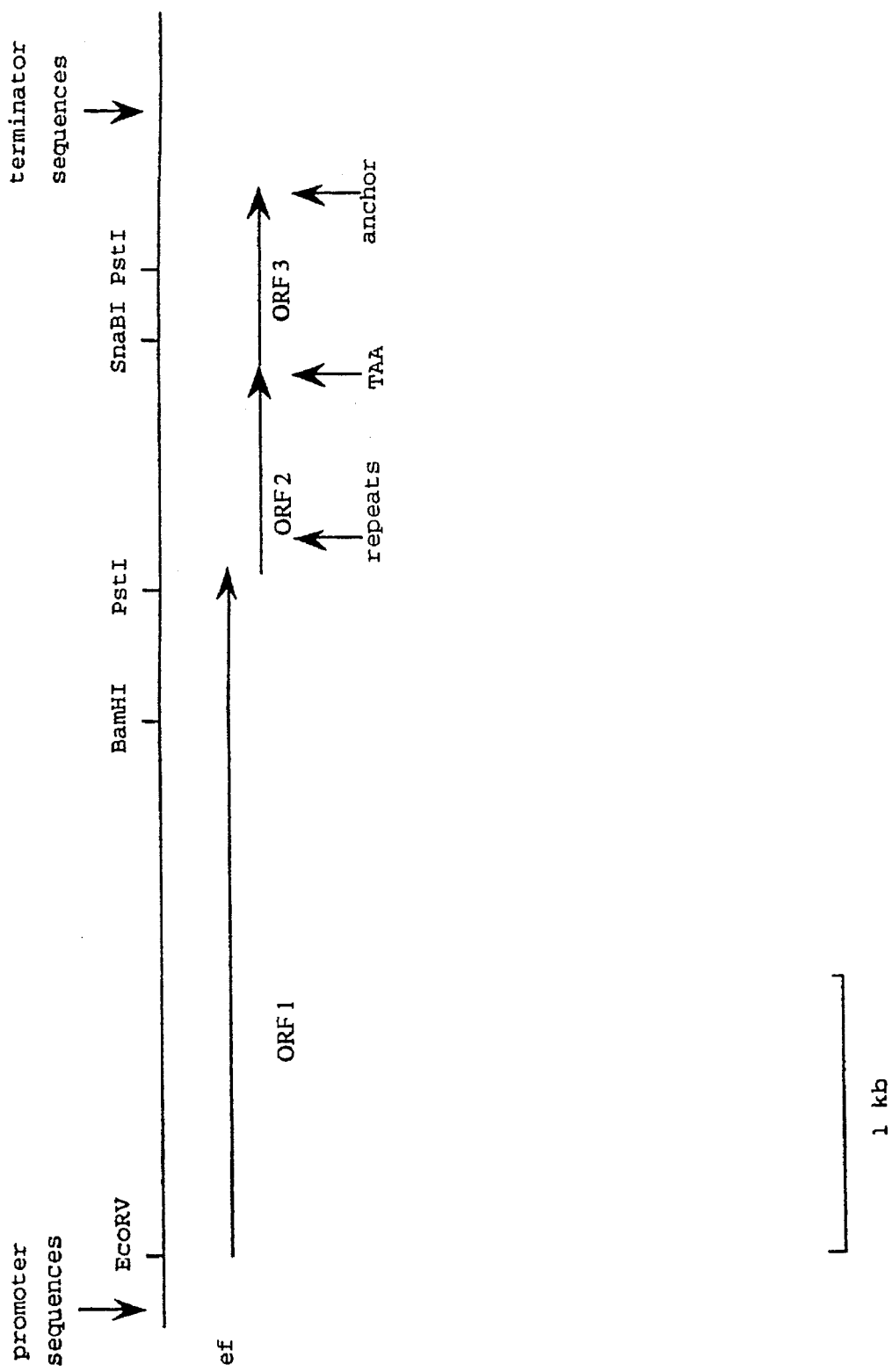

Cloning and nucleotide sequence analysis of the gene encoding the 110 kDa extracellular protein of pathogenic Streptococcus suis type 2 strains

MATERIAL AND METHODS

Bacterial strains and growth conditions. E. coli strains JM101 (29) and LE392 (33) were used as hosts for recombinant plasmids and bacteriophages. The pathogenic MRP$^+$EF$^+$ strain D282 of S. suis type 2 (43) was used for the isolation of chromosomal DNA. E. coli strains were grown in Luria broth (30). Ampicillin was added as needed to a final concentration of 50 μg/ml. S. suis strains were grown in Todd-Hewitt broth (Oxoid, Ltd., London, England).

Construction and immunological screening of the DNA library. A DNA library of S. suis type 2 strain D282 was constructed in LambdaGEM-11 as recommended by the manufacturer of the cloning vector (Promega, Madison, USA). Recombinant bacteriophages were plated on E. coli strain LE392 and incubated for 16 h at 37° C.

Nitrocellulose filters (Schleicher and Schuell, Inc., Dassel, Germany) were placed on the plaques, and the plates were further incubated for 2 h at 37° C. Recombinants that produced EF were visualized with monoclonal antibodies (Mabs) directed against EF (Example 4). Bound antibodies were detected with anti-mouse serum conjugated with alkaline phosphatase (Zymed Laboratories, Inc., San Francisco, USA) as described by Maniatis et al. (28). Selected EF positive clones were purified by several rounds of single plaque isolation and immunological screening.

Sodium dodecyl sulfate (SDS) polyacrylamide gel electrophoresis (PAGE) and Western blot analysis. Proteins were separated by SDS gel electrophoresis in which 4% stacking and 6% separating gels were used (26). The separated proteins were transferred to nitrocellulose in a Semi-Dry transfer cell (Bio-Rad Laboratories, Richmond, USA). Specific proteins were visualized by use of polyclonal antibodies (Pabs, Example 4) or Mabs directed against EF and anti-rabbit or anti-mouse sera conjugated with alkaline phosphatase (Zymed Laboratories).

DNA manipulations and nucleotide sequence analysis. Selected restriction fragments were (sub)-cloned in the plasmid vector pKUN19 (24) by standard molecular biological techniques (28). Progressive unidirectional deletions were made with the Erase-a-Base system from Promega (Madison, USA). DNA sequences were determined by the dideoxy chain termination method (37). DNA and protein sequences were analysed by the software packages PCGENE (Intelli-genetics Corp., Mountain View Calif.) and Wisconsin GCG (University of Wisconsin).

RESULTS

Cloning of the ef gene. A DNA library was constructed by isolating chromosomal DNA from strain D282 of S. suis type 2. This DNA was partially digested with the restriction enzyme Sau3A and cloned into the bacteriophage Lambda-GEM11 replacement vector. The library contained approximately 5×10$^5$ recombinants per μg of DNA. Two thousand plaques of recombinant phages were tested for the presence of antigenic determinants of EF by use of a Mab directed against EF. Two plaques were positive. The expression of EF by the two selected recombinant bacteriophages was studied by Western blotting to analyse the proteins eluted from plaques. Both recombinants encoded a protein that comigrated with EF secreted by S. suis and that was recognized by Mabs directed against EF. Thus both recombinant bacteriophages contained the complete genetic information for EF. The genetic information for EF on the recombinant bacteriophages was localized using restriction enzyme analysis. The two clones shared a DNA region of about 13 kb. Parts of the common DNA region were subcloned into plasmid pKUN19 (FIG. 3) and the proteins expressed by the recombinant plasmids were analyzed by Western blotting. The plasmid containing the 6.8 kb KpnI-SalI fragment (pEF2-19, FIG. 3) encoded a protein with a molecular weight identical to EF, that was recognized by Mabs directed against EF. Plasmids containing the 5.8 kb EcoRV-SalI or the 5.3 kb BglII-SalI fragment, however, did not express EF. These data indicate that the EcoRV and the BglII sites are within regions required for EF expression.

Nucleotide sequence of the ef gene. The nucleotide sequence of the fragment comprising the EF encoding region was determined. The sequence SEQ ID NO: 1 showed the presence of 3 major open reading frames (ORFs). ORF1 (from nucleotide 361 to 2890), ORF2 (from nucleotide 2856 to 3459) and ORF3 (from nucleotide 3462 to 4053) encoded polypeptides of 843 amino acids, of 201 amino acids and of 197 amino acids respectively. ORF1 contained a putative ATG start codon that is preceded by a sequence that is similar to ribosome binding sites of several types of gram-positive bacteria (17). In contrast, neither a start codon, nor a ribosome binding site upstream of the ORFs 2 and 3 could be found. The 3' end of ORF1 and the 5' end of ORF2 are overlapping, albeit in different frames. The ORFs 2 and 3 are separated by a single TAA stop codon. Upstream of ORF1 two putative promoter sequences were found that resembled the −35 and −10 consensus sequences of promoters commonly found in gram-positive bacteria (FIG. 1A). Downstream of ORF3, two regions of extended dyad symmetry were present. Because both regions contained a stretch of thymidine residues at the end of the potential stem-loop structures, these potential transcription terminators are likely to be rho-independent (34, 40). Because the sequence data did not reveal obvious transcription and translation signals upstream of, or within ORF2 and ORF3, it is doubtful that these ORFs express proteins. Another possibility is that the entire sequenced region contains one large open reading frame. This situation would occur if only two sequence errors were present: a +1 base pair frame shift in the region 2856 to 2892 and an error in the stop codon at position 3459. This possibility was excluded by sequencing the ef gene from three additional, independently selected clones. Fragments of the initial clones were used as hybridization probes in order to isolate these clones from the chromosome. The nucleotide sequences of these fragments were identical to those presented in SEQ ID NO: 1

Figure 3:
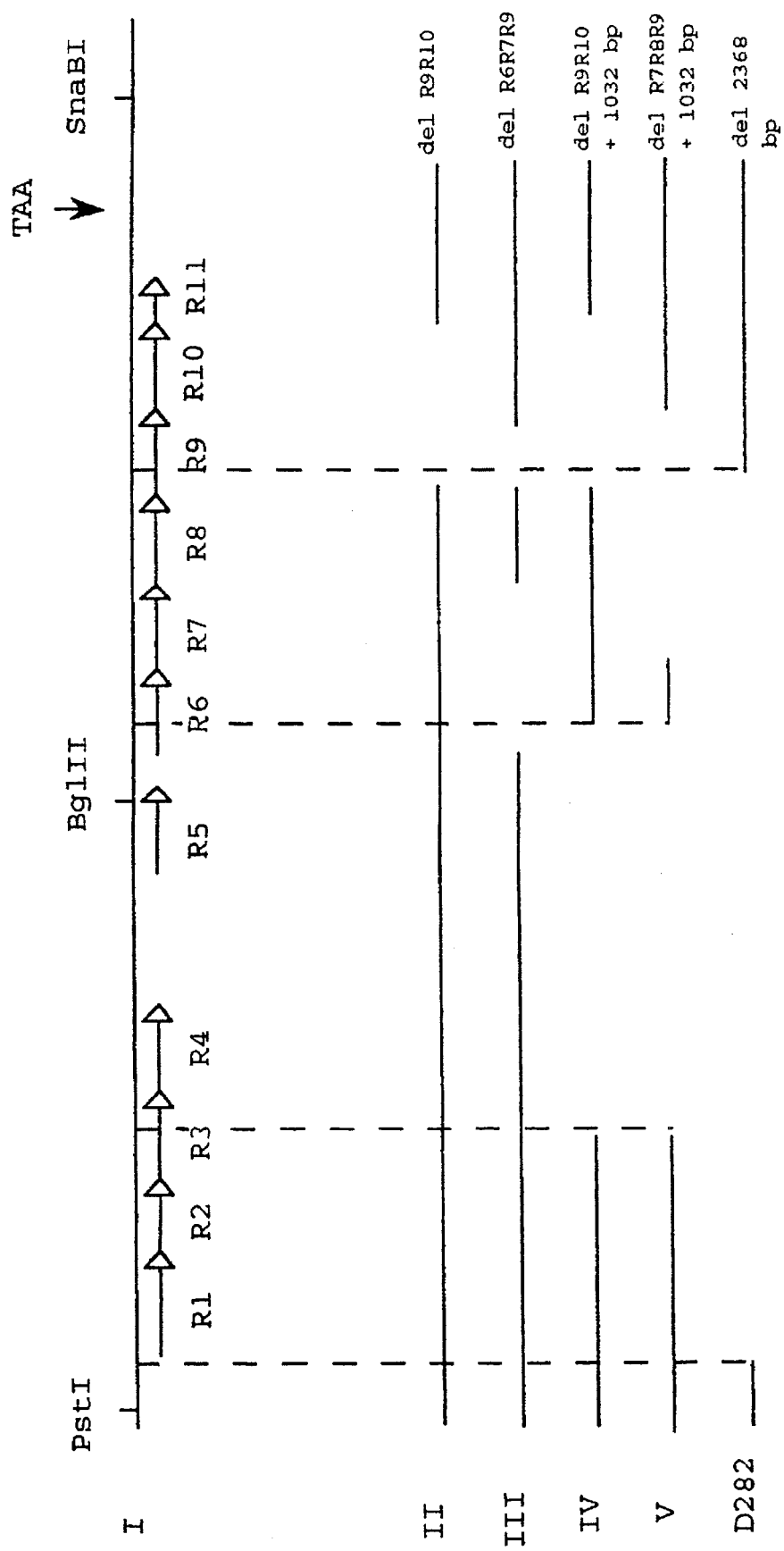

Amino acid sequence of EF. Because only ORF1 was preceded by appropriate expression/initiation signals, this ORF probably encodes EF. This was confirmed by subcloning two fragments into plasmid pKUN19: a SpeI-SnaBI fragment, that contained the entire ORFs 1 and 2 and a SpeI-NarI fragment, that contained ORF1 and the 5' end of ORF2 (FIG. 3). The proteins expressed by the recombinant plasmids were analysed by Western blotting. In E. coli both recombinant plasmids encoded a protein that was recognized by a Mab directed against EF and that had a molecular weight identical to that of EF secreted by S. suis. Therefore, ORF1 encodes EF. The molecular weight of the ORF1 product calculated from the sequence (90,000) differed, however, from that of EF estimated from SDS polyacrylamide gels (110,000).

EF is exclusively found in the supernatant of S. suis cultures, and thus the protein is expected to be preceded by a signal peptide. Indeed, the first 46 amino acids of the deduced amino acid sequence of EF are characteristic of a typical signal peptide. An N-terminal part that contained six positively charged amino acids was followed by a hydrophobic core of 21 amino acids and a putative signal peptidase cleavage site (45). The hydropathy pattern (25) of the deduced amino acid sequence showed that, apart from the signal peptide, the EF protein was very hydrophilic and did not contain extended hydrophobic regions (cf. MRP, Example 3). No significant similarities were found between the deduced amino acid sequence of EF and the protein sequences in the EMBL Data Library.

Although appropriate translation initiation signals upstream of ORF2 and ORF3 could not be found, the deduced amino acid sequences of ORF2 and ORF3 showed some properties which raised doubt to the idea that those frames are not expressed. The N-terminus of the putative ORF2 protein showed two highly repetative units of 57 amino acids (identity 82%). The C-terminus of the putative ORF3 protein is functionally similar to C-terminal regions of several cell-envelope located proteins of grampositive bacteria (10, 12, 13, 16, 41). A hydrophobic region was preceded by the conserved sequence Leu-Pro-X-Thr-Gly-Glu and followed by a highly hydrophilic region. This similarity suggests that the putative ORF3 protein is associated with the cell-envelope.

EXAMPLE 2

Cloning and nucleotide sequence analysis of genes encoding extracellular proteins of non-pathogenic Streptococcus suis type 2 strains

MATERIALS AND METHODS

Bacterial strains and growth conditions. Escherichia coli strain JM101 (29) was used as host for recombinant plasmids. Seventeen MRP⁺EF* strains of S. suis type 2 were isolated from human patients, five strains from tonsils of slaughthered pigs, seven strains from organs of diseased pigs and from two strain the origin was unknown (Example 4). The E. coli strain was grown in Luria broth (30). Ampicillin was added as needed to a final concentration of 50 µg/ml. Streptococcus suis strains were grown in Todd-Hewitt broth (Oxoid, Ltd., London, England).

Genomic DNA and oligonucleotides. Genomic DNA was isolated by lysis in proteinase K/SDS solution, extraction with phenol/chloroform and precipitation with ethanol (28). The sequences of the oligonucleotides used in the polymerase chain reaction (PCR) were: 5'-ATGTAATTGAAT-TCTCTTTTTAAGT-3' and 5'-AAACGTCCGCAGACT-TCTAGATTAAAAGC-3'. These oligonucleotides correspond to the positions 35 to 59 and 4308 to 4279 in the S. suis type 2 ef gene SEQ ID NO: 1. The underlined sequences indicate the recognition sites for the restriction enzymes EcoRI and XbaI.

DNA manipulations and nucleotide sequence analyses were carried out as described in Example 1.

SDS - PAGE and Western blot analysis were carried out as described in Example 1.

Southern hybridization. DNA was transferred to Gene-Screen Plus membranes (New England Nuclear Corp., Dreieich, Germany) as described by Maniatis et al. (28). DNA probes were labeled with ($^{32}$P)dCTP (3000 Ci/mMol, Amersham Corp., Arlington Heights, USA) by the use of a random primed labeling kit (Boehringer GmbH, Mannheim, Germany). The blots were hybridized with DNA probes as recommended by the supplier of the Gene-Screen Plus membranes. After hybridization the membranes were washed twice with a solution of 2×SSC (1×SSC is 0.15M NaCl plus 0.015M trisodium citrate, pH 7.0) for 5 min at room temperature and twice with a solution of 0.1×SSC plus 0.5% SDS for 30 min at 65° C.

Amplification of genomic DNA fragments by Polymerase Chain Reaction (PCR). PCR was used to amplify ef* sequences. Genomic DNA from different MRP⁺EF* strains of S. suis type 2 was used as a template. Amplified DNA fragments were isolated by agarose gelelectrophoresis and extraction from the gel with Gene Clean (Bio101, La Jolla, USA). The purified fragments were digested with EcoRI and XbaI and cloned into the plasmid pKUN19 (24). To exclude mistakes in the DNA sequences as a result of the PCR, six independently choosen clones were mixed prior to the nucleotide sequence analyses.

RESULTS

Western blot of EF* proteins. Culture supernatants of strains of *S.suis* type 2 belonging to the MRP⁺EF* phenotype contained proteins that were recognized by Mabs directed against EF (Examples 4, 6). The molecular weights (MW) of these proteins varied and were higher than that of EF. The proteins secreted by thirty-one strains of the MRP⁺EF* phenotype were compared with those secreted by a strain of the MRP⁺EF⁺phenotype. EF* proteins of five different molecular weight classes were found. Three strains synthesized an EF* protein of approximately 195 kDa (class I); eighteen an EF* of approximately 180 kDa (class II); one an EF* of approximately 175 kDa (class III); five an EF* of approximately 160 kDa (class IV) and four an EF* of approximately 155 kDa (class V).

Southern hybridization of ef* genes. The relationship between the genes encoding the 110 kD EF and the EF* proteins was studied. Chromosomal DNA of different MRP⁺ EF* strains (two representatives of each class were taken) and of the MRP⁺EF⁺strain D282 (43) was digested with the restriction enzyme PstI. The various DNAs were hybridized with a $^{32}$P labeled EcoRV-SnaBI fragment containing the entire ef gene (FIG. 4, see Example 1). The results showed that the DNA digests of the MRP⁺EF* as well as the MRP⁺EF⁺strains contained two PstI fragments that strongly hybridized with the probe. These data indicated that the genes encoding the 110 kDa EF and the EF* proteins are strongly related. The length of the largest hybridizing fragment was the same in all strains. In contrast, the length of the smallest hybridizing fragment differed between the strains. Moreover, the variation in length of the smallest hybridizing fragment correlated well with the variation in the molecular weight of the EF* proteins secreted by the different strains. Since the smallest hybridizing fragment is located at the 3' end of the ef gene (FIG. 4, Example 1), these data suggest that the ef and ef* genes differed mainly at their 3' ends.

Cloning of ef* genes. The genes encoding the different EF* proteins were obtained using PCR to amplify the ef* containing DNA fragments. Genomic DNA of 5 different MRP⁺EF* strains of *S. suis* type 2 (one representative of each class) was used as a template. The amplified fragments were digested with restriction enzymes EcoRI and XbaI and cloned into *E. coli*.

Ef* gene of class I. The nucleotide sequence of a 6.8 kb EcoRI-XbaI fragment containing the entire ef* gene of class I and the regions flanking it was determined. Analysis of the sequence revealed two open-reading frames (ORFs, SEQ ID NO. 2). The first ORF (from nucleotide 361 to 5827) and the second ORF (from nucleotide 5830 to 6421) encoded polypeptides of 1822 amino acids and 197 amino acids respectively. Based on its size the first ORF is expected to encode the EF* protein (195 kDa). The ORFs were separated by a single TAA stop codon. The first ORF contained a putative ATG start codon that was preceded by a sequence similar to bacterial ribosome-binding sites (17). In contrast, the second ORF was not preceded by an appropriate start codon, nor by a putative ribosome-binding site.

Figure 5A:
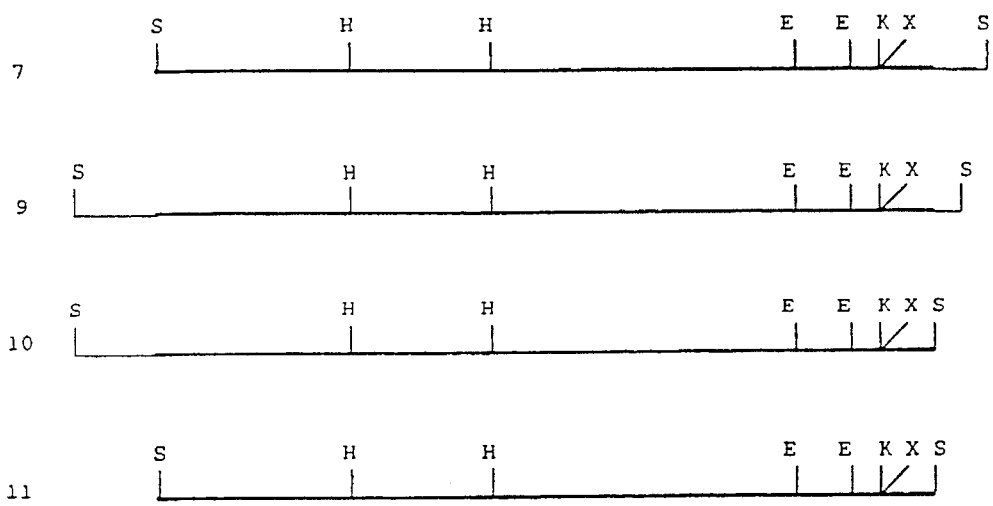
Figure 5B:
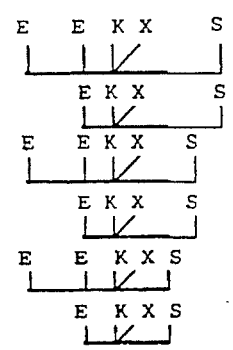

The first 46 amino acids of the deduced amino acid sequence of the EF* protein had the characteristics of a typical signal peptide (45). The C terminus of the mature part of the protein contained a number of imperfect repeats of 76 amino acids. In the EF* protein of class I ten and a half repeats were present (denoted as R1 to R11, SEQ ID NO. 2). The first four repeats were contiguous as were the last six and a half repeats. The fourth and the fifth repeated unit, however, were separated by 113 amino acids and the fifth and the six unit by 22 amino acids (FIG. 5). The amino acid sequences of the last five and a half unit were highly conserved, whereas the sequences of the first five units were more variable. One particular amino acid sequence, Asn-Pro-Asn-Leu, was conserved in all repeated units. No significant homology was found between the EF* sequence of class I and any protein sequence in the EMBL Data Library.

Figure 6:
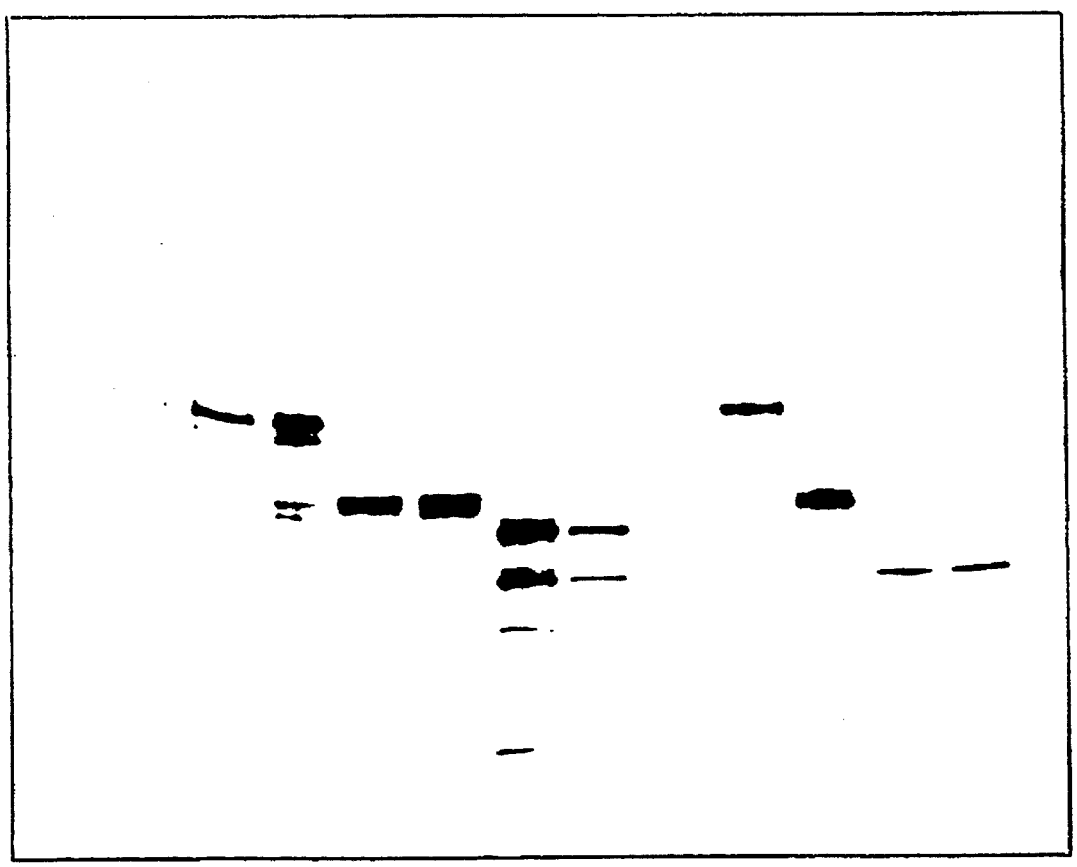

Ef* genes of class II, III, IV and V. Because the genes encoding the various EF* proteins differed mainly at their 3' ends, the nucleotide sequences of the small PstI fragments from the genes of class II, III, IV and V were determined. Comparison of the nucleotide sequences showed that the various ef* genes were highly homologous in this region. The ef* genes differed, however, in the number and the arrangement of repeated units (FIG. 5). Unlike the ef* gene of class I, the ef* genes of class II and IV lacked the R9 and R10 regions; that of class III lacked the R6, R7 and R9 regions and that of class of IV lacked the R7, R8 and R9 regions. In addition, the ef* genes of class IV and V lacked a fragment of 1,032 bp, which contained R4, R5 and parts of R3 and R6. The translational reading frame of the region located at the 3' end of the missing fragment remained the same. The nucleotide sequences at the regions of the left and right ends of this 1,032 bp fragment showed direct repeats of 9 bp (FIG. 6A).

Homology between ef* and ef genes. Because EF* proteins were recognized by Mabs directed against the 110 kDa EF protein and because the ef* genes strongly hybridized with an ef-probe, the ef (Example 1) and ef* genes are assumed to be partly identical. Comparison of the nucleotide sequences of the ef and the ef* gene of class I showed that the 2,499 nucleotides located at the 5' end of the ef and ef* encoding regions were identical. Unlike the gene encoding the EF* protein of class I, the gene encoding the 110 kDa EF protein lacked a 2,368 bp fragment. As a result of this deletion the reading frame was altered and the region located at the 3'-end of the 2,368 bp fragment was translated in different frames in ef and ef* genes. Consequently, the 110 kDa EF protein will not contain the repeated amino acid units. Analysis of the nucleotide sequences at the regions of the left and right ends of the 2,368 bp fragment showed direct repeats of 10 bp (containing one mismatch) (FIG. 6B). Thus, the gene encoding the 110 kDa EF protein could have been the result of a specific deletion of 2,368 bp within an ef* gene. This would implicate that a *S. suis* strain that is non-pathogenic can change into a strain that is pathogenic.

EXAMPLE 3

Cloning and nucleotide sequence of the gene encoding the 136 kDa surface protein (MRP) of *Streptococcus suis* type 2

MATERIALS AND METHODS

Bacterial strains and growth conditions. *Escherichia coli* strain JM 101 (supE,thi,(lac-proAB⁻)[F'traD36, lacI$^q$ZΔM15], 29) was used as a host for recombinant plasmid DNA. *E. coli* strain LE392 [F⁻'hsdR574(rk⁻'mk⁻), supE44, supF58, lacY1, or Δ(lac1ZY)6, galK2, galT22, mel1. trpR55](33) was used as a host for recombinant bacteriophages. The pathogenic MRP⁺EF⁺strain D282 of S.suis type 2 (43) was used for isolating chromosomal DNA. E. coli strains were grown on LB broth (30). Solid LB medium contained 1.5% agar. Ampicillin was added as needed to a final concentration of 50 µg/ml. *streptococcus suis* strains were grown in Todd-Hewitt broth (Oxoid Ltd.)

Southern hybridization was carried out as described in Example 2.

Construction and immunological screening of the DNA library were carried out as described in Example 1 substituting MRP for EF.

SDS - PAGE and Western blot analysis were carried out as described in Example 1 substituting MRP for EF.

Nucleotide sequence analysis was carried out as described in Example 1.

RESULTS

Construction and screening of the library. Chromosomal DNA isolated from strain D282 of *S. suis* type 2 was partially digested with the restriction enzyme Sau3A. A DNA library was then constructed in the bacteriophage LambdaGEM11 replacement vector. Approximately $5 \times 10^5$ recombinants /µg DNA were obtained. A MAb directed against MRP was used to screen 1,400 recombinant plaques for the presence of antigenic determinants of MRP. Five recombinant plaques reacted positive.

Figure 7:
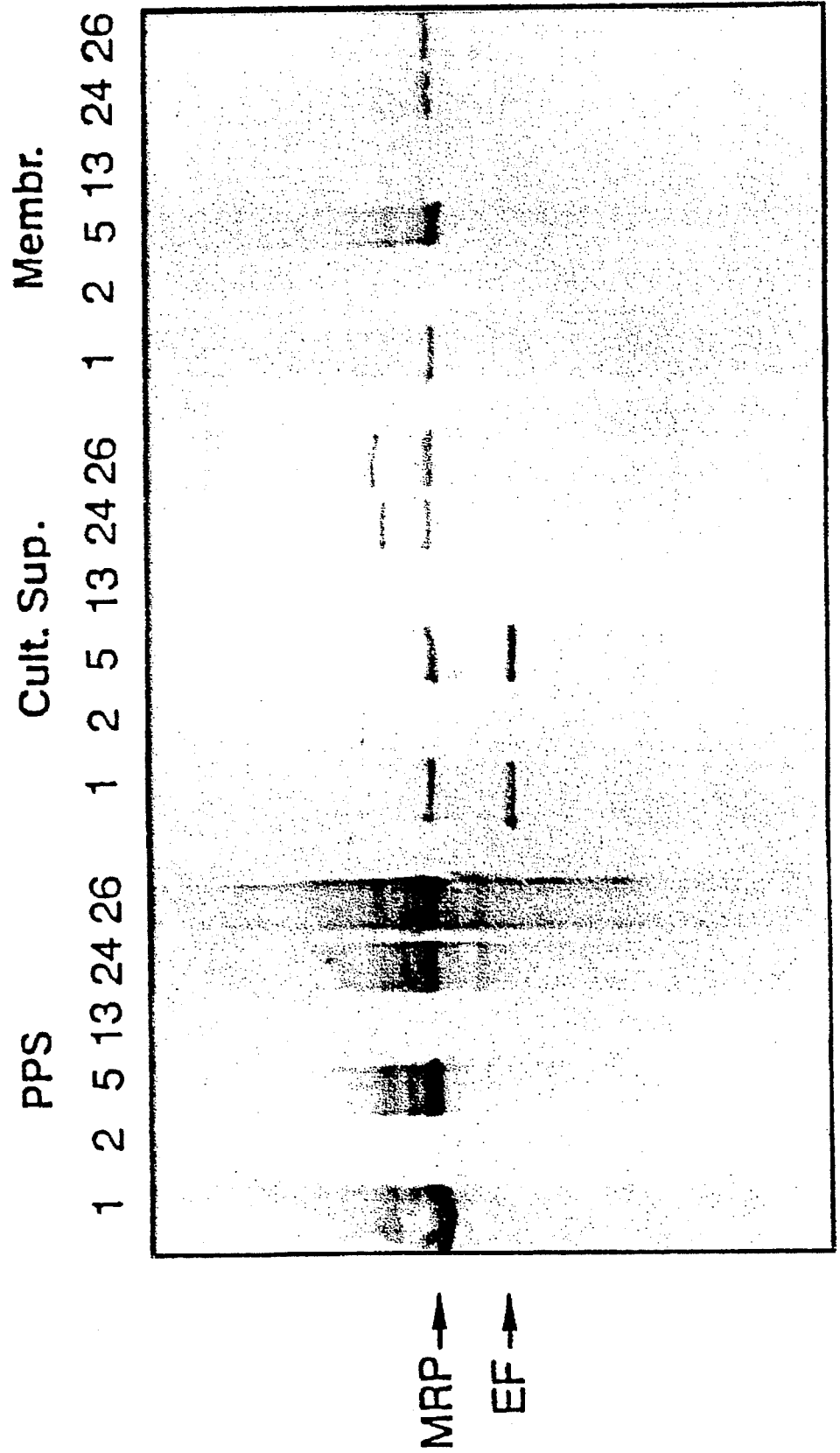
Figure 8:
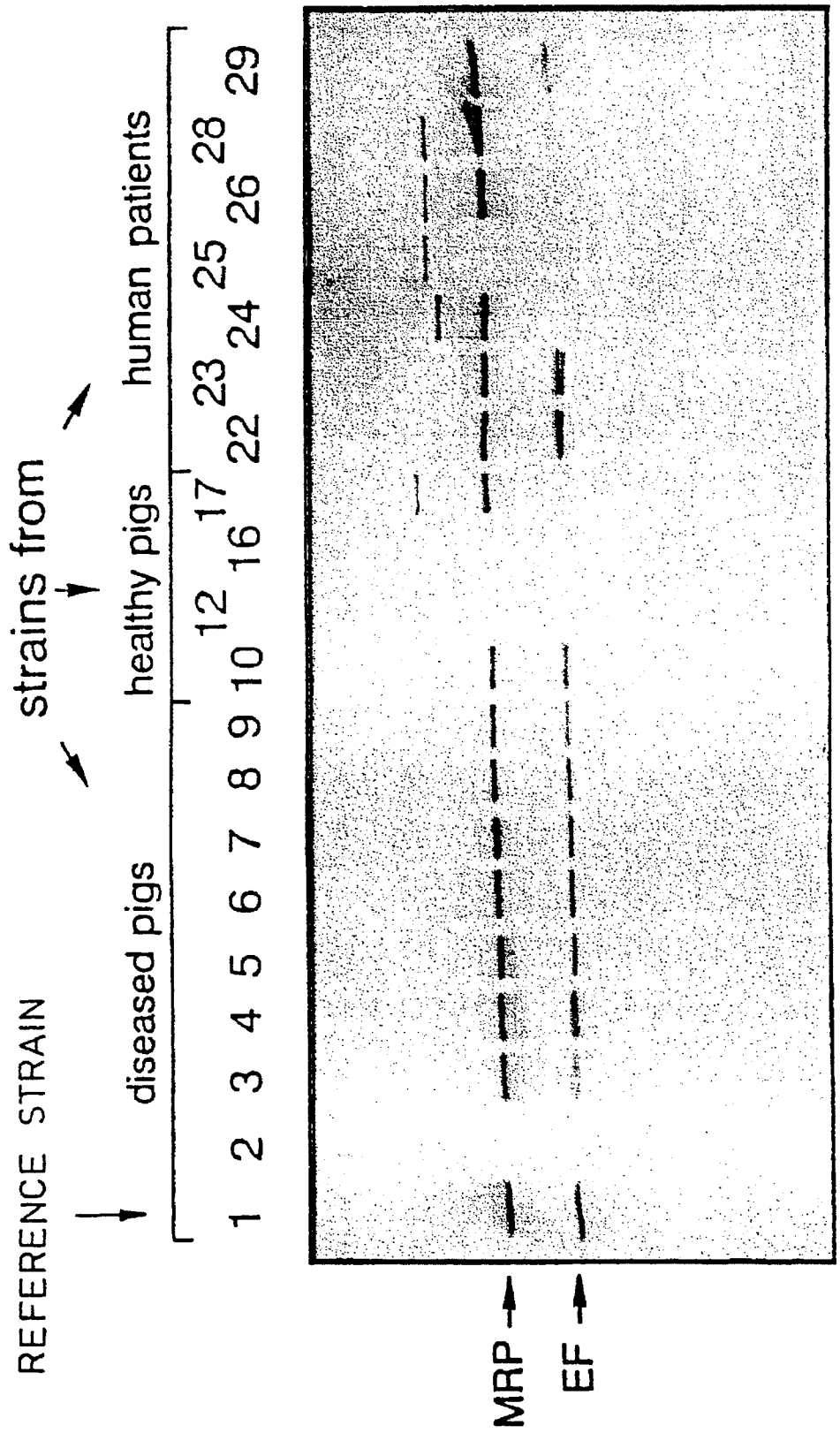

Characterization of the immunoreactive recombinants. The expression of MRP by the five selected recombinant bacteriophages was studied by Western blotting to analyse the proteins eluted from the plaques. All five recombinants encoded proteins that were recognized by MAbs directed against MRP. These proteins, however, had lower molecular weights (MW) than the MRP. Two clones encoded a protein of approximately 70 kDa (clones 10 and 11); two clones encoded a protein of approximately 80 kDa (clones 9 and 12), and one clone encoded a protein of approximately 90 kDa (clone 7). Therefore, it was concluded that the five recombinants did not contain the complete genetic information for MRP. Restriction enzyme analysis was used to compare the DNA inserts of the five recombinants. All clones shared a DNA region of about 17 kb (FIG. 7A). The DNA inserts differed, however, at the 3' and 5' ends. The variation in length at the 3' ends of the inserts correlated well with the variation in MW of the truncated MRP proteins (cf. FIG. 7A). This correlation indicates that MRP encoding sequences were located at the 3' end of the DNA inserts. This was confirmed by subcloning fragments derived from the 3' end of the DNA inserts of clones 7, 9, and 10 (FIG.7B) into plasmid vector pKUN19 (24). These construct encoded truncated MRP proteins that were indistinguishable from the truncated MRP proteins encoded by the recombinant phages (FIG. 8). Deletion of the 0.7 kb EcoRI-KpnI fragment from these contructs stopped the expression of the truncated MRP proteins. This suggests that the expression of mrp is initiated from the 0.7 kb EcoRI-KpnI fragment.

Cloning of the complete mrp gene. The complete gene for MRP was obtained by hybridization of $^{32}$P labeled KpnI-SacI fragment of pMR7-2(FIG. 7B) with EcoRI or KpnI digested chromosomal DNA of strain D282 of *S. suis* type 2. An EcoRi fragment of 7 kb and KpnI fragment of 7 kb hybridized with the probe. Because of its size, the EcoRi fragment was expected to contain the complete mrp gene and because the expression of mrp is initiated from the 0.7 kb EcoRI-KpnI fragment, the KpnI fragment was expected to contain only the 30' end of the gene. Fragments ranging from 6 to 8 kb from EcoRI and KpnI digested chromosomal DNA were isolated, and ligated into the EcoRI or KpnI site of pKUN19, whereafter the ligation mixtures were transformed into E. coli JM101. Thirteen out of 50 selected recombinants clones obtained with the KpnI fragments hybridized with a MRP probe. All of these recombinant clones contained a plasmid (pMR-C) with a 7 kb KpnI insert. In contrast, of 2,500 selected recombinant clones obtained with EcoRI fragments, none hybridized with the probe. Since the 7 kb EcoRI fragment is expected to contain the complete mrp gene, this finding indicates that expression of MRP is toxic in E. coli. Nevertheless, a plasmid (pMR11) with the entire mrp gene could be constructed by combining the 5' end of the mrp gene (isolated from pMR7-2) and the 3' end of the gene (isolated from pMR-C) by forced cloning. The copy number of this plasmid appeared to be strongly reduced, about 20 times, compared to the copy number of pKUN19. The low copy number presumably reduced the toxic effects of high-level expression of MRP in E. coli to tolerable levels. The proteins produced by E. coli cells containing pMR11, were analysed by Western blotting. As expected, these cells produced a 136 kDa protein that comigrated with MRP and that was recognized by PAbs directed against MRP.

Nucleotide sequence of the mrp gene. The nucleotide sequence of a 4.6 kb EcoRI-HindIII fragment, containing the entire mrp gene and the regions flanking it was determined. Analysis of the sequences, SEQ ID NO: 3, revealed an open reading frame of 3,768 nucleotides coding for a polypeptide of 1,256 amino acids (with a calculated MW of 135,794). The putative ATG start codon is preceded by a sequence that is similar to ribosome-biding sites in several types of gram-positive bacteria (17). The nucleotide sequence upstream of mrp resembles the −35 and −10 consensus sequences of promoters commonly found in gram-positive bacteria. downstream of the mrp gene, a region showing extended dyad symmetry can be detected. The potential hairpin structure in the corresponding mRNA has a 12 bp stem separated by a 6 bp loop ($\Delta G = -15.9$ kcal/mol, calculated according to the rules of Tinoco et at., 40). Since the region of dyad symmetry is not followed by a thymidine-rich region, this potential transcription terminator signal appears to be rho-dependent (34).

Figure 11:
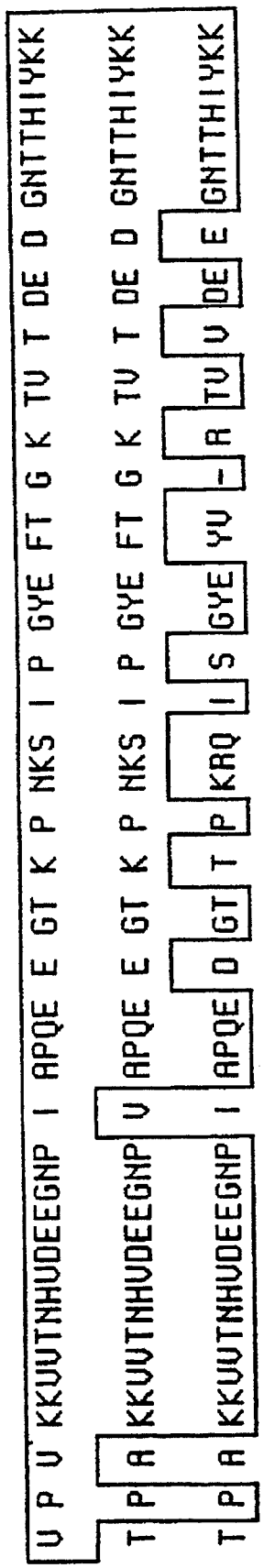
Figure 12:
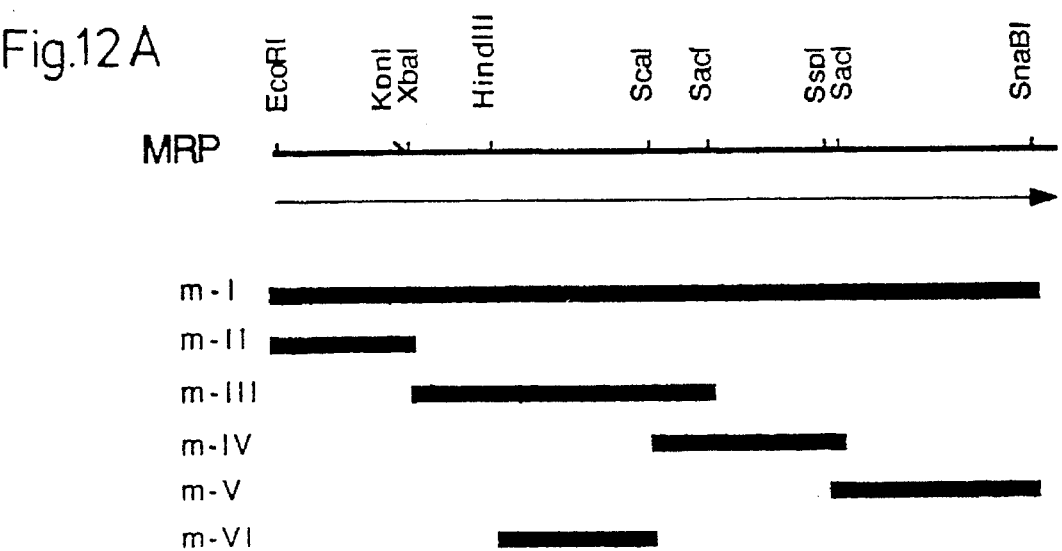
Figure 12:
Figure 12:
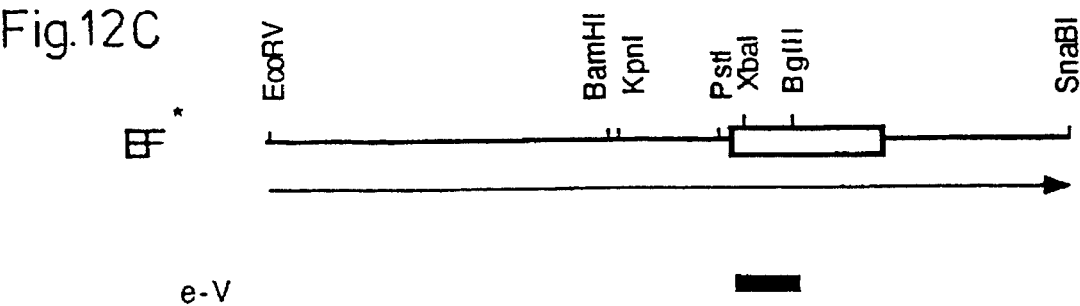

Amino acid sequence of MRP. MRP is a cell-envelope V2 associated pro and must be translocated across the cytoplasmic membrane. The mature protein must therefore contain a signal peptide. Indeed, the first 47 amino acids of the MRP have the characteristics of a typical signal peptide. An N-terminal part that contains seven positively charged residues is followed by a hydrophobic core of 21 amino acids and a putative signal peptidase cleavage site (45, vertical arrow in SEQ ID NO: 3). Cleavage of the signal peptide would result in a mature protein with an MW of 131.094, which is close to the MW (136 kDa) of MRP, estimated from SDS-polyacrylamide gels (Example 4). A second hydrophobic region of 20 amino acids was identified at the C terminus of the protein (FIG. 11). If this region is analogous to other envelope associated proteins of gram-positive bacteria (10, 11, 12, 13, 16, 20, 38, 39, 46), it is probably a cell membrane anchor. A short highly charged region and a region with the Leu-Pro-X-Thr-Gly-Glu amino acid sequence, two regions that flank the presumed cellmembrane anchor, are also highly conserved among surface proteins of gram-positive bacteria (FIG. 12). The amino acid sequence Leu-Pro-X-Thr-Gly-Glu is putatively involved in cell-wall binding.

Figure 13:
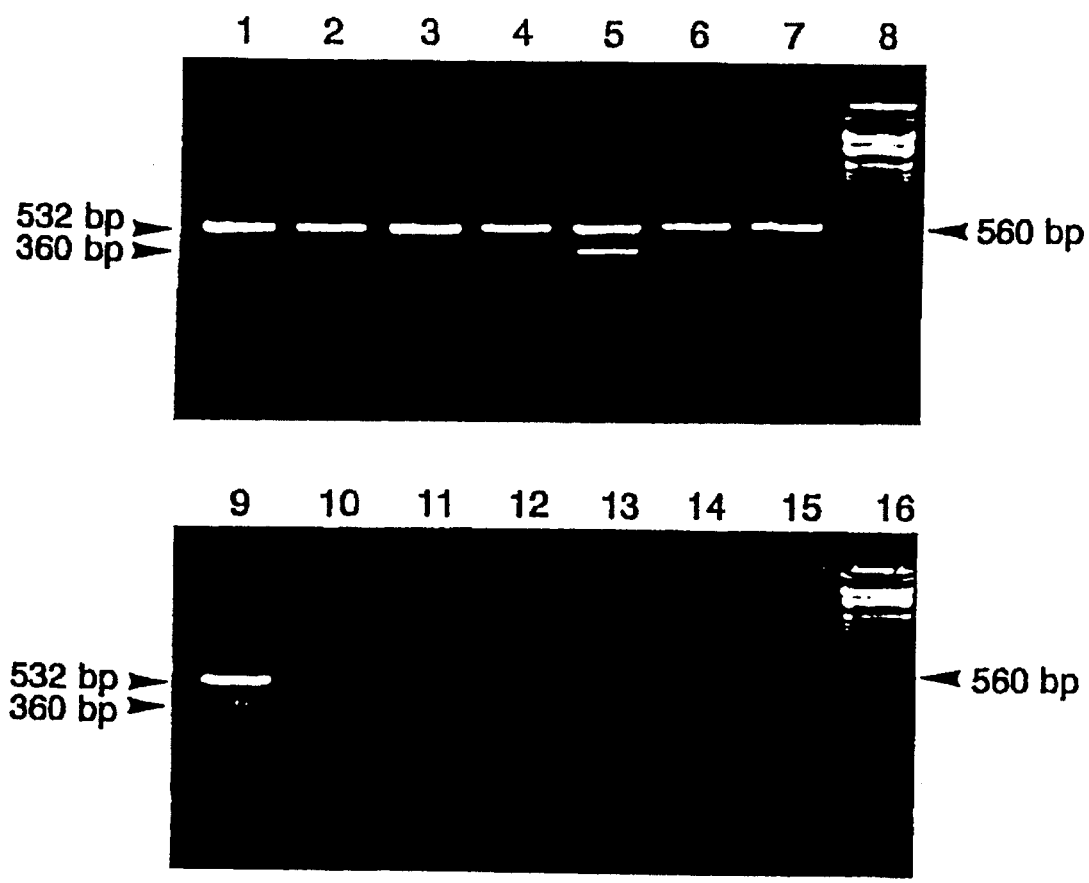

Several other regions were identified in the MRP sequence. The mature form of MRP starts with a unique N-terminal sequence of 824 amino acids. This region is followed by a stretch of amino acids that is rich in proline residues: of 86 amino acids, 26 are proline residues. This region is followed by three repeated units of 54 amino acids (FIG. 13). The first unit is separated from the second by 77 amino acids, but the second and third unit are contiguous. The sequences of the first and the second unit are highly conserved, whereas the third varies. The third repeated unit is followed by the envelope anchor sequence. There was little homology between the MRP sequence and the protein sequences of the EMBL Data Library. One subsequence of MRP, amino acid residues 619–985, however, shared some similarity (17.2% identity in a 377 amino acids sequence) with a sequence of the fibronectin-binding protein of *Staphylococcus aureus* (39).

EXAMPLE 4

Identification of two proteins associated with virulence of *Streptococcus suis* type 2

MATERIAL AND METHODS

Streptococcal isolates. 180 strains of *S. suis* type 2 were obtained from three different sources. A total of 111 of these strains were obtained from four Animal Health Services in the Netherlands. These strains were isolated from organs of diseased pigs in the course of routine diagnostic procedures. Another 42 strains were isolated from tonsils of healthy pigs when they were slaughtered. 27 strains were isolated from human patients with *S. suis* type 2 infections. Tonsillar and human strains were kindly provided by J. P. Arends, Streeklaboratorium voor de Volksgezondheid voor Groningen en Drente, Groningen, the Netherlands. All strains were typed as *S. suis* type 2 by using biochemical and serological methods, as described previously (44). Strain 1 (=D282) had been determined previously to be virulent for newborn germfree pigs and produced MRP, whereas strain 2 (=T-15) was nonvirulent and did not produce MRP (43). Therefore, strains 1 (MRP$^+$) and 2 (MRP$^-$) were used as reference strains.

Culture conditions. A 1-day-old colony of each bacterial strain was grown on Columbia blood agar base (code CM 331; Oxoid, Ltd.) containing 6% horse blood and was incubated overnight at 37° C. in Todd-Hewitt broth (code CM 189; Oxoid). Early stationary growth phase cultures were obtained from the overnight cultures, diluted 10 times in Todd-Hewitt broth, and incubated for 4 h at 37° C.

Cell fractionation. Two cell fractions (protoplast supernatant and culture supernatant) were prepared from each of the 180 strains. Two more cell fractions (protoplasts and membrane vesicles) were prepared from 23 strains selected randomly from the 180 strains. The 23 strains were isolated from both diseased and healthy pigs, as well as from human patients. The four cell fractions were isolated from early stationary growth phase cultures in Todd-Hewitt broth. Protoplasts were isolated as described by Van der Vossen et al. (47). After centrifugation in an Eppendorf centrifuge, the protoplasts and the remaining supernatants (protoplast supernatant) were collected. Membrane vesicles were isolated as described by Driessen et al. (9). The broth cultures were centrifuged at 4,000×g for 15 min, and the culture supernatants were collected.

Preparation of antigens and antisera. After a stationary growth phase culture of strain D-282 was centrifuged, the supernatant was harvested, concentrated by filtration (type PM30 filters; Amicon Corp., Danvers, Mass.) to a concentration of 3 mg/ml, and dialysed once against Tris-buffered saline (50 mM, pH 7.5). This product was used as an antigen for raising polyclonal antibodies (PAb) in rabbits and monoclonal antibodies (MAb) in mice. Rabbits were immunized by intramuscular and subcutaneous inoculation of 2 mg portions of protein emulsified in equal volumes of Freund imcomplete adjuvant. Inoculations were repeated the following day without the adjuvant. After 5 weeks the rabbits were given intravenous booster inoculations of the same antigen dose, but without the adjuvant. After 6 weeks, the rabbits were exsanguinated. The serum of one rabbit (rabbit K191) was used as a probe in the Western blot analysis.

MAbs against the protein EF were raised in BALB/c mice. The mice were immunized intraperitoneally with 0.5 ml portions of antigen containing 25 µg of protein emulsified in equal volumes of Freund imcomplete adjuvant; 3 weeks later this procedure was repeated. After 5 weeks, the mice were given intravenous booster inoculations of the same antigen dose, but without the adjuvant. Hybridoma cell lines were prepared as described by Van Zijderveld et al. (51). After 10 to 14 days, hybridomas were tested for antibodies against EF by using an enzyme-linked immunosorbent assay. Hybridoma culture supernatants (diluted 1:2) were then tested for anti-EF MAb on Western blots of culture supernatants from strain D-282. Binding of MAb to the 110 kDa protein on the nitrocellulose filters was visualized with anti-mouse immunoglobulins conjugated with alkaline phosphatase. The positive cells were cloned twice by limiting dilution in microtiter plates. The resulting monoclonal cell lines were used to produce ascites fluid in pristane-primed male BALB/c mice, as described previously (51).

Indirect enzyme-linked immunosorbent assay for screening hybridoma culture supernatants. Polystyrene microtiter plates (Greiner, Nürtingen, Germany) were coated for 16 h at 37° C. with a solution containing the concentrated, dialysed culture supernatant from strain D-282 (see above) diluted in phosphate-buffered saline (pH 7.2; 0.075 mg of protein per ml), and these preparations were incubated for 16 h at 37° C. Twofold dilutions of hybridoma culture supernatants were applied and tested as described previously (51). Bound antibodies were incubated with anti-mouse immunoglobulins (diluted 1:500) that were conjugated with horseradish peroxidase (HRPO, Nordic, Tilburg, The Netherlands).

Electrophoresis and Western blotting. The various cell fractions were analysed by SDS-PAGE as described by Laemmli (26) on 6 or 12% polyacrylamide. After electrophoresis, the proteins were stained with silver (32). For Western blot analysis, the proteins were electroblotted onto nitrocellulose by using a Multiphor II Nova Blot system (Pharmacia LKB, Uppsala, Sweden). The blots were probed with a 1:500 dilution of rabbit K191 PAb or with a 1:300 dilution of mouse MAb. Bound PAb were visualized with anti-rabbit immunoglobulins conjugated with alkaline phosphatase. Bound MAb were visualized with a 1:1,000 dilution of anti-mouse immunoglobulins conjugated with alkaline phosphatase (Zymed).

RESULTS

Protein profiles of four cell fractions of 23 selected strains. The protein profiles of the protoplast supernatants and membrane vesicle cell fractions from two *S. suis* isolates belonging to each group studied (diseased pigs, healthy pigs, and human patients), prepared from the 23 strains examined were almost identical. In contrast, the protein profiles of the culture and protoplast supernatants differed distinctly. The protein profiles of isolates obtained from diseased pigs contained two protein bands that were absent in the protein profiles of most isolates obtained from healthy pigs. One band represented a 136 kDa protein, which was identified as MRP (43). In the SDS-PAGE analysis, separating gels containing 6% polyacrylamide revealed the presence of MRP in both culture and protoplast supernatants (strains 1, 5, 24, and 26). The second band represented a 110 kDa protein; because this protein was detected only in culture supernatants, it was designated EF. Both MRP and EF were present in the culture supernatant of virulent reference strain 1 (=D-282), but were absent in all cell fractions of nonvirulent reference strain 2 (=T-15). The eight strains isolated from diseased pigs contained both MRP and EF. Six of the eight strains isolated from healthy pigs lacked these proteins. Six of the seven strains isolated from human patients contained MRP, but only three of the six also contained EF.

When rabbit K191 PAb directed against culture supernatants were used as probes in the immunoblotting analysis, MRP and EF were clearly detected in the cell fractions of *S. suis* type 2 strains. Protoplast supernatants, culture supernatants, and membrane vesicles of strains 1, 5, 24, and 26 contained the 136-kDa MRP (FIG. 9). Because MRP is a major component of protoplast supernatants, this protein must be localized in the cell envelope of the bacteria. The culture supernatants of strains 1 and 5 also contained the 110 kDa EF. Strains 24 and 26 contained MRP but not EF; strains 2 and 13 contained neither of the proteins.

On the basis of the presence of MRP and EF in culture supernatants, the following three phenotypes of *S. suis* type 2 strains were distinguished: MRP$^+$EF$^+$, and MRP$^+$EF$^-$, and MRP$^-$EF$^-$ (FIG. 10). Proteins bands at various molecular masses higher than 150 kDa reacted with rabbit K191 serum and were visualized in Western blots of culture supernatants of strains 17, 24, 25, 26, and 28. As such proteins were also recognized by the anti-EF MAb, except in the culture supernatant of strain 25, the 110 kDa EF was probably related to these proteins. Western blots probed with the mouse anti-EF MAb showed that all of the strains with the MRP$^+$EF$^-$ phenotype contained higher molecular weight proteins in their culture supernatants. However, none of the strains with the MRP$^+$EF$^+$ phenotype contained such proteins. Probing with rabbit K191 serum revealed high molecular weight proteins in culture supernatants of 12 MRP$^-$EF$^-$ strains, including strain 25. Immunoblotting with anti-EF MAb showed that these proteins were not related to EF. When the four cell fractions were analysed by SDS-PAGE on 12% slab gels, no low molecular weight proteins associated with virulence were detected.

Protein profiles of culture and protoplast supernatants of 180 strains. All 180 *S. suis* type 2 strains were analysed for the occurrence of the three phenotypes in culture and protoplast supernatants by using 6% slab gels. Eighty percent of the strains isolated from the organs of diseased pigs had the MRP$^+$EF$^+$ phenotype (Table 1).

TABLE 1

Prevalence of MRP and EF phenotypes in 180 streptococcal strains isolated from diseased pigs, from healthy pigs when they were slaughtered, and from human patients.

| | No. (%) of strains isolated from: | | |
|---|---|---|---|
| *S. suis* type 2 phenotype | Organs of diseased pigs | Tonsils of healthy pigs | Human patients |
| MRP$^+$EF$^+$ | 86 (77) | 1 (2) | 4 (15) |
| MRP$^+$EF$^-$ | 13 (12) | 5 (12) | 20 (74) |
| MRP$^-$EF$^-$ | 12 (11) | 36 (86) | 3 (11) |

In contrast, only 2% of the strains isolated from tonsils of healthy pigs had this phenotype; 86% of these strains were MRP$^-$EF$^-$. Only 15% of the strains isolated from human patients had the MRP$^+$EF$^+$ phenotype. Among the *S. suis* type 2 strains tested, far more human strains (74%) than porcine strains (12%) had the MRP$^+$EF$^-$ phenotype; 89% of the human strains were MRP$^+$. The MRP$^-$EF$^+$ phenotype was not detected.

EXAMPLE 5

Virulence of *Streptococcus suis* type 2 strains in new-born germ-free pigs.

MATERIALS AND METHODS

Pigs. Fifty-two germ-free pigs, cross-breeds of Great Yorkshire and Dutch Landrace, were obtained from four sows by caesarian sections. Sows in both experiments were full sisters. Pigs were allotted to 12 groups each consisting of 4 or 5 pigs. Each group was housed in a sterile stainless steel incubator. Housing and feeding were as described before (43).

Inocula. Ten *S. suis* type 2 strains belonging to either phenotype MRP+EF+, MRP+EF-, or MRP-EF- were obtained from three sources: from a pig with meningitis, from healthy pigs at slaughter, and from human patients (Table 2). The strains were biochemically and serologically typed as described earlier (44). Strains were stored as stock suspensions on glass beads in Nutrient Broth with 15% glycerol at -70° C. A one-day-old colony of each strain, grown on Columbia blood agar base (Code CM 331, Oxoid) containing 6% horse blood, was incubated overnight at 37° C. in Todd-Hewitt broth (Code CM 189, Oxoid). Early stationary growth phase cultures were obtained by diluting the overnight cultures in Todd-Hewitt broth (1:10) and incubated them at 37° C. Incubation was stopped after approximately 4 h, when the optical density at 600 nm was 0.5. Cultures containing approximately 1 to 3×10$^9$ CFU/ml were then centrifuged at 4000× g for 15 min. The supernatant was analysed for MRP and EF. Then the pellets were washed and suspend at an A$_{600}$=1 in a solution of phosphate-buffered saline (PBS), 139.89 mM NaCl, 2.68 mM KCl, 8.1 mM Na$_2$HPO$_4$, 2.79mM KH$_2$PO$_4$, ph 7.2, and then used as inoculum. *Bordetella bronchiseptica* strain 92932, isolated from the nose of a pig with atrophic rhinitis, was used to predispose pigs to *S. suis* infection (23, 43). The strain was kept on Dorset egg medium. The inoculum was prepared by culturing a 48 hour old colony from sheep blood agar in brain heart infusion broth. After 18 h of incubation at 37° C., this medium contained approximately 10$^9$ CFU/ml. The brain heart infusion broth was diluted (1:100) in PBS to prepare the inoculum.

Electrophoresis and Western blotting. The MRP/EF phenotypes of the *S. suis* strains used as inocula and of the isolates recovered at the end of the experiments were determined. SDS-PAGE as described by Laemmli (26) (6% polyacrylamide) and Western blotting were used to analyse cell culture supernatants of isolates recovered from nasopharynx of all pigs, and from inflamed tissue such as meninges or joints of affected pigs. After electrophoresis the proteins were stained with silver (32). For Western blot analysis, the proteins were electroblotted onto nitrocellulose by the Multiphor II Nova Blot system, according to the recommendations of the manufacturer (Pharmacia LKB). Nitrocellulose filters were incubated either with a 1:1 mixture of mouse anti-MRP monoclonal antibodies (MAb) (11.3 mg/ml) and anti-EF MAb (8.4 mg/ml) each in a 1:200 dilution, or with a 1:500 dilution of polyclonal anti-MRP/EF rabbit serum (K191) (8.2 mg/ml) (Examples 4, 6). Filters were incubated with a 1:1000 dilution of anti-mouse immunoglobulins conjugated with alkaline phosphatase (AP) or a 1:3000 dilution of AP conjugated anti-rabbit immunoglobulin g(γ+κ) (Zymed). Bound antibodies were visualized by adding the substrate bromochloroindolyl phosphate (Sigma, St. Louis, Mo.—nitro blue tetrazolium (Merck, Darmstad, Germany) in phosphatase buffer (100 mM NaCl, 5 mM MgCl$_2$, 100 mM diethanolamine; ph 9.5).

Experimental design. The study consisted of two experiments with an interval of five months. Five day old germfree pigs were inoculated intranasally with a plastic disposable syringe filled with a suspension of *B. bronchiseptica* strain 92932 in brain heart infusion broth. The inocula contained $0.84 \times 10^7$ CFU in experiment I and $1.0 \times 10^7$ CFU in experiment II. Two days post inoculation (pi) the pigs were similarly inoculated inside the sterile incubator with one of the ten *S. suis* type 2 strains (Table 2).

The mean (±SD) inoculum size of these strains was $1.4 (+0.60) \times 10^6$ CFU. All inoculations consisted of a 0.5 ml bacterial suspension in each nostril during the inspiratory phase of breathing. In both experiments strain 3 (MRP+EF+) was used as positive control and strain 12 (MRP–EF–) was used as negative control (see Results section). Pigs were killed either when they became mortally ill or at the end of the experiment (3 to 4 weeks pi), and they were subsequently necropsied.

TABLE 2

Experimental design.

| S. Suis strain no. | S. suis phenotype | Source[1] of S. suis isolation | Dosage[2] of S. suis inoculation | No. of pigs inoculated |
|---|---|---|---|---|
| 3  | MRP+EF+ | meninges pig | 1.84 | 5 |
| 3  | MRP+EF+ | meninges pig | 1.96 | 4 |
| 10 | MRP+EF+ | tonsil pig   | 1.52 | 5 |
| 22 | MRP+EF+ | human        | 2.93 | 4 |
| 17 | MRP+EF– | tonsil pig   | 1.26 | 4 |
| 24 | MRP+EF– | human        | 1.22 | 4 |
| 28 | MRP+EF– | human        | 1.23 | 4 |
| 12 | MRP–EF– | tonsil pig   | 1.05 | 5 |
| 12 | MRP–EF– | tonsil pig   | 0.98 | 4 |
| 16 | MRP–EF– | tonsil pig   | 0.70 | 4 |
| 18 | MRP–EF– | tonsil pig   | 1.10 | 4 |
| 25 | MRP–EF– | human        | 0.97 | 4 |

[1] Strain 3 was isolated during routine diagnostic procedures from a pig with meningitis. Strains 10, 12, 16, and 18 were isolated at slaughter from the tonsils of healthy pigs. Strains 22 (no. 830544), 24 (no. 740113), 25 (no. 821021) and 28 (no 760366) were isolated from human patients with *S. suis* type 2 meningitis. (Numbers between parentheses refer to those by J. P. Arends and H. C. Zanen (2)).
[2] $\times 10^6$ CFU.

Disease monitoring. Pigs were monitored daily for clinical signs of disease, such as fever, dysfunction of the CNS and lameness. Blood samples from each pig were collected three times weekly by venipuncture of the cranial vena cava. White blood cells were counted with a conducting counter (Contraves A.G., Zürich, Switerland) (18). The number of neutrophils was calculated after differential count of Giemsa-stained blood smears. Swabs specimens of nasopharynx and feces were collected daily and plated directly onto Columbia agar containing 6% horse blood. The presence of *S. suis* type 2 and of *B. bronchiseptica* was confirmed by slide agglutination test in which a suspension of the monocultures was mixed with the appropiate hyperimmune rabbit serum (DLO-Central Veterinary Institute, Lelystad, NL). After pigs were killed, they were examined for pathologic changes. Tissue specimens of the CNS, serosae, liver, spleen, and tonsils were bacteriologically and histologically examined as described before (43).

RESULTS

Electrophoresis and Western blotting. When immunoblots were used to analyse culture supernatants of the *S. suis* strains before inoculation, three phenotypes were distinguish. Strains 3, 10, and 22 belonged to the MRP+EF+ phenotype, strains 17, 24, and 28 were of the MRP+EF– phenotype, and strains 12, 16, 18, and 25 belonged to the MRP–EF– phenotype. The rabbit polyclonal antibodies (PAb) recognized proteins that were greater than 150 kDa in the culture supernatants of the MRP+EF – strains. These high molecular weight proteins were also detected by the anti-EF MAb, indicating that the 110 kDa EF and the >150 kDa proteins share epitopes. In both the SDS-PAGE and Western blot, the phenotypes of the *S. suis* strains used as inocula were identical to the phenotypes of the isolates collected at the end of both experiments from tonsils and inflamed tissues of infected pigs.

Clinical signs of disease. In both experiments, rectal temperatures of all pigs inoculated with strains of the MRP+EF+ phenotype increased from day 2 pi onwards, with peaks at 41.8° C. between days 4 and 9. Rectal temperatures of ten pigs inoculated with strains of the MRP+EF– phenotype were higher than 40° C. for short periods of 24 to 96 h between days 2 and 22. Frequency of fever was highest in the MRP+EF+ groups (40%) (Table 3). The frequency of increased polmorphous leucocytes (PML) in blood was highest in the MRP+EF+ groups (Table 3). Analysis of variance was performed on the log of PML counts in blood samples of pigs inoculated with strains of the three phenotypes. Three days before inoculations no significant differences were found between the geometric mean PML counts of the three groups. From day one pi onwards, the means of numbers of PML in blood samples of pigs inoculated with strains of the MRP+EF+ phenotype were significantly higher ($p<0.01$) then in either the MRP+EF+ groups or the MRP–EF– groups. On day 20 pi, the means in the MRP+EF+ and MRP+EF– groups did not differ significantly from each other, but those means differed significantly ($p<0.01$) from the means in the MRP–EF– groups. Morbidity in pigs inoculated with strains of the MRP+EF+ phenotype was 100%. From day 2 onwards, non-specific signs of systemic disease, such as depression, recumbency, lack of appetite, and fever were observed. During the following days, pigs showed more specific signs of disease, such as ataxia, circular movements, opisthotonus, recumbency with paddling, and lameness. The frequency of specific signs of diseases in the MRP+EF+ groups was 57% (Table 3). Nine pigs died in the course of the experiment, and three were killed in the terminal stages of disease. The mortality rate in these groups was thus 12/18 (67). Nine pigs inoculated with strains of the MRP+EF– phenotype developed fever or granulocytosis or showed other nonspecific signs of disease, but did not show specific clinical signs, such as nervous disorders or lameness. Pigs in the MRP–EF– groups did not develop clinical signs of disease (Table 3)

TABLE 3

Frequency of three parameters of disease observed in pigs inoculated with *S. suis* type 2 (10 strains belonging to three phenotypes)

| | Frequency[1] (%) of 3 parameters of disease | | | |
|---|---|---|---|---|
| S. suis phenotype | Fever >40° C. | PML in blood >$10^{10}$/L | Clinical signs of disease specific[2] | non-specific[3] |
| MRP+EF+ | 40 | 78 | 57 | 21 |
| MRP+EF– | 5  | 16 | 0  | 5  |
| MRP–EF– | 0  | 3  | 0  | 0  |

[1] Number of positive records/total number of records
[2] Lameness and nervous disorders such as ataxia, circular movements, opisthotonus, and recumbency with paddling.
[3] Depression, lack of appetite, and recumbency.

Pathologic findings are summarized in Table 4. Severe and frequent inflammations of the CNS, serosa, and joints were only detected in pigs inoculated with strains of the MRP+EF+ phenotype. Pneumonia and bronchitis were observed in various forms. Follicle formation in B cell areas and blast cell formation in T cell areas of the white pulp of the spleen—signs of active immune response—were more frequently observed in pigs inoculated with strains of the MRP+EF− phenotype (50%) than in pigs inoculated with strains of the MRP−EF− phenotype (22%) or strains of the MRP+EF+ phenotype (11%) (Table 4). Some pigs inoculated with MRP+Ef+ showed lymphocytolysis in the germinal centres, while the marginal zone surrounding the white pulp was inflamed, signs of acute septichaemia in young animals (42). Active follicles in tonsils were also more often seen in pigs inoculated with strains of the MRP+EF− or MRP−Ef− phenotype.

TABLE 4

Pathologic lesions detected in various tissues of pigs inoculated with S. suis type 2 (10 strains of three phenotypes

| | No. of pigs with pathologic lesions | | |
|---|---|---|---|
| Tissue and pathologic lesions | phenotype MRP+EF+ (no. tested = 18) | phenotype MRP+EF− (no. tested = 12) | phenotype MRP−EF− (no. tested = 22) |
| CNS | | | |
| Meningitis[1] | 12 | 0 | 0 |
| Encephalitis[1] | 10 | 1 | 0 |
| Choroiditis | 7 | 0 | 0 |
| Malacia | 5 | 0 | 0 |
| Serosae/joints | | | |
| Peri-/epicarditis | 11 | 1 | 1 |
| Pleuritis | 5 | 1 | 0 |
| Peritonitis | 14 | 6 | 0 |
| Polyarthritis[2] | 15 | 0 | 0 |
| Lungs | | | |
| Cath. broncho-pneumonia | 1 | 1 | 1 |
| Fibrinous pneumonia | 3 | 0 | 0 |
| Interstitial pneumonia | 7 | 5 | 5 |
| Bronchitis/ Peribronchiolitis | 2 | 2 | 3 |
| Liver | | | |
| Periportal and/or intralobular foci | 11 | 8 | 3 |
| Spleen | | | |
| Active white pulp | 2 | 6 | 5 |
| Active red pulp | 4 | 0 | 2 |
| Tonsil | | | |
| Active follicles | 3 | 9 | 12 |
| Exudation in crypts | 1 | 5 | 6 |

[1]Affecting cerebrum, cerebellum, pons, mesencephalon and medulla oblongata in various combinations.
[2]Affecting carpal, metacarpal, tarsal, metarsal, knee, elbow, shoulder and hip joints in various combinations.

Bacteriologic findings. From day 1 one pi to the end of the experiment, the streptococcal strains and *B. bronchiseptica* were isolated daily from naso-pharyngeal and fecal swab specimens of all pigs. A Bacillus species was also isolated from day six pi onwards from pigs inoculated with strain 16 (experiment I) and from day 19 pi onwards from pigs inoculated with strain 24 (experiment II). Pigs in the other groups remained free from contaminating bacteria.

At necropsy, *S. suis* type 2 was mostly isolated from organs and tissues (CNS, serosae, and joints) that also showed pathologic changes (Table 5). *B. bronchiseptica* was only isolated from lungs and tonsils. Both *S. suis* and *B. bronchiseptica* were also isolated from the tonsils of all pigs.

TABLE 5

Isolation of streptococci from various tissues of pigs inoculated with S. suis type 2 (10 strains of three phenotypes).

| | No. of pigs from which S. suis was isolated at necropsy | | |
|---|---|---|---|
| Tissue | phenotype MRP+EF+ (no. tested = 18) | phenotye MRP+EF− (no. tested = 12) | phenotype MRP−EF− (no. tested = 22) |
| CNS | 14 | 0 | 0 |
| Serosae | 9 | 2 | 0 |
| Joints | 13 | 2 | 0 |
| Lungs | 6 (9) | 0 (2) | 2 (8) |

[1]Numbers in parentheses indicate number of pigs from which *B. bronchiseptica* was also isolated.

EXAMPLE 6

Discrimination between Virulent and Nonvirulent *Streptococcus suis* type 2 Strains by Enzyme-Linked Immunosorbent Assay

MATERIALS AND METHODS

Bacteria. 179 strains of *S. suis* type 2 obtained from three sources were examined: from organs of diseased pigs in the course of routine diagnostic procedures, from tonsils of healthy pigs at slaughter, and from human patients suffering from *S. suis* type 2 infection. SDS-PAGE and Western blotting techniques were used in an earlier study to detect MRP and EF in culture supernatants, and on the basis of these results strains were categorized into three phenotypes: MRP+EF+, MRP+EF−, and MRP−EF− (Example 4). Also tested were 22 strains of *S. suis* serotypes 1 to 22 (15), 22 other streptococci, 20 bacterial strains of 15 different species, and one yeast (DLO-Central Veterinary Institute, Lelystad) (Table 6).

TABLE 6

List of microorganisms

| Group | Microorganisms | Microorganisms |
|---|---|---|
| A | *Streptococcus pyogenes humanis* | Other bacterial species: |
| B | *Streptococcus agalactiae* | *Staphylococcus aureus* |
| C | *Streptococcus equi* | *Staphylococcus epidermidis* |
| | *Streptococcus equisimilis porcine* | *Staphylococcus hyicus* |
| | *Streptococcus dysgalactiae* | *Aerococcus viridans* |
| | *Streptococcus zooepidemicus* | *Actinomyces pyogenes* |
| D | *Enterococcus faecalis* | *Escherichia coli* (3x) |
| | *Enterococcus faecium* | *Klebsiella oxytoca* |
| | *Enterococcus liquefaciens* | *Klebsiella pneumoniae* |
| | *Streptococcus bovis* (2x) | Micrococcus strain 3551 |
| | *Streptococcus zymogenes* | *Micrococcus Luteus* |
| E | Streptococcus group E | *Pasteurella multocida* (4x) |
| G | Streptococcus group G (2X) | |
| L | Streptococcus group L (2X) | *Proteus vulgaris* |
| p | Streptococcus group P | *Salmonella typhimurium* |
| Q | Streptococcus group Q | *Serratia liquefaciens* |
| | *Streptococcus milleri* III | Yeast: |
| | *Streptococcus sanguis* | *Cryptococcus laurentii* |
| | *Streptococcus uberis* | |

Culture condition and antigen preparation. A 1 day old colony of the bacteria grown overnight on Columbia blood agar base (code CM 331. Oxoid Ltd.) containing 6% horse blood was inoculated into Todd-Hewitt broth (code CM 189, Oxoid). After overnight growth at 37° C., cultures were centrifuged at 4000× g for 15 min. At 600 nm the optical densities of the 20 hour cultures were found to vary from 0.60 to 1.04. Some species had lower densities, these were *Bordetella bronchiseptica* (0.23). *Micrococcus species* (0.08 to 0.15). *Streptoccocus equinus* (0.36). *Cryptococcus neoformans* (0.05). Twofold serial dilutions of untreated culture supernatants were used as test samples in the two DAS-ELISAs. Culture supernatant of *S. suis* type 2 strain $D_{282}$ (MRP+EF) was concentrated and partially purified by ultra-filtration (type PM30 filters, Amicon Cooperation). It was diluted in phosphate-buffered saline (PBS) (136.89 mM NaCl. 2.68 mM KCl. 8.1 mM $Na_2HPO_4$. 2.79 mM $KH_2PO_4$. pH 7.2), to a final protein concentration of 75 μg/ml. This product was used as coating antigen for the selection of different monoclonals in the direct competition ELISA and for screening hybridoma culture supernatants in the indirect ELISA.

Preparation of polyclonal and monoclonal antibodies. Rabbit (Ra) polyclonal antibodies (PAb) directed against MRP and EF (Ra $K_{191}$) and three different MAbs directed against EF were prepared as described in Example 4. MAbs that specifically recognize MRP were prepared essentially the same as MAbs that recognize EF. Antigen production and immunization procedures in female BALB/c mice have been described (Example 4). Hybridoma cell lines were prepared as described (52). After 10 to 14 days, hybridoma culture supernatants were tested for antibodies against MRP in an indirect ELISA (see below). Hybridoma culture supernatants (diluted 1:2) were then tested on Western blots of culture supernatants of strain D-282 for antibodies directed against MRP. Bound MAb to the 136 kDa protein were visualized by using anti-mouse immunoglobulins conjugated to alkaline phosphatase and the substrate described below. Five supernatants were found positive, and the cells from these wells were cloned twice by limiting dilution in microtiter plates.

The five cell lines that were positive for anti-MRP antibodies and the three cell lines that were positive for anti-EF antibodies were used to produce ascites fluid in pristane-primed male BALB/c mice. MAbs directed against MRP and EF were purified from ascites fluid by ammonium sulphate precipitation (50% saturation) and dialysed against PBS. The five anti-MRP MAbs were designated: $MRP_1$ to $MRP_5$, the three anti-EF MABs were designated: $EF_1$ to $EF_3$. The immunoglobulin isotype of all MAbs was $IgG_1$ and was determined by double immunodiffusion with mouse isotype-specific antisera (Nordic) in gels of 1% agarose in PBS. The PAbs and MAbs were stored at −20° C.

Indirect ELISA for screening hybridoma culture supernatants. Polystyrene microtiter plates (Greiner, Nürtingen, Germany) were coated for 16 h at 37° C. with the solution of concentrated and dialysed culture supernatant of strain D-282 (see above). They were then diluted in PBS, pH 7.2 (75 μg/ml protein). Twofold dilutions of hybridoma culture supernatants were added to the wells according to the procedure described by Van Zijderveld et al. (51). After the plates were washed, antimouse immunoglobulins (diluted 1:500) conjugated with horse radish peroxidase (HRPO, Nordic) were added. After incubation for 1 h at 37° C. and five washings, the bound HRPO-antibody was then detected by the addition of substrate, 0.1% (w/v) solution of recrystallized 5-aminosalicylic acid (5-AS) (Merck) in 0.01M phosphate buffer, pH 5.95, containing 0.01M sodium EDTA to which $H_2O_2$ had been added, immediately before use to an end concentration of 0.005% (wt/vol). After 2 h incubation at room temperature, the absorbance was measured at 450 nm with a Titertek Multiskan photometer (Flow Labs).

Direct competition ELISA. MAbs were selected with the direct competition ELISA and were used to develop the MRP and EF double antibody sandwich (DAS) ELISAs. Purified anti-MRP and anti-EF MAbs and rabbit PAbs were conjugated to HRPO (Boehringer Mannheim, Germany) with the periodate method of Wilson and Nakane (49). Conjugated immunoglobulins were stored at −20° C. in 50% glycerol. Conjugate solutions were made in PBS-Tw containing 5% fetal calf serum and 0.5% sodium chloride. 50 μl of nonconjugated anti-MRP MAbs in serial twofold dilutions (range 1:20 to 1:10,240) were added to the wells of polystyrene microtiter ELISA plates (Greiner) that had been coated with the culture supernatant of strain $D_{282}$ that had been partially purified in PBS (75 μg/ml protein). The plates were then incubated for 30 min at 37° C. To allow the nonconjugated MAb to compete with the MAb conjugates, 50 ml of the optimal dilution of each of the five anti-MRP MAbs conjugated to HRPO were added. After incubation for 1 h at 37° C., plates were washed and the bound HRPO antibody was then detected by the addition of the substrate 5-AS $H_2O_2$ as described above. After 2 h incubation at room temperature, the absorbance was read. The titers of competition were expressed as the highest dilution showing an $A_{450}$ of 50% of the mean absorbance of wells to which only conjugate was added. The epitope specificity of the three anti-EF MAbs was determined with a competition ELISA similar to the one described for the anti-MRP MAbs.

SDS-PAGE and Western blotting techniques. Culture supernatants of the 22 *S. suis* serotypes and the other microrganisms (Table 6) were separated by SDS-PAGE on 6% polyacrylamide. For Western blot analysis, the proteins were electroblotted onto nitrocellulose by the Multiphor II Nova Blot system according to the recommendations of the manufacturer (Pharmacia LKB). The blots were probed with a 1:300 dilution of mouse MAb. Bound MAbs were visualized with a 1:1000 dilution of anti-mouse immunoglobulins conjugated with alkaline phosphatase (Zymed).

RESULTS

Direct competition ELISA. The five anti-MRP clones and the three anti-EF clones were tested for competition. Some anti-MRP clones competed with each other. The five anti-MRP MAbs were directed against at least three different epitopes: the first was recognized by $MRP_1$ and $MRP_2$, the second by $MRP_3$, and the third by $MRP_4$ and $MRP_5$. Because all three anti-EF clones competed, they are probably directed against the same epitope.

MRP double antibody sandwich ELISA. In an MRP DAS-ELISA using $MRP_3$ as catching antibody and HRPO-$MRP_1$ as conjugate, each well of the polystyrene microtiter ELISA plates was coated with 100 μl containing 2.3 μg $MRP_3$ per well in 0.05M carbonate buffer, pH 9.6. After adsorption for 16 h at 37° C., coated plates were used immediately or stored at −20° C. Twofold serial dilutions of 100 μl culture supernatants, ranging from 1:1 to 1:128 in PBS containing 0.05% (wt/vol) Tween 80, of strains to be tested, were added to the wells. After 1 h incubation at 37° C., plates were washed five times with 0.05% Tween 80 in tap water, and 100 μl 7.2. was added to each well. Using checker-board titrations, the optimal dilution of catching antibody and conjugate was determined. After 1 h incubation at 37° C., the substrate 5-AS $H_2O_2$ was added as described above. Wells with an $A_{450} \geq 0.2$ were scored positive. To each plate a positive control was added, consisting of 100 μl of undiluted culture supernatant of the virulent S. suis type 2 strain 4005 (MRP+EF+). A negative control was also added, consisting of 100 μl of undiluted culture supernatant of the non-virulent strain T-15 (MRP–EF–) (43).

The MRP DAS-ELISA was used to test 179 strains of S. suis type 2 belonging to the three phenotypes MRP+EF+, MRP+EF–, and MRP–EF–, as was previously determined by SDS-PAGE and Western blot. Most strains scored in the ELISA the same as they did in the Western blot (Table 7). All MRP+EF+ strains were MRP-positive in the ELISA. One MRP+EF– strain scored false negative. Three of the MRP–EF– strains (6%) scored false positive. The sensitivity (TP/TP+FN) (TP=true positive, FN=false negative) of the MRP DAS-ELISA was 99% (130 out of 131 strains), the specificity (TN/TN+FP) (TN=true negative, FP=false positive) was 94% (45 out of 48 strains), and the predictive value (TP/TP+FP) was 98% (130 out of 133 strains). The MRP DAS-ELISA discriminated well between the MRP-positive and MRP-negative strains of S. suis type 2.

TABLE 7

Results of 179 strains of S. suis type 2 (three phenotypes) tested in the MRP and EF DAS-ELISAs.

| phenotype | MRP DAS ELISA | | EF DAS ELISA | |
| --- | --- | --- | --- | --- |
| | No. strains + | No. strains – | No. strains + | No. strains – |
| MRP+EF+ | 92 (100%) | 0 | 92 (100%) | 0 |
| MRP+EF– | 38 (97%) | 1 (3%) | 0 | 39 (100%) |
| MRP–EF– | 3 (6%) | 45 (94%) | 0 | 48 (100%) |

Titration curves of culture supernatants of strains belonging to three phenotypes of S. suis type 2, after testing in the MRP DAS-ELISA, were recorded. The mean (± standard deviation) of the absorbances obtained from the undiluted culture supernatants of the 92 MRP+EF+ isolates was 1.2259 (±0.1165), the mean absorbance of the 39 MRP+EF– isolates was 1.2129 (±0.2076), and the mean absorbance of the 48 MRP–EF– isolates was 0.1180 (±0.2546). Therefore plates can be read visually instead of having to be measured photometrically to discriminate MRP-positive strains (phenotypes MRP+EF+ or MRP+EF–) from MRP-negative strains (phenotype MRP–EF–).

Culture supernatants of 18 of the 21 reference S. suis strains of other serotypes had absorbances lower than 0.2. Three serotypes were positive and had the following absorbance values: undiluted culture supernatant of serotype 3 had $A_{450}$=0.731; culture supernatant of serotype 5 had $A_{450}$=0.587, and culture supernatant of serotype 15 (former Lancefield group T) had $A_{450}$=0.516. These serotypes were also positive in the Western blot; $MRP_3$ apparently recognized proteins of higher molecular weight than 150 kDa in the culture supernatants of these serotypes. Absorbances of all other microorganisms listed in Table 6 were <0.2.

EF Double Antibody Sandwich ELISA. In a DAS ELISA that recognizes a specific antigen in the test sample, two different MAbs were used, one as catching antibody and the other as conjugate, and each recognizing different epitopes on the antigen, as was done for the MRP DAS-ELISA. In the Western blot the EF MAbs recognize a high molecular form of EF (>150 kDa) in the culture supernatants of all strains belonging to the MRP+EF–phenotype (Example 4). Therefore it is unlikely that an ELISA with $EF_2$ as catching antibody can discriminate between MRP+EF+ and MRP+EF– strains. Moreover, because the three EF MABs blocked each other, we had to use $EF_2$ as catching antibody and the polyclonal rabbit serum ($K_{191}$) as conjugate. Some ELISAs were tested using $EF_1$ as catching antibody and $EF_2$ or $EF_3$ as conjugates, and indeed these MAbs blocked each other completely.

The procedure of the EF DAS-ELISA was essentially as that described for the MRP DAS-ELISA. Each well of the microtiter ELISA plates was coated with 100 ml containing 3.3 μg of $EF_2$ in 0.05M carbonate buffer, pH 9.6. After adsorption, coated plates were used immediately or stored at –20° C. Twofold serial dilutions of 100 μl culture supernatants ranging from 1:1 to 1:128 were used. After incubation and washings, 100 μl containing 2.7 μg polyclonal Ra $K_{191}$ HRPO conjugate in PBS, pH 7.2, was added to each well. After 1 h incubation at 37° C., the plates were developed with substrate 5-AS $H_2O_2$ as described above. Wells with an $A_{450} \geq 0.4$ were scored positive. The same controls as mentioned above were used on each plate.

The 179 S. suis type 2 strains with a predetermined protein profile were tested in the EF DAS-ELISA. Surprisingly, none of the 39 MRP+EF– strains scored positive in this ELISA, whereas all 92 MRP+EF+ strains did (Table 7). All 48 MRP–EF– strains were negative in the EF DAS-ELISA. Since no other false positive or false negative results were detected, the EF DAS-ELISA apparently discriminated reliably between the high and the low molecular form of EF, and hence between S. suis type 2 strains belonging to the MRP+EF+ and MRP+EF– phenotypes.

Since the direct competition ELISA had shown that the three anti-EF MAbs blocked each other, MAb $EF_2$ was used as catching antibody and the polyclonal Ra $K_{191}$ serum as conjugate. Streptococcus suis type 2 strains belonging to the MRP+EF– phenotype, however, produce a high-molecular weight (>150 kDa) form of EF (example 4). Because MAb $EF_2$ does not discriminate between the 110-kDa EF and this high-molecular weight form in the Western blot, it was unlikely to do so in the EF DAS-ELISA. Surprisingly Mab $EF_2$ captured the 110-kDa EF in the culture supernatant of all MRP+EF+ strains but apparently not the higher-molecular weight form in the MRP+EF– strains (Table 7). Some MRP–EF– strains gave signals between 0.2 and 0.4, which were still lower than 50% of the maximal absorbance values and thus not high enough to be interpreted as positive. Treating the culture supernatants with SDS before blotting may uncover epitopes of the higher-molecular weight form of EF that are not accessible to the $EF_2$ MAb in its undenaturated form. Because all MRP+EF– strains and other S. suis serotypes showed no false negative or false positive reactions in this ELISA, the sensitivity and specificity of the test were considered to be 100%.

Titration curves of culture supernatants of strains belonging to three phenotypes of S. suis type 2 were recorded after testing in the EF DAS-ELISA. The mean (± standard deviation) of the absorbances obtained from the undiluted culture supernatants of the 93 MRP+EF+ strains was 0.8204 (±0.149), the mean absorbance of the 39 MRP+EF– strains was 0.1551 (±0.046), and the mean absorbance of the 48 MRP–EF– strains was 0.1061 (±0.0371). Thus, as for the MRP DAS-ELISA, plates can be read visually to discriminate between EF-positive strains (phenotype MRP+EF+) and EF-negative strains (phenotypes MRP+EF– or MRP–EF–).

None of the 21 reference S. suis strains with a serotype other than type 2 were EF-positive in the ELISA. Some other bacterial species had positive absorbance values: Streptococcus Lancefield group G ($A_{450}$=0.445), group L ($A_{450}$=0.348), Streptococcus equi ($A_{450}$=0.671), and Staphylococcus aureus ($A_{450}$=0.718).

EXAMPLE 7

Differentiation between pathogenic and non-pathogenic strains of *Streptococcus suis* type 2 by using polymerase chain reaction (PCR).

MATERIALS AND METHODS.

Bacteria and growth conditions. Thirteen strains of *S. suis* type 2 were selected to examine whether the Polymerase Chain Reaction (PCR) method (36) could be useful to differentiate between the three phenotypes of *S. suis* type 2. Pathogenicity and the expression of the MRP and EF proteins of these strains were determined in Examples 4 and 5. Strains were grown overnight at 37° C. on Columbia blood agar base (code CM 331, Oxoid) containing 6% horse blood. *S. suis* type 2 colonies were inoculated in 10 ml Todd-Hewitt broth (code CM 189, Oxoid), and grown overnight at 37° C.

DNA Isolations. DNA of overnight grown cultures was isolated as described by Maniatis et. al (28). DNA was diluted to 10 ng/μl in distilled water before use in the PCR.

Clinical specimens. Nose swabs and tonsillar tissues were obtained post mortem from sows at slaughter. Nose swabs were inoculated on blood plates. *S. suis* type 2 strains were isolated from tonsils as described before (27).

Sample preparation. Clinical specimens for the PCR were prepared by the method described by Boom et. al (4), with some minor modifications: The specimens were added to 900 μl L6 lysis buffer plus 40 μl diatom earth solution in an Eppendorf tube [L6 buffer is 100 ml 0.1M TRIS HCl (pH 6.4) plus 120 g guanidine (iso)thiocyanate (GuSCN, Fluka cat nr. 50990) plus 22 ml 0.2M EDTA (pH 8.0) plus 2.6 g Triton X-100. Diatom earth solution is 10 g Diatom earth (Janssen Chimica Cat. nr. 17.346.80) in 50 ml distilled water plus 500 μl 32% (w/v) HCl]. The clinical specimens were incubated overnight in L6 buffer in the dark at room temperature. 150 μl of the solution was pipetted in wells of microtiter plates containing Durapore membranes (Multiscreen MAHV N45, Millipore). The microtiter plate was put on the vacuum manifold (MAVM 09600, Millipore), and the samples were washed 5 times with 200 μl L2 washing solution (L2 buffer is 100 ml 0.1M Tris-HCl (pH 6.4) plus 120 g GuSCN), 5 times with 200 μl 70% ethanol, and once with 200 μl aceton. The filters were not allowed to run dry between the wash steps. The bottom of the microtiter plate was dried on a tissue and the samples were dried completely for 15 minutes at 56° C. 75 μl PCR buffer (see below) was added to the individual wells. The plate was incubated for 15 minutes at 56° C. The microtiter plate was again put on the vacuum manifold, with a standard microtiter plate (Micronic) beneath the Durapore plate. Vacuum was applied, and the PCR buffer, containing the DNA was collected in the lower microtiter plate, whereas the diatom earth remained on the Durapore filters.

PCR assay. The PCR contained 10 ng purified DNA or 25 μl clinical specimen in a total volume of 50 μl. The reaction mixtures contained 10 mM Tris-HCl (pH 9.0), 2 mM $MgCl_2$, 50 mM KCl, 0.01% gelatin, 0.2 mM of each of the four deoxynucleotide triphosphates, 1 μM of each of the four primers and 0.5 U of Amplitaq polymerase (Perkin Elmer Cetus, Norwalk, Conn.), and was overlaid with 2 drops of paraffine oil. DNA amplification was carried out in a Perkin Elmer Thermal Cycler for 25 or 40 cycles: 1 minute 94° C., 1 minute 55° C., and 2 minutes 72° C. Ten to 20 μl of the amplified DNA was analysed on a 1.5% agarose gel, that contained ethidium bromide.

PCR primers. The sequences of the oligonucleotides used in the PCR were: p15. SEQ ID NO 3 base pairs 1403–1425: 5'-GGT ATA CCT TGC TGG TAC GGT TC -3', p16: SEQ ID NO: 3 base pairs 1914–1934: 5'-AGT CTC TAC AGC TGT AGC TGG -3'(which correspond to the complement), p-34: SEQ ID NO: 2 base pairs 2890–2908: 5'-GTT GAA AAC AAA GCA TTC G -3', and p-35: SEQ ID NO 2 base pairs 3229–3249: 5'- CTT CGA CAA AAT GTC AGA TTC -3'. The oligonucleotides p-15 and p-16 correspond to the indicated positions in the *S. suis* type 2 mrp gene (Example 3, SEQ ID NO:3). The oligonucleotides p-34 and p-35 correspond to the indicated positions and in the *S. suis* type 2 ef* gene (Example 2, SEQ ID NO:2). Primers were synthesized on an Applied Biosystem synthesizer type 381A following the manufacturers protocol.

RESULTS

Specificity of PCR. Within the mrp and ef* genes (cf. Examples 3 and 2), two regions (designated as m-VI and e-V) were determined that could be used to differentiate between the three phenotypes of *S. suis* type 2 strains (see also Example 8). Primers based on the m-VI region (p-15 and p-16), and the e-V region (p-34 and p-35) were used in a PCR. The primers p-15 and p-16 amplified a 532 bp fragment in the m-VI region. The primers p-34 and p-35 amplified a 360 bp fragment in the e-V region. Chromosomal DNA of 4 $MRP^+EF^+$, 4 $MRP^+EF^*$ and 5 $MRP^-EF^-$ strains was used in a PCR with these primers (see FIG. 15). After 25 cycli the amplified fragments were analysed on an agarose gel. A 532 bp fragment was amplified from DNA of $MRP^+EF^+$ strains. A 532 bp fragment as well as a 360 bp fragment were amplified from DNA $MRP^+EF^*$ strains. In contrast, neither the 532 bp nor the 360 bp fragment was amplified from DNA of $MRP^{-EF-}$ strains. These data show that this PCR can be used to differentiate between the three phenotypes of *S. suis* type 2.

The phenotypes of 82 strains of *S. suis* type 2, isolated from the tonsils of 37 healthy sows at slaughter, were determined by Western blotting (Example 4), ELISA (Example 6), hybridization experiments with DNA probes m-VI and e-V (Example 8), and by PCR. 79 strains, isolated from 36 of the 37 sows were classified identical by the four methods (96.3%). 3 strains, isolated from one sow, were classified as $MRP^+EF^*$ by the PCR and DNA hybridization experiments and as $MRP^-EF^-$ by Western blotting and ELISA. These results indicate that the PCR is a useful alternative to determine the phenotype of a *S. suis* type 2 strain.

Sensitivity of PCR. Purified chromosomal DNA of a $MRP^+EF^*$ *S. suis* type 2 strain was diluted in distilled water and used directly in the PCR. After 40 cycli of PCR, 25 fg DNA was detected. This indicates that DNA of 14 cells, after amplification by PCR, could be detected on an agarose gel, based on data that a Streptococcal cel contains about 1.75 fg DNA (35). The sensitivity of the PCR on whole cells was determined. Therefore, $MRP^+EF^*$ cells were diluted in phosfate buffered saline (PBS (pH 7.2); 137 mM NaCl, 2.7 mM KCl, 8.1 mM $Na_2HPO_4$, 2.8 mM $KH_2PO_4$) and prepared for PCR as described above. Amplified fragments could still be detected in samples that contained about 50 cells prior to the PCR (40 cycli).

The PCR can be used directly on clinical material. Serial dilutions of *S. suis* type 2 cells were added to nose swabs. It was found that amplified fragments can still be detected in samples that contain about 50 cells prior to the PCR.

EXAMPLE 8

Differentiation between pathogenic and non-pathogenic strains of S. suis type 2 using DNA probes.

MATERIALS AND METHODS

Bacteria. Thirteen strains of S. suis type 2 (4 MRP+EF* strains and 5 MRP−EF− strains) were selected to examine whether regions of the mrp, ef, and ef* genes could be useful to differentiate between the three phenotypes of S. suis type 2. Except for strain 16, pathogenicity of these strains was tested in an infection experiment of piglets (Example 5).

170 strains of S. suis type 2 were obtained from three sources: From organs of diseased pigs (103 strains), from tonsils of healthy pigs at slaughter (40 strains) and from human patients (27 strains). Reference strains of S. suis serotypes 1 to 22 (15), 21 other Streptococci species and 45 other bacterial strains (38 different species, DLO Central Veterinary Institute, Table 8) were used to test the specificity of the mrp and ef probes.

Media. E. coli JM101 strains were grown in LB broth (30). Ampicillin was added as needed to a final concentration of 50 μg/ml. All other bacterial strains were grown overnight at 37° C. on Columbia blood agar base (code CM 331, Oxoid) containing 6% horse blood. Overnight grown colonies were incubated in 10 ml Todd-Hewitt broth (code CM 189, Oxoid), and grown overnight at 37° C.

DNA isolations and manipulations. Chromosomal DNA isolations and routine DNA techniques were performed as described by Maniatis et al (28). Crude lysates were made as follows: overnight grown cultures were centrifuged at 4000× g for 10 minutes, and the pellet fraction was resuspended in 500 to 1000 μl TEG-lysozym buffer (25 mM TRIS.Cl pH 8.0, 10 mM EDTA, 50 mM glucose and 1 mg/ml lysozym). After 30 minutes at 25° C., the samples were used in the dot-blot assay.

Probes. The plasmids pMR11, pEF2-19 and pEF17-7 (cf. Examples 1, 2, 3) were used to generate subclones into pKUN19 (24). Fragments of appropriate subclones were isolated from preparative agarose gels with the gene-clean kit (Bio 101 Inc., La Jolla, USA). Purified fragments were subsequently labeled with $\alpha$-$^{32}$P dCTP (3000 Ci/mMol, Amersham) with the random primed labeling kit (Boehringer GmbH) following the manufacturers protocol and used as probes.

Southern hybridizations. Chromosomal DNA of the 13 selected S. suis 2 strains (1 μg DNA) was spotted on Gene-screen nylon membrane (New-England Nuclear Corp., Boston, USA). The membranes were incubated with the $^{32}$P-labeled mrp and ef probes as recommended by the manufacturer. After overnight hybridization, the filters were washed twice with 2× SSC for 5 minutes at room temperature, and twice with 0.1× SSC plus 0.5% (SDS) for 30 minutes at 65° C. (1× SSC=0.15M NaCl plus 0.015M Sodium Citrate). For the group of 170 S. suis 2 strains, the 22 reference strains of S. suis type 1 to 22, and the group of other Streptococci and other bacteria, 20 μl of a DNA or crude lysate sample was dotted on Zeta probe nylon membrane (Biorad) with a dot blot apparatus (Bethesda Research Laboratories).

The membranes were incubated with the $^{32}$P-labeled mrp and ef probes as recommended by the manufacturer. After overnight hybridization, the membranes were washed twice in 40 mM Na phosphate buffer, pH 7.2 plus 5% SDS plus 1 mM EDTA for 30 minutes at 65° C. and twice in 40 mM Na phosphate buffer, pH 7.2 plus 1% SDS plus 1 mM EDTA for 30 minutes at 65° C. All (pre)hybridizations were carried out in a hybridization oven (Hybaid).

RESULTS

Mrp probes. Chromosomal DNA of the 3 phenotypes of S. suis type 2 was hybridized to different regions of the mrp gene. Six different mrp probes were used (schematically shown in FIG. 14a). The EcoRI-SnaBI fragment, m-I, contained the entire mrp encoding region. The m-II, m-III, m-IV and m-V probes contained different regions of the mrp gene (see FIG. 16). The MRP+EF+ and the MRP+EF* strains strongly hybridized with all mrp probes. In addition, the m-I, m-II, m-IV and m-V probes strongly hybridized with 4 of the 5 MRP−EF− strains. One MRP−EF− strain (strain 25) did not hybridize with any of the mrp probes. These data indicate that 4 MRP−EF− strains contained large regions homologous to the mrp gene of strain D282, whereas strain 25 lacked the entire mrp gene. These 4 MRP−EF− strains, however, hybridized only weakly with probe m-III, indicating that only a small part of probe m-III was homologous to their DNA. A probe m-VI was constructed by removing 385 bp at the 5', and 325 bp at the 3' ends of probe m-III. The 5 MRP−EF− strains did not hybridize at all with probe m-VI, indicating that these strains lacked the region homologous to the m-VI probe. Therefore, probe m-VI can be used to differentiate between MRP+ and MRP− strains.

Ef and ef* probes. Chromosomal DNA of the 3 phenotypes S. suis type 2 was hybridized to different regions of the ef gene. Four different ef probes (schematically shown in FIG. 14b) were used. All MRP+EF+ and MRP+EF* strains and 1 MRP−EF− strain hybridized with all ef probes. In contrast, 4 MRP−EF− strains did not hybridize with any of the ef probes. These data indicate that most of these MRP− EF− strains lacked the entire region homologous to the ef gene, whereas 1 MRP−EF− strain seemed to contain the entire region homologous to the ef gene. Therefore, the probes e-I to e-IV could not been used to differentiate between the 3 phenotypes.

Figure 14:
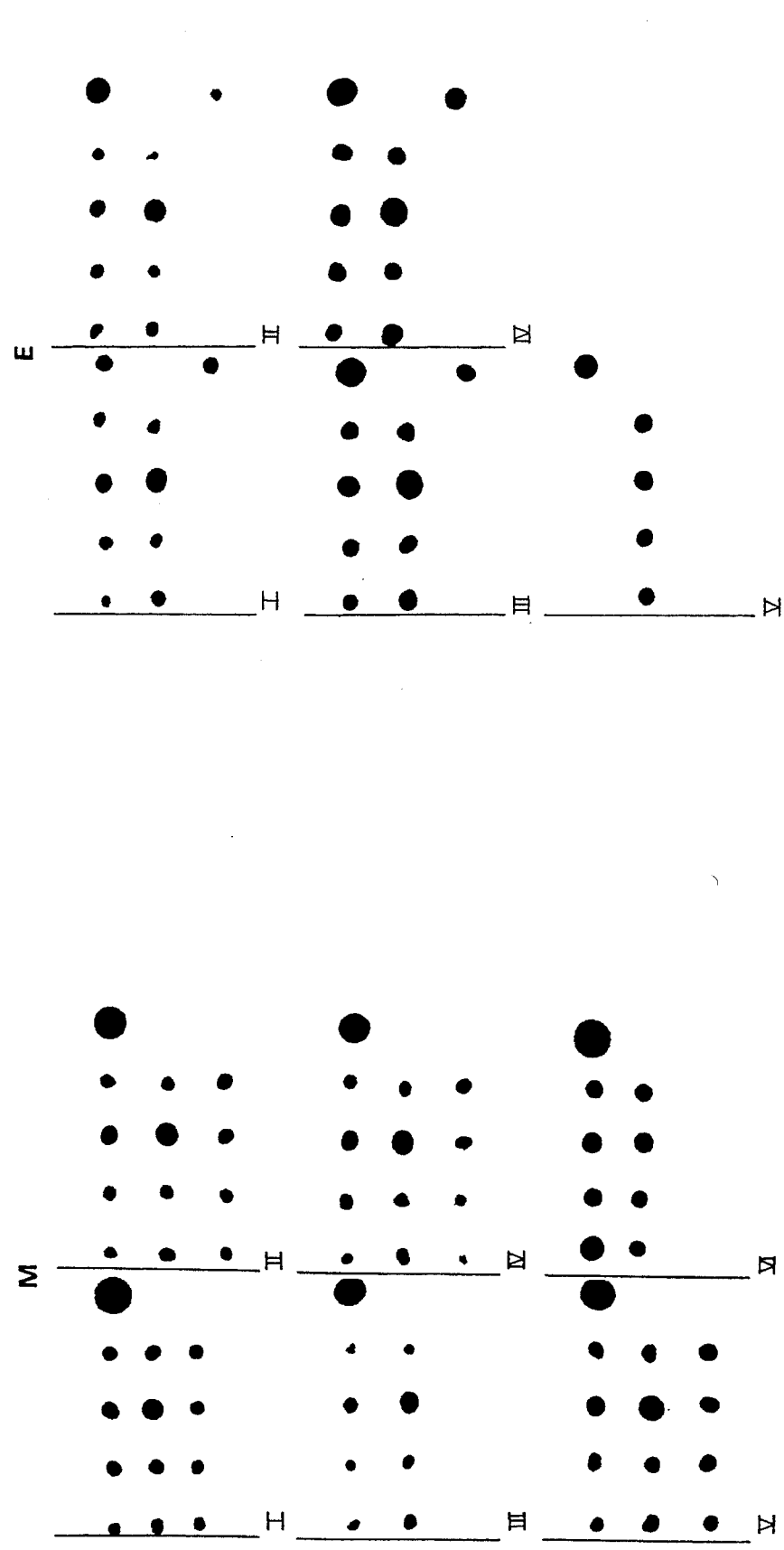

Since the gene encoding the EF* proteins contain a DNA fragment which is absent in the gene encoding the EF protein, part of this extra DNA was selected as a probe (FIG. 14c, probe e-V). Probe e-V hybridized with all MRP+EF* strains. On the contrary, none of the MRP+EF+ and MRP− EF− strains hybridized with the e-V probe. These data suggest that the MRP+EF+ and MRP−EF− strains lacked the region homologous to e-V. Probe e-V is thus specific for MRP+EF* strains.

Therefore, if m-VI and e-V are used in complementary hybridization studies, a differentiation between the three phenotypes of S. suis type 2 will be possible. If S. suis type 2 strains hybridize with probe m-VI and e-V, these strains belong to the MRP+EF* phenotype. If S. suis type 2 strains hybridize with m-VI but not with e-V, these strains belong to the MRP+EF+ phenotype, and finally if strains do not hybridize with m-VI and e-V, these strains belong to the MRP−EF− phenotype.

The mrp, ef and ef* probes were tested on 170 other strains of S. suis type 2. 88 strains had a MRP+EF+ phenotype, 37 strains a MRP+EF* phenotype and 45 strains had a MRP−EF− phenotype. In accord with the data presented above, all MRP+EF+ strains hybridized with the probes m-I to m-VI and e-I to e-IV, but none hybridized with probe e-V. Moreover, all the 37 MRP+EF* strains hybridized with all the probes. Only two of the 45 MRP−EF− strains, however, hybridized with probe m-VI and e-V and would therefore wrongly be classified as MRP+EF* strains. Therefore, by using m-VI and e-V, the phenotype of a S. suis type 2 strain can be predicted with a very high probability (168/170; 98.8%).

Specificity of the m-VI and e-V probes. DNA of the reference strains of S. suis serotype 1 to serotype 22 was tested for hybridization with probes m-VI and e-V. It was found that *S. suis* type 2 (strain 735), 4, 5 and 14 hybridized with the m-VI probe and that type ½, 2, 4, 5, 6, 14 and 15 hybridized with the e-V probe. These data suggest that the mrp and ef genes are not specific for *S. suis* type 2, but that homologous sequences are present in several serotypes. Based on these data, serotypes 2, 4, 5 and 14 would be classified as MRP$^+$EF* strains, whereas serotypes ½, 6 and 15 would be classified as MRP$^-$EF$^-$ strains.

Chromosomal DNA from swine pathogens and several common bacteria was tested with the probes m-I, m-VI, e-III and e-V. The species tested are listed in Table 8. Although some species hybridized with probe m-I (*Escherichia coli*, *Klebsiella oxytoca*, *K. pneumoniae* and *Salmonella typhimurium*), none hybridized with the probes m-VI, e-III and e-V. These data shown that although in some species parts of the mrp genes are found, the probes m-VI and e-V are specific for *S. suis*. Hence, the probes m-VI and e-V have potential diagnostic value.

TABLE 8

List of other species on which the probes were tested for specificity.

Streptococcus species

| | |
|---|---|
| *S. agalactiae* | *S. equi* |
| *S. equisimilis porcine* | *S. zooepidemicus* |
| *S. dysgalactiae* | *Enterococcus faecalis* |
| *E. liquefaciens* | *E. zymogenes* |
| *E. faecium* | *S.* group E |
| *S. milleri* III | *S. bovis* |
| *S. pyogenes humanis* | *S. uburis* |
| *S. animale* G | *S.* group G |
| *S.* group L biotype I | *S.* group L biotype II |
| *S.* group P | *S.* group Q |
| *S. sanguis* | |

Other Bacteria

| | |
|---|---|
| *Actinobacillus pleuropneumoniae* | *Actinobacillus viridans* |
| *Actinobacillus suis* | *Aeromonas hydrophila* |
| *Actinomyces pyogenes* | *Bacillus licheniformis* |
| *Bacillus cereus* | *Bordetella bronchiseptica* |
| *Bacillus subtilis* | *Brucella suis* biotype II |
| *Brucella suis* biotype I | *Campylobacter faecalis* |
| *Campylobacter coli* | *Candida albicans* |
| *Campylobacter jejuni* | *Erysipelothrix rhusiopathiae* |
| *Clostridium perfringens* A non-toxic | *Klebsiella oxytoca* |
| *Clostridium perfringens* A toxic | *Listeria monocytogenes* |
| *Escherichia coli* | *Micrococcus luteus* |
| *Haemophilus parasuis* | *Mycoplasma hyopneumoniae* |
| *Klebsiella pneumoniae* | *Mycoplasma hyosynoviae* |
| *Micrococcus* strain 3551 | *Pasteurella multocida* |
| *Mycobacterium avium* serovar2 | *Salmonella typhimurium* |
| *Mycoplasma hyorhinis* | *Staphylococcus aureus* |
| *Pseudomonas aeruginosa* | *Staphylococcus hyicus hyicus* |
| *Pasteurella vulgaris* | |
| *Serratia liquefaciens* | |
| *Staphylococcus epidermidis* | |
| *Yersinia enterocolitica* | |

LITERATURE REFERENCES

1. Arends, J. P., and H. C. Zanen. 1984. Proc. 9th Lancefield Int. Symp. Streptococci Streptococcal Dis., p. 343–344.
2. Arends, J. P., and H. C. Zanen. 1988. Meningitis caused by *Streptoccus suis* in humans. Rev. Infect. Dis., 10: 131–137.
3. Arends, J. P., N. Hartwig, M. Rudolphy, and H. C. Zanen. 1984. Carrier rate of *Streptococcus suis* capsular type 2 in palatine tonsils of slaughtered pigs. J. Clin. Microbiol. 20: 945–947.
4. Boom, R., C. J. A. Sol, M. M. M. Salimans, C. L. Jansen, P. M. W. Wertheim-van Dillen, and J. van der Noordaa. 1990. Rapid and simple method for purification of nucleic acids, J. Clin. Microbiol. 28: 495–503.
5. Breton, J., W. R. Mitchell, and S. Rosendal. 1986, *Streptococcus suis* in slaughter pigs and abbatoir workers. Can. J. Vet. Res., 50: 338–341.
6. Clifton-Hadley, F. A. 1983. *Streptococcus suis* type 2 infections. Br. Vet. J. 139: 1–5.
7. Clifton-Hadley, F. A., T. J. L. Alexander, M. R. Enright, and J. Guise. 1984. Monitoring herds for *Streptococcus suis* type 2 by sampling tonsils of slaughter pigs. Vet. Rec. 115: 562–564.
8. Clifton-Hadley, F. A., T. J. L. Alexander, I. Upon, and W. P. H. Duffus. 1984. Further studies on the subclinical carrier state of *Streptococcus suis* type 2 in pigs. Vet. Rec., 114: 513–518.
9. Driessen, A. M. J., W. de Vrij, and W. N. Konings. 1985. Incorporation of beef heart cytochrome c oxidase as a proton-motive-force generating mechanism in bacterial membrane vesicles. Proc. Natl. Acad. Sci. USA 82: 7555–7559.
10. Fahnestock, S. R., P. Alexander, J. Nagle and D. Filpula. 1987. Gene for an immunoglobulin-binding protein from a group G Streptococcus. J. Bacteriol. 167: 870–880.
11. Ferretti, J. J., R. R. B. Russell, and M. L. Dao. 1989. Sequence analysis of the wall-associated protein precursor of *Streptococcus mutans* antigen A. Mol. Microbiol. 3: 469–478.
12. Fischetti, V. A., V. Pancholi, and O. Schneewind. 1990. Conservation of a hexapeptide sequence in the anchor region of surface proteins from Gram-positive cocci. Mol. Microbiol. 4: 1603–1605.
13. Frithz, E., L-O. Heden and G. Lindahl. 1989. Extended sequence homology between IgA receptor and M proteins in *Streptococcus pyogenes*. Mol. Microbiol. 3: 1111–1119.
14. Gogolewski, R. P., Cook, R. W. and O'Connel, C. J., 1990. *Streptococcus suis* serotypes associated with disease in weaned pigs. Austr. Vet. J., 67: 202–204.
15. Gottschalk, M., R. Higgins, M. Jaques, K. R. Mittal, and J. Henrichsen. 1989. Description of 14 new capsular types *Streptococcus suis*. J. Clin. Microbiol., 27: 2633–2636.
16. Guss, B., M. Uhlen, B. Nilsson, M. Lindberg, J. Sj öquist, and J. Sjödahl. 1984. Region X, the cell-wall-attachment part of staphylococcal protein A. Eur. J. Biochem. 138: 413–420.
17. Hager, P. W., and J. C. Rabinowitz. 1985. Translational specificity in *Bacillus subtilis*. In: The Molecular Biology of the Bacilli. Dubnau, D. A. (ed.). New York, Academic Press. pp 1–32.
18. Ham-Hoffies, A. M., L. A. M. G. van Leengoed, and A. Hoogendoorn. 1986. Calibration of a conducting counter in determining haematological values in blood sample of various animals. Proc. IVth Int. Symp. of Vet. Lab. Diagn. Amsterdam. p. 692–693.
19. Higgins, R., M. Gottschalk, K. R. Mittal, and M. Beaudoin. 1989. *Streptococcus suis* infections in swine. A sixteen month study. Can. J. Vet. Res., 54: 170–173.
20. Hollingshead, S. K., V. A. Fischetti, and J. R. Scott. 1987. The complete nucleotide sequence of type 6M protein of the group A Streptococcus: repetitive structure and membrane anchor. J. Biol. Chem. 261: 1677–1686.
21. Hommez, J., L. A. Devriese, J. Henrichsen, and F. Castryck. 1986. Identification and characterisation of *Streptococcus suis*. Vet. Microb., 16: 349–355.
22. Jaarsveld, B. C., E. van Kregten, R. G. van Kesteren, M. Rozenberg-Arska, and A. K. M. Bartelink. 1990. Fulminante sepsis door *Streptococcus suis*. Ned. Tijdschr. Geneesk., 134: 1462–1464.
23. Kamp, E. M., and T. G. Kimman. 1988. Induction of nasal turbinate atrophy in germ-free pigs, using *Pasteurella multocida* as well as bacterium-free crude and purified dermonecrotic toxin of *P. multocida*. Am. J. Vet. Res. 49: 1844–1849.

24. Konings, R. N. H., E. J. M. Verhoeven, and B. P. H. Peeters. 1987. pKUN vectors for the separate production of both DNA strands of recombinant plasmids. Methods Enzymol. 153: 12–34.

25. Kyte, J., and R. F. Doolittle. 1982. A simple method for displaying the hydrophatic character of a protein. J. Mol. Biol. 157: 105–132.

26. Laemmli, U. K. 1970. Cleavage of structural proteins during the assembly of the head of T4. Nature 227: 680–685.

27. leengoed, L. A. M. G. van, U. Vecht, and E. R. M. Verheyen. 1987. *Streptococcus suis* type 2 infections in pigs in the Netherlands (part two). Vet. Quart. 9: 111–117.

28. Maniatis, T., E. F. Fritsch, and J. Sambrook. 1982. Molecular cloning: A laboratory manual. Cold Spring Harbor Laboratory, Cold Spring Harbor, N. Y. Sambrook, J., E. F. Fritsch, and T. Maniatis. 1989. Molecular cloning. A laboratory manual. Second edition. Cold Spring Harbor Laboratory Press. Cold Spring Harbor N.Y.

29. Messing, J. 1979. A multipurpose cloning system based on the single-stranded DNA bacteriophage M13. Recombinant DNA Technical Bulletin. NIH Publication no 79–99, 2, no 2, 43–48.

30. Miller, J. 1972. Experiments in Molecular Genetics. Cold Spring Harbor Laboratory. Cold Spring Harbor N.Y.

31. Moreau, A., R. Higgins, M. Bigras-Poulin, and M. Nadeau. 1989. Rapid detection of *Streptococcus suis* serotype 2 in weaned pigs. Am. J. Vet. Res., 50: 1667–1671.

32. Morissey, J. H. 1981. Silver stains for proteins in polyacrylamide gels: A modified procedure with enhanced uniform sensitivity. Anal. Biochem. 117: 307–310.

33. Murray, N. E., W. J. Brammer, and K. Murray. 1977. Lamboid phages that simplify the recovery of in vitro recombinants. Mol. Gen. Genet. 150: 53–58.

34. Platt, T. 1986. Transcription termination and the regulation of gene expression. Annu. Rev. Biochem. 55: 339–372.

35. Pozzi, G., M. R. Oggioni, and A. Tomasz. 1989. DNA probe for identification of *Streptococcus pneumoniae*. J. Clin. Microbiol. 27: 370–372.

36. Saiki, R. K., D. H. Gelfand, S. Stoffel, S. J. Scharf, R. Higuchi, G. T. Horn, D. B. Mullis, and H. A. Ehrlich. 1988. Primer-directed enzymatic amplification of DNA with thermostable DNA polymerase. Science 239: 487–491.

37. Sanger, F., S. Nicklen, and A. R. Coulson. 1977. DNA sequencing with chain-terminating inhibitors. Proc. Natl. Acad. Sci. USA. 74: 5463–5467.

38. Schneewind, O., K. F. Jones, and V. A. Fischetti. 1990. Sequence and structural characteristics of the trypsin-resistant T6 surface protein of group A Streptococci. J. Bacteriol. 172: 3310–3317.

39. Signas, C., G. Raucci, K. Jonsson, P-.E. Lindgren, G. M. Anantharamaiah, M. Hook, and M. Lindberg. 1989. Nucleotide sequence of the gene for a fibronectine-binding protein from *Staphylococcus aureus*: Use of this peptide sequence in the synthesis of biologically active peptides. Proc. Natl. Acad. Sci. 16: 699–703.

40. Tinoco, Jr. I., P. N. Borer, B. Dengler, M. D. Devine, O. C. Uhlenbeck, D. M. Crothers, and J. Gralla. 1973. Improved estimation of secondary structure in ribonucleic acids. Nature 246: 40–41.

41. Uhlen, M., B. Guss, B. Nilsson, S. Gatenbeck, L. Philipson and M. Lindberg. 1984. Complete sequence of the Staphylococcal gene encoding protein A. J. Biol. Chem.259: 1695–1702.

42. Valli, V. E. O. 1985. The Hematopoietic System-Spleen and Hemolymph Nodes, p. 194–200. In: K. V. F. Jubb, P. C. Kennedy and N. Palmer, Pathology of Domestic Animals. Volume 3. 3rd ed. Academic Press, Inc. Orlando Fla.

43. Vecht, U., J. P. Arends, E. J. van der Molen, and L. A. M. G. van Leengoed. 1989. Differences in virulence between two strains of *Streptococcus suis* type 2 after experimentally induced infection of newborn germ-free pigs. Am. J. Vet. Res., 50: 1037–1043.

44. Vecht, U., L. A. M. G. van Leengoed, and E. R. M. Verheyen. 1985. *Streptococcus suis* infections in pigs in The Netherlands (part one). Vet. Quart. 7: 315–321.

45. Von Heijne, G. 1986. A new method for predicting signal sequence cleavage sites. Nucleic Acids Res. 14: 4683–4690.

46. Vos, P., G. Simons, R. J. Siezen, and W. M. de Vos. 1989. Primary structure and organization of the gene for a procaryotic cell envelope-located serine proteinase. J. Biol. Chem. 264: 13579–13585.

47. Vossen, J. M. B. M. van der, J. Kok, and G. Venema. 1985. Construction of cloning, promoter-screening, and terminator-screening shuttle vectors for *Bacillus subtilis* and *Lactococcus lactis* subsp. lactis. Appl. Environ. Microbiol. 50: 540–542.

48. Williams, A. E. and W. F. Blakemore. 1990. Pathogenesis of Meningitis Caused by Streptococcus suis type 2. J. Infect. Dis. 162: 474–481.

49. Wilson, B. and Nakane, P. K., 1978. Recent developments in the periodate method of conjugating horse-radish peroxidase (HRPO) to antibodies. In: W. Knapp, K. Holubar, and G. Wicks (Editors), Immunofluorescence and related staining techniques. Biomedical Press, Elsevier, Amsterdam, pp 215–224.

50. Windsor, R. S. 1977. Meningitis in pigs caused by *Streptococcus suis* type 2. Vet. Rec. 101: 378–379.

51. Zijderveld, F. G. van, Westenbrink, F., Anakotta, J., Brouwers, R. A. M. and van Zijderveld, A. M., 1989. Characterization of the F41 Fimbrial Antigen of Enterotoxigenic *Escherichia coli* by Using Monoclonal Antibodies. Inf. and Imm. 57: 1192–1199.

We claim:

1. A DNA sequence comprising at least 15 contiguous nucleotides of
   (a) the nucleotide sequence set forth as SEQ ID NO: 1, 2 or 3; or
   (b) a nucleotide sequence encoding the polypeptide set forth as SEQ ID NO: 1, 2 or 3.

2. A DNA sequence according to claim 1 which sequence contains at least 15 contiguous nucleotides selected from nucleotides 2890–3306 of SEQ ID No 2.

3. A DNA sequence according to claim 1 containing at least 15 contiguous nucleotides selected from nucleotides 1100–1934 of SEQ ID No 3.

4. An expression sequence, comprising a DNA sequence according to claim 1 operatively linked to a regulating sequence for expression of the polypeptide encoded by said DNA sequence.

5. A polynucleotide probe for the diagnosis of an infection by *streptococcus suis*, comprising a sequence according to claim 1.

6. A method for detecting an infection by a pathogenic strain of *Streptococcus suis*, comprising isolating DNA from a biological sample and contacting it with at least one probe according to claim 5, whereby the presence of the pathogenic strain of *Streptococcus suis* is detected.

7. A diagnostic kit for the detection of an infection by a pathogenic strain of *Streptococcus suis*, wherein the kit contains at least one probe according to claim 5.

8. A plasmid or a viral vector comprising an expression sequence according to claim 4.

9. A bacterium transformed with the plasmid or viral vector of claim 8.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4376 base pairs
( B ) TYPE: Nucleic acid with corresponding amino acids
( C ) STRANDEDNESS: single stranded
( D ) TOPOLOGY: linear ( i i ) MOLECULE TYPE: genomic DNA ( v i ) ORIGINAL SOURCE:
  ( A ) ORGANISM: *Streptococcus suis* type II (pathogenic)

( i x ) FEATURE:
  ( D ) OTHER INFORMATION: Extracellular protein factor (EF) gene ( i x ) FEATURE:
  ( A ) NAME/KEY: promoter -35 region
  ( B ) LOCATION: bp 66 to 71

( i x ) FEATURE:
  ( A ) NAME/KEY: promoter -10 region
  ( B ) LOCATION: bp 89 to 94

( i x ) FEATURE:
  ( A ) NAME/KEY: promoter -35 region
  ( B ) LOCATION: bp 153 to 158

( i x ) FEATURE:
  ( A ) NAME/KEY: promoter -10 region
  ( B ) LOCATION: bp 176 to 181

( i x ) FEATURE:
  ( A ) NAME/KEY: ribosome binding site
  ( B ) LOCATION: bp 350 to 356

( i x ) FEATURE:
  ( A ) NAME/KEY: signal peptide
  ( B ) LOCATION: bp 361 to 498

( i x ) FEATURE:
  ( A ) NAME/KEY: mature peptide
  ( B ) LOCATION: bp 499 to 2890

( i x ) FEATURE:
  ( A ) NAME/KEY: dyad symmetry regions
  ( B ) LOCATION: from bp 4186 to 4198 and from bp 4203 to 4215

( i x ) FEATURE:
  ( A ) NAME/KEY: dyad symmetry regions
  ( B ) LOCATION: from bp 4243 to 4257 and from bp 4263 to 4276

( x i ) SEQUENCE DESCRIPTION: SEQ ID NO:1:

```
TTGAACAACT TAAAACTAGT TAGTTTTGTT TAAAATGTAA TTGAATTGTC TTTTTAAGTA      60

GGCTGTTTAC ACGATATTTG TCTTCCTTTA TATAAATATG ATAGATTTTC AGTAAATTTT     120

TCAAAAAAAC CTCAAAAATA ACAGATTTTT TCTTGTATCT TGAGGCATA AGGAGTATAA      180

TGGTGACGGT ATTCAAGTAG AAATTTTATA TACTCTTGAT GAAAACATTC TGTCTACTTT     240

AAAATAAATA ATCTACTGGG TATCCTTCTG CTAAGTTTTT AAAGCAGGAG GTGTGTTTTT     300

GTACATGGTG TTACAGGAAC CAGAAATGAT CGATTCGCCA GTAAAATATA GGAGGATATC     360
```

| ATG | TCT | TAT | AAA | GAT | ATG | TTC | AGA | AAA | GAA | CAA | CGT | TTT | TCT | TTT | CGT | 408 |
| Met | Ser | Tyr | Lys | Asp | Met | Phe | Arg | Lys | Glu | Gln | Arg | Phe | Ser | Phe | Arg | |
| -45 | | | | | -40 | | | | | | -35 | | | | | |

| AAA | TTT | AGC | TTT | GGT | CTA | GCT | TCG | GCA | GTC | ATT | GCA | AAC | GTT | ATT | TTG | 456 |
| Lys | Phe | Ser | Phe | Gly | Leu | Ala | Ser | Ala | Val | Ile | Ala | Asn | Val | Ile | Leu | |
| -30 | | | | -25 | | | | | -20 | | | | | | -15 | |

| GGA | GGA | GCA | ATC | GCA | AAC | AGC | CCT | GTT | GTT | CAT | GCT | AAC | ACA | GTG | ACA | 504 |
| Gly | Gly | Ala | Ile | Ala | Asn | Ser | Pro | Val | Val | His | Ala | Asn | Thr | Val | Thr | |
| | | | | -10 | | | | | -5 | | | | | | 1 | |

| GAA | GCA | GAG | ACA | GCT | GTA | GCA | CCA | GCT | AAC | CAA | GAC | CTT | GGA | AAT | GAG | 552 |
| Glu | Ala | Glu | Thr | Ala | Val | Ala | Pro | Ala | Asn | Gln | Asp | Leu | Gly | Asn | Glu | |
| | | 5 | | | | | 10 | | | | | 15 | | | | |

| ACT | AAA | ACG | GAA | GAA | GAA | CCC | AAG | GAA | CCA | ATC | GAA | GCA | GTT | CGC | ACG | 600 |
| Thr | Lys | Thr | Glu | Glu | Glu | Pro | Lys | Glu | Pro | Ile | Glu | Ala | Val | Arg | Thr | |
| | 20 | | | | | 25 | | | | | 30 | | | | | |

| GAC | ATG | GAA | AAC | CGT | GCA | GCT | GAA | ATC | TTG | CCG | GAG | GCG | CTG | AAT | GCT | 648 |

| | | | | | | | | | | | | | | | |
|---|---|---|---|---|---|---|---|---|---|---|---|---|---|---|---|
| Asp | Met | Glu | Asn | Arg | Ala | Ala | Glu | Ile | Leu | Pro | Glu | Ala | Leu | Asn | Ala |
| 35 | | | | 40 | | | | | 45 | | | | | 50 | |

```
AGT GTA ACA AAC CAA GCA CCA GTT ATT CCG ACT ATT GGA GAT CTT CCT        696
Ser Val Thr Asn Gln Ala Pro Val Ile Pro Thr Ile Gly Asp Leu Pro
             55                      60                      65

AAA GAT GCG AGT GGT CAG AAT GTT CAT GGT AAG GCA ACG GAT AAT AAG        744
Lys Asp Ala Ser Gly Gln Asn Val His Gly Lys Ala Thr Asp Asn Lys
                 70                  75                  80

ATT TAT CGT GTT GTA TAC GTT TTT GGT AAT GTA GCA GGG ACT ACG GAG        792
Ile Tyr Arg Val Val Tyr Val Phe Gly Asn Val Ala Gly Thr Thr Glu
             85                  90                  95

ACA GAA GAT GGT AAA CAA AAT GTT GCT CCA ACA TTT AAC AGA AAT GAT        840
Thr Glu Asp Gly Lys Gln Asn Val Ala Pro Thr Phe Asn Arg Asn Asp
         100                 105                 110

GCA ACT AAA ACT TTT CCA ATC ACA GAT CCA GAT AGC GAC ATT CAA ACT        888
Ala Thr Lys Thr Phe Pro Ile Thr Asp Pro Asp Ser Asp Ile Gln Thr
115                 120                 125                 130

ATT TCA TAC GAA GTT CCA GCT GAT ATT GCA AGC TAT ACC TTG GAT GAT        936
Ile Ser Tyr Glu Val Pro Ala Asp Ile Ala Ser Tyr Thr Leu Asp Asp
                 135                 140                 145

CCA AAC TCA ATT GTT ACT AAT GGC ACC TCA CCT GGT CCA GTA TCT TAC        984
Pro Asn Ser Ile Val Thr Asn Gly Thr Ser Pro Gly Pro Val Ser Tyr
             150                 155                 160

TTA GAT GGT CCA AAT GGG TCA GCC ACT CTC ACA CAA GAT GGT TAT CTA       1032
Leu Asp Gly Pro Asn Gly Ser Ala Thr Leu Thr Gln Asp Gly Tyr Leu
             165                 170                 175

ACA GGA AGT TTC CCT TGG GGA GCA GGA GAC CTA GCT GGT CGT CGG ATT       1080
Thr Gly Ser Phe Pro Trp Gly Ala Gly Asp Leu Ala Gly Arg Arg Ile
         180                 185                 190

AAA GTG ACG GAT GCC ACT GGT AAT ACT ACT AAG AGT AAT CCG TTC TAT       1128
Lys Val Thr Asp Ala Thr Gly Asn Thr Thr Lys Ser Asn Pro Phe Tyr
195                 200                 205                 210

ATG GTT GCA TAT ACA GTC AAG CCA GTA GAT GAT AAA CCT CTA GCA GTA       1176
Met Val Ala Tyr Thr Val Lys Pro Val Asp Asp Lys Pro Leu Ala Val
                 215                 220                 225

TCA AAC TCT TCT GAG CTG ACG GAA CAG GCT ATT TTT GAT AAG TTG GTT       1224
Ser Asn Ser Ser Glu Leu Thr Glu Gln Ala Ile Phe Asp Lys Leu Val
             230                 235                 240

GTC GAT AAG TCT GCT AAA ACA ACT TCA AAT AGC GCT CTT GTA ATT GAT       1272
Val Asp Lys Ser Ala Lys Thr Thr Ser Asn Ser Ala Leu Val Ile Asp
             245                 250                 255

TCT AGC AAC TAC AAA CAT TCA ATT GCA GGT TAT CGT ACC GTA AAT TCT       1320
Ser Ser Asn Tyr Lys His Ser Ile Ala Gly Tyr Arg Thr Val Asn Ser
260                 265                 270

GAT GGC ACA AAA ACA GAA ACA GTA GAG GAA ACA AAT CTA TCT GAT TTC       1368
Asp Gly Thr Lys Thr Glu Thr Val Glu Glu Thr Asn Leu Ser Asp Phe
275                 280                 285                 290

CCA ACT GAA GGT AAA TAC GAA GTT CGA GTA AAA ACA ACC AAT GTT TAC       1416
Pro Thr Glu Gly Lys Tyr Glu Val Arg Val Lys Thr Thr Asn Val Tyr
                 295                 300                 305

GGT CAA ACT ATC TAC AAC TGG ATT CCT GTA AAT GCC TAT AAG TTG GAC       1464
Gly Gln Thr Ile Tyr Asn Trp Ile Pro Val Asn Ala Tyr Lys Leu Asp
             310                 315                 320

ACA GCG AAG GAT GCT GAA ATT CGG AAG TAT ACA GAC AAC CAA GCC CCA       1512
Thr Ala Lys Asp Ala Glu Ile Arg Lys Tyr Thr Asp Asn Gln Ala Pro
         325                 330                 335

ATT CAT GCT ATA ATG CAA ATT GGT CAA GCT GGA GAA AAG GCA GCA GTT       1560
Ile His Ala Ile Met Gln Ile Gly Gln Ala Gly Glu Lys Ala Ala Val
340                 345                 350

ATA TTG AAG GAT ATT CCA TCC GAT TTC AGT ATT GAA AAC TTC AAT TTG       1608
```

|     |     |     |     |     |     |     |     |     |     |     |     |     |     |     |     |
| --- | --- | --- | --- | --- | --- | --- | --- | --- | --- | --- | --- | --- | --- | --- | --- |
| Ile | Leu | Lys | Asp | Ile | Pro | Ser | Asp | Phe | Ser | Ile | Glu | Asn | Phe | Asn | Leu |
| 355 |     |     |     | 360 |     |     |     |     | 365 |     |     |     |     |     | 370 |

| AAA | GAT | GGT | GTA | GCA | GAT | GAG | CTT | GCT | AAA | CGT | AAC | TTG | GAA | TTT | GTA | 1656 |
|---|---|---|---|---|---|---|---|---|---|---|---|---|---|---|---|---|
| Lys | Asp | Gly | Val | Ala | Asp | Glu | Leu | Ala | Lys | Arg | Asn | Leu | Glu | Phe | Val | |
|  |  |  |  | 375 |  |  |  |  | 380 |  |  |  |  | 385 |  |  |
| AGA | AAT | GAT | GCA | GTG | GCG | ACA | ACT | GAT | ACT | GAT | GGA | GAT | GGC | GCC | AAA | 1704 |
| Arg | Asn | Asp | Ala | Val | Ala | Thr | Thr | Asp | Thr | Asp | Gly | Asp | Gly | Ala | Lys | |
|  |  | 390 |  |  |  |  | 395 |  |  |  |  | 400 |  |  |  |  |
| GAA | GGA | ATT | GTT | GGA | TAT | ATT | CAA | CCA | AAA | ACT | GGC | GGT | GCA | AAC | AGT | 1752 |
| Glu | Gly | Ile | Val | Gly | Tyr | Ile | Gln | Pro | Lys | Thr | Gly | Gly | Ala | Asn | Ser | |
|  |  | 405 |  |  |  |  | 410 |  |  |  |  | 415 |  |  |  |  |
| GGG | GTA | GCC | ACT | TAT | ACA | GGA | TCA | AAT | AAT | CTT | ACT | TAT | GGC | TTC | ACT | 1800 |
| Gly | Val | Ala | Thr | Tyr | Thr | Gly | Ser | Asn | Asn | Leu | Thr | Tyr | Gly | Phe | Thr | |
|  | 420 |  |  |  |  | 425 |  |  |  |  | 430 |  |  |  |  |  |
| TAC | AAA | GCT | GTT | GAG | ACA | AAA | GAT | AAG | GCG | AAT | GCC | ACA | GAG | GCT | AAA | 1848 |
| Tyr | Lys | Ala | Val | Glu | Thr | Lys | Asp | Lys | Ala | Asn | Ala | Thr | Glu | Ala | Lys | |
| 435 |  |  |  |  | 440 |  |  |  |  | 445 |  |  |  |  | 450 |  |
| ACT | CTC | GAA | TTA | GAT | TAC | ACC | ATC | TTA | TTC | ATA | GAT | ACT | AAA | GCA | CCA | 1896 |
| Thr | Leu | Glu | Leu | Asp | Tyr | Thr | Ile | Leu | Phe | Ile | Asp | Thr | Lys | Ala | Pro | |
|  |  |  |  | 455 |  |  |  |  | 460 |  |  |  |  | 465 |  |  |
| GTC | ATG | ACA | CCT | AAA | TCA | GAG | TAC | ATC | CGT | TTT | GTT | GGT | GAA | GAG | TAT | 1944 |
| Val | Met | Thr | Pro | Lys | Ser | Glu | Tyr | Ile | Arg | Phe | Val | Gly | Glu | Glu | Tyr | |
|  |  |  | 470 |  |  |  |  | 475 |  |  |  |  | 480 |  |  |  |
| ACG | GTT | AGC | GTC | CCA | GGT | ACG | GAT | AAC | GCC | TTC | CTT | AAT | ACC | GGC | AAA | 1992 |
| Thr | Val | Ser | Val | Pro | Gly | Thr | Asp | Asn | Ala | Phe | Leu | Asn | Thr | Gly | Lys | |
|  |  | 485 |  |  |  |  | 490 |  |  |  |  | 495 |  |  |  |  |
| CTA | AAT | GGA | ACT | CTC | TCA | ATT | TTG | AAA | GAT | GGA | GAG | TCA | GGT | TCT | CTT | 2040 |
| Leu | Asn | Gly | Thr | Leu | Ser | Ile | Leu | Lys | Asp | Gly | Glu | Ser | Gly | Ser | Leu | |
|  | 500 |  |  |  |  | 505 |  |  |  |  | 510 |  |  |  |  |  |
| GTA | TCA | TCA | GAC | TTA | GGT | ACA | AAC | ACT | AAG | ATT | ACT | TCA | GAA | CTG | GAT | 2088 |
| Val | Ser | Ser | Asp | Leu | Gly | Thr | Asn | Thr | Lys | Ile | Thr | Ser | Glu | Leu | Asp | |
| 515 |  |  |  |  | 520 |  |  |  |  | 525 |  |  |  |  | 530 |  |
| CCT | ACG | GGA | GCA | ACT | GCA | AAC | CAA | GGA | GAT | GAC | GGT | CAA | TCT | TCA | ACT | 2136 |
| Pro | Thr | Gly | Ala | Thr | Ala | Asn | Gln | Gly | Asp | Asp | Gly | Gln | Ser | Ser | Thr | |
|  |  |  |  | 535 |  |  |  |  | 540 |  |  |  |  | 545 |  |  |
| AAG | TTT | AAC | GTT | AAG | ATT | ACA | GGT | ACC | GGA | CCT | GCT | ACA | GAA | GGT | ACC | 2184 |
| Lys | Phe | Asn | Val | Lys | Ile | Thr | Gly | Thr | Gly | Pro | Ala | Thr | Glu | Gly | Thr | |
|  |  |  | 550 |  |  |  |  | 555 |  |  |  |  | 560 |  |  |  |
| GGC | ACT | TAT | AAG | CTT | CGT | GTT | GGA | GAA | GAT | AAC | TAT | CCT | TTT | GGT | CCA | 2232 |
| Gly | Thr | Tyr | Lys | Leu | Arg | Val | Gly | Glu | Asp | Asn | Tyr | Pro | Phe | Gly | Pro | |
|  |  | 565 |  |  |  |  | 570 |  |  |  |  | 575 |  |  |  |  |
| GAG | GGG | AAA | CTT | GTT | GAT | GGA | AAT | AAA | CCA | GAA | AAT | GTA | GGT | TTG | ACA | 2280 |
| Glu | Gly | Lys | Leu | Val | Asp | Gly | Asn | Lys | Pro | Glu | Asn | Val | Gly | Leu | Thr | |
|  | 580 |  |  |  |  | 585 |  |  |  |  | 590 |  |  |  |  |  |
| TCT | GTA | AAA | GTT | ACC | TTC | GTA | AAA | CAT | GCT | ACG | GTG | TCA | ACA | CCA | GTT | 2328 |
| Ser | Val | Lys | Val | Thr | Phe | Val | Lys | His | Ala | Thr | Val | Ser | Thr | Pro | Val | |
| 595 |  |  |  |  | 600 |  |  |  |  | 605 |  |  |  |  | 610 |  |
| TCT | GTT | GAA | AAT | CCA | GCT | AAC | TTA | ACG | CCA | GAA | GAA | AAA | GCC | GCA | GTT | 2376 |
| Ser | Val | Glu | Asn | Pro | Ala | Asn | Leu | Thr | Pro | Glu | Glu | Lys | Ala | Ala | Val | |
|  |  |  |  | 615 |  |  |  |  | 620 |  |  |  |  | 625 |  |  |
| ATT | GCT | CAA | ATC | AAG | AAA | GAC | AAC | GCA | GAC | AAC | GAA | AGA | TTG | AAG | GGC | 2424 |
| Ile | Ala | Gln | Ile | Lys | Lys | Asp | Asn | Ala | Asp | Asn | Glu | Arg | Leu | Lys | Gly | |
|  |  |  | 630 |  |  |  |  | 635 |  |  |  |  | 640 |  |  |  |
| TTG | CCA | GAT | TCA | GCA | TTT | ACA | GTT | AAC | TCA | GAT | GGT | ACT | GTG | TCA | GTT | 2472 |
| Leu | Pro | Asp | Ser | Ala | Phe | Thr | Val | Asn | Ser | Asp | Gly | Thr | Val | Ser | Val | |
|  |  | 645 |  |  |  |  | 650 |  |  |  |  | 655 |  |  |  |  |
| GAC | TAC | AGT | GCC | GGT | GGT | GTC | AAT | GTT | GAT | GGT | GCG | ACA | GAC | ATT | ATT | 2520 |
| Asp | Tyr | Ser | Ala | Gly | Gly | Val | Asn | Val | Asp | Gly | Ala | Thr | Asp | Ile | Ile | |
|  | 660 |  |  |  |  | 665 |  |  |  |  | 670 |  |  |  |  |  |
| AAG | AAT | GCT | ACC | ACA | AAC | TTG | GCA | GAT | ACA | CGG | AAT | GAA | GCA | AAA | GCA | 2568 |

| | | | | | | | | | | | | | | | |
|---|---|---|---|---|---|---|---|---|---|---|---|---|---|---|---|
| Lys | Asn | Ala | Thr | Thr | Asn | Leu | Ala | Asp | Thr | Arg | Asn | Glu | Ala | Lys | Ala |
| 675 | | | | | 680 | | | | 685 | | | | | | 690 |

| | | | | | | | | | | | | | | | | |
|---|---|---|---|---|---|---|---|---|---|---|---|---|---|---|---|---|
| GAA | ATC | GAC | ACA | AAA | TTA | GCT | GAA | CAT | AAA | AAA | GCT | ATC | GAA | GCA | AAA | 2616 |
| Glu | Ile | Asp | Thr | Lys | Leu | Ala | Glu | His | Lys | Lys | Ala | Ile | Glu | Ala | Lys | |
| | | | | 695 | | | | 700 | | | | | 705 | | | |
| CGG | GAT | GAA | GCG | TTT | TCT | AAA | ATT | GAT | GAT | GAC | ATT | TCC | TTG | AGA | GCA | 2664 |
| Arg | Asp | Glu | Ala | Phe | Ser | Lys | Ile | Asp | Asp | Asp | Ile | Ser | Leu | Arg | Ala | |
| | | | 710 | | | | 715 | | | | | 720 | | | | |
| GAA | CAG | AGA | CAG | GCT | GCT | AAG | GAT | GCC | GTT | GCT | GCA | GCT | GCT | GGG | GAT | 2712 |
| Glu | Gln | Arg | Gln | Ala | Ala | Lys | Asp | Ala | Val | Ala | Ala | Ala | Ala | Gly | Asp | |
| | | 725 | | | | 730 | | | | | 735 | | | | | |
| GCT | TTG | AAA | GAA | TTA | GAC | AAC | AAG | GCG | ACA | GAA | GCA | AAA | GAA | AAA | ATT | 2760 |
| Ala | Leu | Lys | Glu | Leu | Asp | Asn | Lys | Ala | Thr | Glu | Ala | Lys | Glu | Lys | Ile | |
| | | 740 | | | | 745 | | | | | 750 | | | | | |
| GAT | AAA | GCT | ACG | ACG | GCC | TCA | GAA | ATC | AAT | GAT | GCT | AAG | ACT | AAT | GGT | 2808 |
| Asp | Lys | Ala | Thr | Thr | Ala | Ser | Glu | Ile | Asn | Asp | Ala | Lys | Thr | Asn | Gly | |
| 755 | | | | 760 | | | | | 765 | | | | | | 770 | |
| GAG | ATT | AAT | CTG | GAC | AGT | GCA | GAA | GCA | GTA | GGC | GAA | AAA | GCT | ATT | AAC | 2856 |
| Glu | Ile | Asn | Leu | Asp | Ser | Ala | Glu | Ala | Val | Gly | Glu | Lys | Ala | Ile | Asn | |
| | | | | 775 | | | | 780 | | | | | | 785 | | |
| CAG | TCG | AAG | CGC | AAT | CGG | CAG | AGG | ACA | AAG | GCG | TAG | GT | TCA | ATC | GCC | 2903 |
| Gln | Ser | Lys | Arg | Asn | Arg | Gln | Arg | Thr | Lys | Ala | | | | | | |
| | | | 790 | | | | | 795 | | | | | | | | |
| CAA | GAT | GTT | CTT | GAC | GCA | GCG | AAA | CAA | GAT | GCT | AAG | AAT | AAG | ATT | GCT | 2951 |
| Gln | Asp | Val | Leu | Asp | Ala | Ala | Lys | Gln | Asp | Ala | Lys | Asn | Lys | Ile | Ala | |
| | | 800 | | | | | 805 | | | | | 810 | | | | |
| AAA | GAA | TCC | GAC | GCT | GCT | AAG | TCA | GCC | ATT | GAC | GCG | AAT | CCA | AAC | TTG | 2999 |
| Lys | Glu | Ser | Asp | Ala | Ala | Lys | Ser | Ala | Ile | Asp | Ala | Asn | Pro | Asn | Leu | |
| | 815 | | | | | 820 | | | | | 825 | | | | | |
| ACA | GAT | GCA | GAG | AAG | GAA | TCA | GCT | AAG | AAA | GCG | GTA | GAT | GCA | GAT | GCT | 3047 |
| Thr | Asp | Ala | Glu | Lys | Glu | Ser | Ala | Lys | Lys | Ala | Val | Asp | Ala | Asp | Ala | |
| 830 | | | | | 835 | | | | | 840 | | | | | 845 | |
| AAA | GCT | GCG | ACA | GAT | GCA | ATT | GAT | GCT | TCA | ACA | AGT | CCA | GTC | GAA | GCG | 3095 |
| Lys | Ala | Ala | Thr | Asp | Ala | Ile | Asp | Ala | Ser | Thr | Ser | Pro | Val | Glu | Ala | |
| | | | | 850 | | | | | 855 | | | | | 860 | | |
| CAA | TCG | GCA | GAG | GAC | AAA | GGC | GTA | GGC | GCC | ATC | GCC | AAA | GAC | ATT | CTT | 3143 |
| Gln | Ser | Ala | Glu | Asp | Lys | Gly | Val | Gly | Ala | Ile | Ala | Lys | Asp | Ile | Leu | |
| | | | | 865 | | | | | 870 | | | | 875 | | | |
| GAT | GCC | GCG | AAA | CAA | GAT | GCT | AAG | AAC | AAG | ATT | GCT | AAA | GAG | GCA | GAA | 3191 |
| Asp | Ala | Ala | Lys | Gln | Asp | Ala | Lys | Asn | Lys | Ile | Ala | Lys | Glu | Ala | Glu | |
| | | 880 | | | | | 885 | | | | | 890 | | | | |
| TCC | GCT | AAG | TCA | GTC | ATT | GAC | TCC | AAT | CCG | AAC | TTG | ACA | GAT | GCA | GCT | 3239 |
| Ser | Ala | Lys | Ser | Val | Ile | Asp | Ser | Asn | Pro | Asn | Leu | Thr | Asp | Ala | Ala | |
| | 895 | | | | | 900 | | | | | 905 | | | | | |
| AAG | GAA | GCG | GCT | AAA | TCT | GAA | ATT | GAT | AAA | GCT | GTT | GAG | GAA | GCG | ATT | 3287 |
| Lys | Glu | Ala | Ala | Lys | Ser | Glu | Ile | Asp | Lys | Ala | Val | Glu | Glu | Ala | Ile | |
| 910 | | | | | 915 | | | | | 920 | | | | | 925 | |
| GTT | TTA | ATC | AAT | GGT | GTT | AGA | ACT | TAT | CAA | GAG | TTG | GAA | AAA | ATC | AAA | 3335 |
| Val | Leu | Ile | Asn | Gly | Val | Arg | Thr | Tyr | Gln | Glu | Leu | Glu | Lys | Ile | Lys | |
| | | | | 930 | | | | | 935 | | | | | 940 | | |
| CTT | CCA | ATG | GCA | GCT | CTA | ATT | AAA | CCA | GCT | GCG | AAA | GTA | ACA | CCA | GTG | 3383 |
| Leu | Pro | Met | Ala | Ala | Leu | Ile | Lys | Pro | Ala | Ala | Lys | Val | Thr | Pro | Val | |
| | | | 945 | | | | | 950 | | | | | 955 | | | |
| GTT | GAT | CCA | AAT | AAC | TTG | ACT | GAA | AAA | GAA | ATT | GCT | CGT | ATC | AAG | GCA | 3431 |
| Val | Asp | Pro | Asn | Asn | Leu | Thr | Glu | Lys | Glu | Ile | Ala | Arg | Ile | Lys | Ala | |
| | | 960 | | | | 965 | | | | | 970 | | | | | |
| TTC | CTT | AAA | GAG | AAC | AAT | AAC | CTC | CCA | TAA | GGA | ACA | GAG | ATT | AAT | GTT | 3479 |
| Phe | Leu | Lys | Glu | Asn | Asn | Asn | Leu | Pro | | Gly | Thr | Glu | Ile | Asn | Val | |
| 975 | | | | | 980 | | | | | | | 985 | | | | |
| TCT | AAA | GAT | GCT | TCA | GTG | ACA | ATT | AAA | TAT | CCA | GAT | GGA | ACT | ATT | GAT | 3527 |

| | | | | | | | | | | | | | | | | |
|---|---|---|---|---|---|---|---|---|---|---|---|---|---|---|---|---|
| Ser | Lys | Asp | Ala | Ser | Val | Thr | Ile | Lys | Tyr | Pro | Asp | Gly | Thr | Ile | Asp | |
| | 990 | | | | 995 | | | | | 1000 | | | | | | |
| TTG | CTA | TCA | CCA | GTA | GAA | GTT | GTG | AAG | CAG | GCA | GAT | AAA | ACT | GCT | CCT | 3575 |
| Leu | Leu | Ser | Pro | Val | Glu | Val | Val | Lys | Gln | Ala | Asp | Lys | Thr | Ala | Pro | |
| 1005 | | | | 1010 | | | | | 1015 | | | | | 1020 | | |
| ACG | GTC | GCA | AAT | GAT | GGC | AAA | GGT | AAT | ATT | GTG | ATT | GTA | CCG | TCT | GAA | 3623 |
| Thr | Val | Ala | Asn | Asp | Gly | Lys | Gly | Asn | Ile | Val | Ile | Val | Pro | Ser | Glu | |
| | | | | 1025 | | | | | 1030 | | | | | 1035 | | |
| AAA | GCT | GTT | GAG | CTT | GTT | GTT | TCA | TAC | GTA | GAT | AAC | AAT | GGT | AAG | TCG | 3671 |
| Lys | Ala | Val | Glu | Leu | Val | Val | Ser | Tyr | Val | Asp | Asn | Asn | Gly | Lys | Ser | |
| | | | 1040 | | | | | 1045 | | | | | 1050 | | | |
| CAA | ACT | GTA | GTT | GTT | ACG | AAA | GGT | ACG | GAT | GGT | TTA | TGG | ACA | GCA | AGT | 3719 |
| Gln | Thr | Val | Val | Val | Thr | Lys | Gly | Thr | Asp | Gly | Leu | Trp | Thr | Ala | Ser | |
| | | 1055 | | | | | 1060 | | | | | 1065 | | | | |
| AAT | ACA | GTG | GTG | ATT | GTG | GAC | CCT | GTG | ACT | GGG | CAA | GTA | ATC | GTT | CCA | 3767 |
| Asn | Thr | Val | Val | Ile | Val | Asp | Pro | Val | Thr | Gly | Gln | Val | Ile | Val | Pro | |
| | 1070 | | | | | 1075 | | | | | 1080 | | | | | |
| GGT | TCT | GTT | ATT | AAG | CCA | GGT | ACA | GTT | GTT | ACA | GCA | TAC | TCT | AAA | GAC | 3815 |
| Gly | Ser | Val | Ile | Lys | Pro | Gly | Thr | Val | Val | Thr | Ala | Tyr | Ser | Lys | Asp | |
| 1085 | | | | | 1090 | | | | | 1095 | | | | | 1100 | |
| GAG | GTT | GGA | AAT | AGT | TCT | GAT | TCA | GCA | GAA | GCT | GAA | GTT | GTA | GCA | GTA | 3863 |
| Glu | Val | Gly | Asn | Ser | Ser | Asp | Ser | Ala | Glu | Ala | Glu | Val | Val | Ala | Val | |
| | | | | 1105 | | | | | 1110 | | | | | 1115 | | |
| GAC | GAA | AAT | AAT | TCT | GCA | GCA | GGA | GTG | AAA | GTT | AAA | TCA | GTT | ACT | ACA | 3911 |
| Asp | Glu | Asn | Asn | Ser | Ala | Ala | Gly | Val | Lys | Val | Lys | Ser | Val | Thr | Thr | |
| | | | 1120 | | | | | 1125 | | | | | 1130 | | | |
| AAT | GCT | AAT | AAT | GTT | GAG | AAG | AAA | GCT | AAG | CAA | TTA | CCG | AAT | ACT | GGT | 3959 |
| Asn | Ala | Asn | Asn | Val | Glu | Lys | Lys | Ala | Lys | Gln | Leu | Pro | Asn | Thr | Gly | |
| | | 1135 | | | | | 1140 | | | | | 1145 | | | | |
| GAG | GAA | GCA | AAT | TCA | GCA | ACT | TCA | CTC | GGA | TTA | GTA | GCT | CTT | GGA | CTC | 4007 |
| Glu | Glu | Ala | Asn | Ser | Ala | Thr | Ser | Leu | Gly | Leu | Val | Ala | Leu | Gly | Leu | |
| | 1150 | | | | | 1155 | | | | | 1160 | | | | | |
| GGA | TTA | GCA | CTT | CTT | GCA | GCA | AAG | AGA | AGA | AGA | GAC | GAA | GAA | GCT | TAA | 4055 |
| Gly | Leu | Ala | Leu | Leu | Ala | Ala | Lys | Arg | Arg | Arg | Asp | Glu | Glu | Ala | | |
| 1165 | | | | | 1170 | | | | | 1175 | | | | | | |

| | | | | |
|---|---|---|---|---|
| GATAAGCTCT | TCCTCAGAAC | TCTTTTGGAA | GCCGCAATTT | TCCTAGAAGA | TAGTAGTATG | 4115 |
| ATACTCTTTC | ATAGCAAGGA | AATTCCCTCG | CTATGATTGG | TAGGTATCAG | TTATTATCTA | 4175 |
| TCGAACCCCC | AAAATCCAAA | GTCATTCGAC | TTTGGATTTT | TTGATACGA | CATGCTCGTC | 4235 |
| ATACCTAAAA | AACAGCCTTC | TCTTGCCGAG | AGGCTGTTTT | TCATGCTTTT | AATCTAAAAG | 4295 |
| TCTGCGGACG | TTTTTCAAT | AAAATCCAGT | AACCGATGCT | AACATAGGCA | ATCATAGCTA | 4355 |
| GGGAAACCAG | CAGGATATAG | G | | | | 4376 |

( 2 ) INFORMATION FOR SEQ ID NO:2:

( i ) SEQUENCE CHARACTERISTICS:
        ( A ) LENGTH: 6744 base pairs
        ( B ) TYPE: Nucleic acid with corresponding amino acids
        ( C ) STRANDEDNESS: single stranded
        ( D ) TOPOLOGY: linear ( i i ) MOLECULE TYPE: genomic DNA ( v i ) ORIGINAL SOURCE:
        ( A ) ORGANISM: *Streptococcus suis* type II (pathogenic)

( i x ) FEATURE:
        ( D ) OTHER INFORMATION: Extracellular factor related protein
            ( E F * ) gene ( i x ) FEATURE:
        ( A ) NAME/KEY: promoter -35 region
        ( B ) LOCATION: bp 66 to 71

( i x ) FEATURE:
    ( A ) NAME/KEY: promoter -10 region
    ( B ) LOCATION: bp 89 to 94

( i x ) FEATURE:
    ( A ) NAME/KEY: promoter -35 region
    ( B ) LOCATION: bp 153 to 158

( i x ) FEATURE:
    ( A ) NAME/KEY: promoter -10 region
    ( B ) LOCATION: bp 176 to 181

( i x ) FEATURE:
    ( A ) NAME/KEY: ribosome binding site
    ( B ) LOCATION: bp 350 to 356

( i x ) FEATURE:
    ( A ) NAME/KEY: signal peptide
    ( B ) LOCATION: bp 361 to 498

( i x ) FEATURE:
    ( A ) NAME/KEY: start of repetitive units R1-R11
    ( B ) LOCATION: bp 2869, 3097, 3292, 3520, 4087, 4381, 4609,
              4837, 5065, 5293, 5521:

( i x ) FEATURE:
    ( A ) NAME/KEY: start of repetitive Asn—Pro—Asn—Leu sequences
    ( B ) LOCATION: bp 2932, 3160, 3355, 3583, 4150, 4444, 4672,
              4900, 5128, 5356, 5584:

( i x ) FEATURE:
    ( A ) NAME/KEY: dyad symmetry regions
    ( B ) LOCATION: from bp 6554 to 6566 and from bp 6571 to 6583

( i x ) FEATURE:
    ( A ) NAME/KEY: dyad symmetry regions
    ( B ) LOCATION: from bp 6611 to 6625 and from bp 6631 to 6644

( x i ) SEQUENCE DESCRIPTION: SEQ ID NO:2:

```
TTGAACAACT  TAAAACTAGT  TAGTTTTGTT  TAAAATGTAA  TTGAATTGTC  TTTTTAAGTA        60

GGCTGTTTAC  ACGATATTTG  TCTTCCTTTA  TATAAATATG  ATAGATTTTC  AGTAAATTTT       120

TCAAAAAAAC  CTCAAAAATA  ACAGATTTTT  TCTTGTATCT  TTGAGGCATA  AGGAGTATAA       180

TGGTGACGGT  ATTCAAGTAG  AAATTTTATA  TACTCTTGAT  GAAAACATTC  TGTCTACTTT       240

AAAATAAATA  ATCTACTGGG  TATCCTTCTG  CTAAGTTTTT  AAAGCAGGAG  GTGTGTTTTT       300

GTACATGGTG  TTACAGGAAC  CAGAAATGAT  CGATTCGCCA  GTAAAATATA  GGAGGATATC       360
```

| | | | | | | | | | | | | | | | | |
|---|---|---|---|---|---|---|---|---|---|---|---|---|---|---|---|---|
| ATG | TCT | TAT | AAA | GAT | ATG | TTC | AGA | AAA | GAA | CAA | CGT | TTT | TCT | TTT | CGT | 408 |
| Met | Ser | Tyr | Lys | Asp | Met | Phe | Arg | Lys | Glu | Gln | Arg | Phe | Ser | Phe | Arg | |
| -45 | | | | | -40 | | | | | -35 | | | | | | |
| AAA | TTT | AGC | TTT | GGT | CTA | GCT | TCG | GCA | GTC | ATT | GCA | AAC | GTT | ATT | TTG | 456 |
| Lys | Phe | Ser | Phe | Gly | Leu | Ala | Ser | Ala | Val | Ile | Ala | Asn | Val | Ile | Leu | |
| -30 | | | | | -25 | | | | | -20 | | | | | -15 | |
| GGA | GGA | GCA | ATC | GCA | AAC | AGC | CCT | GTT | GTT | CAT | GCT | AAC | ACA | GTG | ACA | 504 |
| Gly | Gly | Ala | Ile | Ala | Asn | Ser | Pro | Val | Val | His | Ala | Asn | Thr | Val | Thr | |
| | | | | -10 | | | | | -5 | | | | | 1 | | |
| GAA | GCA | GAG | ACA | GCT | GTA | GCA | CCA | GCT | AAC | CAA | GAC | CTT | GGA | AAT | GAG | 552 |
| Glu | Ala | Glu | Thr | Ala | Val | Ala | Pro | Ala | Asn | Gln | Asp | Leu | Gly | Asn | Glu | |
| | | 5 | | | | | 10 | | | | | 15 | | | | |
| ACT | AAA | ACG | GAA | GAA | GAA | CCC | AAG | GAA | CCA | ATC | GAA | GCA | GTT | CGC | ACG | 600 |
| Thr | Lys | Thr | Glu | Glu | Glu | Pro | Lys | Glu | Pro | Ile | Glu | Ala | Val | Arg | Thr | |
| | | 20 | | | | | 25 | | | | | 30 | | | | |
| GAC | ATG | GAA | AAC | CGT | GCA | GCT | GAA | ATC | TTG | CCG | GAG | GCG | CTG | AAT | GCT | 648 |
| Asp | Met | Glu | Asn | Arg | Ala | Ala | Glu | Ile | Leu | Pro | Glu | Ala | Leu | Asn | Ala | |
| 35 | | | | | 40 | | | | | 45 | | | | | 50 | |
| AGT | GTA | ACA | AAC | CAA | GCA | CCA | GTT | ATT | CCG | ACT | ATT | GGA | GAT | CTT | CCT | 696 |
| Ser | Val | Thr | Asn | Gln | Ala | Pro | Val | Ile | Pro | Thr | Ile | Gly | Asp | Leu | Pro | |
| | | | | 55 | | | | | 60 | | | | | 65 | | |

-continued

| | | | | | | | | | | | | | | | | |
|---|---|---|---|---|---|---|---|---|---|---|---|---|---|---|---|---|
| AAA | GAT | GCG | AGT | GGT | CAG | AAT | GTT | CAT | GGT | AAG | GCA | ACG | GAT | AAT | AAG | 744 |
| Lys | Asp | Ala | Ser 70 | Gly | Gln | Asn | Val 75 | His | Gly | Lys | Ala | Thr | Asp 80 | Asn | Lys | |
| ATT | TAT | CGT | GTT | GTA | TAC | GTT | TTT | GGT | AAT | GTA | GCA | GGG | ACT | ACG | GAG | 792 |
| Ile | Tyr | Arg 85 | Val | Val | Tyr | Val | Phe 90 | Gly | Asn | Val | Ala | Gly 95 | Thr | Thr | Glu | |
| ACA | GAA | GAT | GGT | AAA | CAA | AAT | GTT | GCT | CCA | ACA | TTT | AAC | AGA | AAT | GAT | 840 |
| Thr | Glu 100 | Asp | Gly | Lys | Gln | Asn 105 | Val | Ala | Pro | Thr | Phe 110 | Asn | Arg | Asn | Asp | |
| GCA | ACT | AAA | ACT | TTT | CCA | ATC | ACA | GAT | CCA | GAT | AGC | GAC | ATT | CAA | ACT | 888 |
| Ala 115 | Thr | Lys | Thr | Phe | Pro 120 | Ile | Thr | Asp | Pro | Asp 125 | Ser | Asp | Ile | Gln | Thr 130 | |
| ATT | TCA | TAC | GAA | GTT | CCA | GCT | GAT | ATT | GCA | AGC | TAT | ACC | TTG | GAT | GAT | 936 |
| Ile | Ser | Tyr | Glu 135 | Val | Pro | Ala | Asp | Ile 140 | Ala | Ser | Tyr | Thr | Leu 145 | Asp | Asp | |
| CCA | AAC | TCA | ATT | GTT | ACT | AAT | GGC | ACC | TCA | CCT | GGT | CCA | GTA | TCT | TAC | 984 |
| Pro | Asn | Ser | Ile 150 | Val | Thr | Asn | Gly | Thr 155 | Ser | Pro | Gly | Pro | Val 160 | Ser | Tyr | |
| TTA | GAT | GGT | CCA | AAT | GGG | TCA | GCC | ACT | CTC | ACA | CAA | GAT | GGT | TAT | CTA | 1032 |
| Leu | Asp | Gly 165 | Pro | Asn | Gly | Ser | Ala 170 | Thr | Leu | Thr | Gln | Asp 175 | Gly | Tyr | Leu | |
| ACA | GGA | AGT | TTC | CCT | TGG | GGA | GCA | GGA | GAC | CTA | GCT | GGT | CGT | CGG | ATT | 1080 |
| Thr | Gly 180 | Ser | Phe | Pro | Trp | Gly 185 | Ala | Gly | Asp | Leu | Ala 190 | Gly | Arg | Arg | Ile | |
| AAA | GTG | ACG | GAT | GCC | ACT | GGT | AAT | ACT | ACT | AAG | AGT | AAT | CCG | TTC | TAT | 1128 |
| Lys 195 | Val | Thr | Asp | Ala | Thr 200 | Gly | Asn | Thr | Thr | Lys 205 | Ser | Asn | Pro | Phe | Tyr 210 | |
| ATG | GTT | GCA | TAT | ACA | GTC | AAG | CCA | GTA | GAT | GAT | AAA | CCT | CTA | GCA | GTA | 1176 |
| Met | Val | Ala | Tyr | Thr 215 | Val | Lys | Pro | Val | Asp 220 | Asp | Lys | Pro | Leu | Ala 225 | Val | |
| TCA | AAC | TCT | TCT | GAG | CTG | ACG | GAA | CAG | GCT | ATT | TTT | GAT | AAG | TTG | GTT | 1224 |
| Ser | Asn | Ser | Ser 230 | Glu | Leu | Thr | Glu | Gln 235 | Ala | Ile | Phe | Asp | Lys 240 | Leu | Val | |
| GTC | GAT | AAG | TCT | GCT | AAA | ACA | ACT | TCA | AAT | AGC | GCT | CTT | GTA | ATT | GAT | 1272 |
| Val | Asp | Lys 245 | Ser | Ala | Lys | Thr | Thr 250 | Ser | Asn | Ser | Ala | Leu 255 | Val | Ile | Asp | |
| TCT | AGC | AAC | TAC | AAA | CAT | TCA | ATT | GCA | GGT | TAT | CGT | ACC | GTA | AAT | TCT | 1320 |
| Ser | Ser | Asn 260 | Tyr | Lys | His | Ser | Ile 265 | Ala | Gly | Tyr | Arg | Thr 270 | Val | Asn | Ser | |
| GAT | GGC | ACA | AAA | ACA | GAA | ACA | GTA | GAG | GAA | ACA | AAT | CTA | TCT | GAT | TTC | 1368 |
| Asp 275 | Gly | Thr | Lys | Thr | Glu 280 | Thr | Val | Glu | Glu | Thr 285 | Asn | Leu | Ser | Asp | Phe 290 | |
| CCA | ACT | GAA | GGT | AAA | TAC | GAA | GTT | CGA | GTA | AAA | ACA | ACC | AAT | GTT | TAC | 1416 |
| Pro | Thr | Glu | Gly | Lys 295 | Tyr | Glu | Val | Arg | Val 300 | Lys | Thr | Thr | Asn | Val 305 | Tyr | |
| GGT | CAA | ACT | ATC | TAC | AAC | TGG | ATT | CCT | GTA | AAT | GCC | TAT | AAG | TTG | GAC | 1464 |
| Gly | Gln | Thr | Ile 310 | Tyr | Asn | Trp | Ile | Pro 315 | Val | Asn | Ala | Tyr | Lys 320 | Leu | Asp | |
| ACA | GCG | AAG | GAT | GCT | GAA | ATT | CGG | AAG | TAT | ACA | GAC | AAC | CAA | GCC | CCA | 1512 |
| Thr | Ala | Lys 325 | Asp | Ala | Glu | Ile | Arg 330 | Lys | Tyr | Thr | Asp | Asn 335 | Gln | Ala | Pro | |
| ATT | CAT | GCT | ATA | ATG | CAA | ATT | GGT | CAA | GCT | GGA | GAA | AAG | GCA | GCA | GTT | 1560 |
| Ile | His 340 | Ala | Ile | Met | Gln | Ile 345 | Gly | Gln | Ala | Gly | Glu 350 | Lys | Ala | Ala | Val | |
| ATA | TTG | AAG | GAT | ATT | CCA | TCC | GAT | TTC | AGT | ATT | GAA | AAC | TTC | AAT | TTG | 1608 |
| Ile 355 | Leu | Lys | Asp | Ile | Pro 360 | Ser | Asp | Phe | Ser | Ile 365 | Glu | Asn | Phe | Asn | Leu 370 | |
| AAA | GAT | GGT | GTA | GCA | GAT | GAG | CTT | GCT | AAA | CGT | AAC | TTG | GAA | TTT | GTA | 1656 |
| Lys | Asp | Gly | Val | Ala 375 | Asp | Glu | Leu | Ala | Lys 380 | Arg | Asn | Leu | Glu | Phe 385 | Val | |

```
AGA AAT GAT GCA GTG GCG ACA ACT GAT ACT GAT GGA GAT GGC GCC AAA   1704
Arg Asn Asp Ala Val Ala Thr Thr Asp Thr Asp Gly Asp Gly Ala Lys
            390                 395                 400

GAA GGA ATT GTT GGA TAT ATT CAA CCA AAA ACT GGC GGT GCA AAC AGT   1752
Glu Gly Ile Val Gly Tyr Ile Gln Pro Lys Thr Gly Gly Ala Asn Ser
        405                 410                 415

GGG GTA GCC ACT TAT ACA GGA TCA AAT AAT CTT ACT TAT GGC TTC ACT   1800
Gly Val Ala Thr Tyr Thr Gly Ser Asn Asn Leu Thr Tyr Gly Phe Thr
420                 425                 430

TAC AAA GCT GTT GAG ACA AAA GAT AAG GCG AAT GCC ACA GAG GCT AAA   1848
Tyr Lys Ala Val Glu Thr Lys Asp Lys Ala Asn Ala Thr Glu Ala Lys
435                 440                 445                 450

ACT CTC GAA TTA GAT TAC ACC ATC TTA TTC ATA GAT ACT AAA GCA CCA   1896
Thr Leu Glu Leu Asp Tyr Thr Ile Leu Phe Ile Asp Thr Lys Ala Pro
                455                 460                 465

GTC ATG ACA CCT AAA TCA GAG TAC ATC CGT TTT GTT GGT GAA GAG TAT   1944
Val Met Thr Pro Lys Ser Glu Tyr Ile Arg Phe Val Gly Glu Glu Tyr
            470                 475                 480

ACG GTT AGC GTC CCA GGT ACG GAT AAC GCC TTC CTT AAT ACC GGC AAA   1992
Thr Val Ser Val Pro Gly Thr Asp Asn Ala Phe Leu Asn Thr Gly Lys
        485                 490                 495

CTA AAT GGA ACT CTC TCA ATT TTG AAA GAT GGA GAG TCA GGT TCT CTT   2040
Leu Asn Gly Thr Leu Ser Ile Leu Lys Asp Gly Glu Ser Gly Ser Leu
500                 505                 510

GTA TCA TCA GAC TTA GGT ACA AAC ACT AAG ATT ACT TCA GAA CTG GAT   2088
Val Ser Ser Asp Leu Gly Thr Asn Thr Lys Ile Thr Ser Glu Leu Asp
515                 520                 525                 530

CCT ACG GGA GCA ACT GCA AAC CAA GGA GAT GAC GGT CAA TCT TCA ACT   2136
Pro Thr Gly Ala Thr Ala Asn Gln Gly Asp Asp Gly Gln Ser Ser Thr
                535                 540                 545

AAG TTT AAC GTT AAG ATT ACA GGT ACC GGA CCT GCT ACA GAA GGT ACC   2184
Lys Phe Asn Val Lys Ile Thr Gly Thr Gly Pro Ala Thr Glu Gly Thr
            550                 555                 560

GGC ACT TAT AAG CTT CGT GTT GGA GAA GAT AAC TAT CCT TTT GGT CCA   2232
Gly Thr Tyr Lys Leu Arg Val Gly Glu Asp Asn Tyr Pro Phe Gly Pro
        565                 570                 575

GAG GGG AAA CTT GTT GAT GGA AAT AAA CCA GAA AAT GTA GGT TTG ACA   2280
Glu Gly Lys Leu Val Asp Gly Asn Lys Pro Glu Asn Val Gly Leu Thr
580                 585                 590

TCT GTA AAA GTT ACC TTC GTA AAA CAT GCT ACG GTG TCA ACA CCA GTT   2328
Ser Val Lys Val Thr Phe Val Lys His Ala Thr Val Ser Thr Pro Val
595                 600                 605                 610

TCT GTT GAA AAT CCA GCT AAC TTA ACG CCA GAA GAA AAA GCC GCA GTT   2376
Ser Val Glu Asn Pro Ala Asn Leu Thr Pro Glu Glu Lys Ala Ala Val
                615                 620                 625

ATT GCT CAA ATC AAG AAA GAC AAC GCA GAC AAC GAA AGA TTG AAG GGC   2424
Ile Ala Gln Ile Lys Lys Asp Asn Ala Asp Asn Glu Arg Leu Lys Gly
            630                 635                 640

TTG CCA GAT TCA GCA TTT ACA GTT AAC TCA GAT GGT ACT GTG TCA GTT   2472
Leu Pro Asp Ser Ala Phe Thr Val Asn Ser Asp Gly Thr Val Ser Val
        645                 650                 655

GAC TAC AGT GCC GGT GGT GTC AAT GTT GAT GGT GCG ACA GAC ATT ATT   2520
Asp Tyr Ser Ala Gly Gly Val Asn Val Asp Gly Ala Thr Asp Ile Ile
660                 665                 670

AAG AAT GCT ACC ACA AAC TTG GCA GAT ACA CGG AAT GAA GCA AAA GCA   2568
Lys Asn Ala Thr Thr Asn Leu Ala Asp Thr Arg Asn Glu Ala Lys Ala
675                 680                 685                 690

GAA ATC GAC ACA AAA TTA GCT GAA CAT AAA AAA GCT ATC GAA GCA AAA   2616
Glu Ile Asp Thr Lys Leu Ala Glu His Lys Lys Ala Ile Glu Ala Lys
                695                 700                 705
```

| | | | | | | | | | | | | | | | | |
|---|---|---|---|---|---|---|---|---|---|---|---|---|---|---|---|---|
| CGG | GAT | GAA | GCG | TTT | TCT | AAA | ATT | GAT | GAT | GAC | ATT | TCC | TTG | AGA | GCA | 2664 |
| Arg | Asp | Glu | Ala | Phe | Ser | Lys | Ile | Asp | Asp | Asp | Ile | Ser | Leu | Arg | Ala | |
| | | | 710 | | | | | 715 | | | | | 720 | | | |
| GAA | CAG | AGA | CAG | GCT | GCT | AAG | GAT | GCC | GTT | GCT | GCA | GCT | GCT | GGG | GAT | 2712 |
| Glu | Gln | Arg | Gln | Ala | Ala | Lys | Asp | Ala | Val | Ala | Ala | Ala | Ala | Gly | Asp | |
| | | 725 | | | | | 730 | | | | | 735 | | | | |
| GCT | TTG | AAA | GAA | TTA | GAC | AAC | AAG | GCG | ACA | GAA | GCA | AAA | GAA | AAA | ATT | 2760 |
| Ala | Leu | Lys | Glu | Leu | Asp | Asn | Lys | Ala | Thr | Glu | Ala | Lys | Glu | Lys | Ile | |
| | 740 | | | | | 745 | | | | | 750 | | | | | |
| GAT | AAA | GCT | ACG | ACG | GCC | TCA | GAA | ATC | AAT | GAT | GCT | AAG | ACT | AAT | GGT | 2808 |
| Asp | Lys | Ala | Thr | Thr | Ala | Ser | Glu | Ile | Asn | Asp | Ala | Lys | Thr | Asn | Gly | |
| 755 | | | | | 760 | | | | | 765 | | | | | 770 | |
| GAG | ATT | AAT | CTG | GAC | AGT | GCA | GAA | GCA | GTA | GGC | GAA | AAA | GCT | ATT | AAC | 2856 |
| Glu | Ile | Asn | Leu | Asp | Ser | Ala | Glu | Ala | Val | Gly | Glu | Lys | Ala | Ile | Asn | |
| | | | | 775 | | | | | 780 | | | | | 785 | | |
| CAG | GCG | AAG | GAA | AAA | GAA | CTG | GCA | AAA | GCA | GAA | GTT | GAA | AAC | AAA | GCA | 2904 |
| Gln | Ala | Lys | Glu | Lys | Glu | Leu | Ala | Lys | Ala | Glu | Val | Glu | Asn | Lys | Ala | |
| | | | 790 | | | | | 795 | | | | | 800 | | | |
| TTC | GAG | GCA | TTG | GAA | AAA | GTT | AAC | AAT | AAT | CCA | AAC | TTG | TTA | GAA | GAA | 2952 |
| Phe | Glu | Ala | Leu | Glu | Lys | Val | Asn | Asn | Asn | Pro | Asn | Leu | Leu | Glu | Glu | |
| | | 805 | | | | | 810 | | | | | 815 | | | | |
| GAG | AAA | AAA | GCA | TAC | TTT | GAT | GAT | ATT | AAA | GAA | TCT | AAA | GAA | GTT | GCA | 3000 |
| Glu | Lys | Lys | Ala | Tyr | Phe | Asp | Asp | Ile | Lys | Glu | Ser | Lys | Glu | Val | Ala | |
| | 820 | | | | | 825 | | | | | 830 | | | | | |
| GTT | GAG | AAA | ATC | AAT | AAT | GCT | GAA | AAT | ACT | GCT | GAA | ATT | ACG | GCA | GCA | 3048 |
| Val | Glu | Lys | Ile | Asn | Asn | Ala | Glu | Asn | Thr | Ala | Glu | Ile | Thr | Ala | Ala | |
| 835 | | | | | 840 | | | | | 845 | | | | | 850 | |
| ATT | GAC | GAA | GCG | GAA | ATT | GCA | TAC | AAT | GAA | GAT | GTT | ATT | AAC | GCA | GCC | 3096 |
| Ile | Asp | Glu | Ala | Glu | Ile | Ala | Tyr | Asn | Glu | Asp | Val | Ile | Asn | Ala | Ala | |
| | | | 855 | | | | | 860 | | | | | 865 | | | |
| CAA | CTT | GAT | GCT | TTG | AAT | AAG | CTT | GAA | AAA | GAT | AGC | GAA | GAA | ACT | AAG | 3144 |
| Gln | Leu | Asp | Ala | Leu | Asn | Lys | Leu | Glu | Lys | Asp | Ser | Glu | Glu | Thr | Lys | |
| | | | 870 | | | | | 875 | | | | | 880 | | | |
| GCA | GCT | ATT | GAT | GCT | AAT | CCA | AAC | TTA | ACT | CCG | GAA | GAG | AAA | GCG | AAA | 3192 |
| Ala | Ala | Ile | Asp | Ala | Asn | Pro | Asn | Leu | Thr | Pro | Glu | Glu | Lys | Ala | Lys | |
| | | 885 | | | | | 890 | | | | | 895 | | | | |
| GCT | ATT | GCT | AAG | GTA | GAA | GAG | CTT | GTT | AAT | AAT | GCT | GAA | TCT | GAC | ATT | 3240 |
| Ala | Ile | Ala | Lys | Val | Glu | Glu | Leu | Val | Asn | Asn | Ala | Glu | Ser | Asp | Ile | |
| | | 900 | | | | | 905 | | | | | 910 | | | | |
| TTG | TCG | AAG | CCT | ACC | CCA | GAA | ACA | GTT | CAA | GCA | GTG | GAG | GAT | AAG | GCT | 3288 |
| Leu | Ser | Lys | Pro | Thr | Pro | Glu | Thr | Val | Gln | Ala | Val | Glu | Asp | Lys | Ala | |
| 915 | | | | | 920 | | | | | 925 | | | | | 930 | |
| GAC | AAA | GAT | CTT | GCC | AAA | GTA | GAA | CTT | CAA | GCA | GCA | GCA | GAC | GGT | GCG | 3336 |
| Asp | Lys | Asp | Leu | Ala | Lys | Val | Glu | Leu | Gln | Ala | Ala | Ala | Asp | Gly | Ala | |
| | | | | 935 | | | | | 940 | | | | | 945 | | |
| AAG | AAA | GGC | ATT | GAA | GCA | AAT | CCG | AAT | TTG | ACT | CCA | GAA | GAG | AAA | GAT | 3384 |
| Lys | Lys | Gly | Ile | Glu | Ala | Asn | Pro | Asn | Leu | Thr | Pro | Glu | Glu | Lys | Asp | |
| | | | 950 | | | | | 955 | | | | | 960 | | | |
| GTA | GCT | AAG | AAG | GCA | GTA | GAA | GAC | GCG | GTT | AAG | GTG | GCG | ACA | GAC | GCT | 3432 |
| Val | Ala | Lys | Lys | Ala | Val | Glu | Asp | Ala | Val | Lys | Val | Ala | Thr | Asp | Ala | |
| | | 965 | | | | | 970 | | | | | 975 | | | | |
| ATT | GAT | AAG | GCG | TCA | ACT | CCA | ACC | GAA | GTT | GAC | ACA | GCG | ACA | AGC | GAT | 3480 |
| Ile | Asp | Lys | Ala | Ser | Thr | Pro | Thr | Glu | Val | Asp | Thr | Ala | Thr | Ser | Asp | |
| | 980 | | | | | 985 | | | | | 990 | | | | | |
| GGA | GTG | AAG | GCT | ATT | GAT | GCA | GAA | GAG | TTT | AAA | GCT | ACT | CAG | AAA | GAT | 3528 |
| Gly | Val | Lys | Ala | Ile | Asp | Ala | Glu | Glu | Phe | Lys | Ala | Thr | Gln | Lys | Asp | |
| 995 | | | | | 1000 | | | | | 1005 | | | | | 1010 | |
| GCT | AAG | AAC | AAG | ATT | GCC | AAA | GAA | GCA | GAA | TCA | GCT | AAG | AAA | GCG | ATT | 3576 |
| Ala | Lys | Asn | Lys | Ile | Ala | Lys | Glu | Ala | Glu | Ser | Ala | Lys | Lys | Ala | Ile | |
| | | | | 1015 | | | | | 1020 | | | | | 1025 | | |

| | | | | | | | | | | | | | | | | |
|---|---|---|---|---|---|---|---|---|---|---|---|---|---|---|---|---|
| GAC | GAC | AAT | CCA | AAC | TTG | ACT | CCA | GAT | GAG | AAG | GAA | TCA | GCT | AAG | AAT | 3624 |
| Asp | Asp | Asn | Pro | Asn | Leu | Thr | Pro | Asp | Glu | Lys | Glu | Ser | Ala | Lys | Asn | |
| | | | 1030 | | | | 1035 | | | | 1040 | | | | | |
| GCA | GTG | GAA | GAG | GCG | GCT | AAG | GTA | GCA | ACA | GCC | GCT | ATT | GAT | AAA | GCA | 3672 |
| Ala | Ser | Glu | Glu | Ala | Ala | Lys | Val | Ala | Thr | Ala | Ala | Ile | Asp | Lys | Ala | |
| | 1045 | | | | 1050 | | | | 1055 | | | | | | | |
| TCA | ACT | CCA | GAT | GCA | GTT | CAA | GTA | GAA | GAG | GAC | AAA | GGT | GTA | GCA | GCT | 3720 |
| Ser | Thr | Pro | Asp | Ala | Val | Gln | Val | Glu | Glu | Asp | Lys | Gly | Val | Ala | Ala | |
| | 1060 | | | | 1065 | | | | 1070 | | | | | | | |
| ATC | AAT | TTG | ATT | ACT | GCC | AAG | GCA | GAT | GCT | AAA | GGT | GTC | ATT | GCT | GCT | 3768 |
| Ile | Asn | Leu | Ile | Thr | Ala | Lys | Ala | Asp | Ala | Lys | Gly | Val | Ile | Ala | Ala | |
| 1075 | | | | 1080 | | | | 1085 | | | | 1090 | | | | |
| AAG | TTG | GCA | GAT | GAA | ATC | AAG | AAG | CTC | GAA | GAT | AAG | CAA | GCA | GAA | GCA | 3816 |
| Lys | Leu | Ala | Asp | Glu | Ile | Lys | Lys | Leu | Glu | Asp | Lys | Gln | Ala | Glu | Ala | |
| | 1095 | | | | 1100 | | | | 1105 | | | | | | | |
| GAA | AAA | GCT | ATC | GAT | GCG | TCA | ACT | ATG | ACT | AAT | GAG | GAG | AAA | GCA | ATC | 3864 |
| Glu | Lys | Ala | Ile | Asp | Ala | Ser | Thr | Met | Thr | Asn | Glu | Glu | Lys | Ala | Ile | |
| | 1110 | | | | 1115 | | | | 1120 | | | | | | | |
| GCT | AAG | AAG | GCT | CTT | CAA | GAT | GTT | GTA | GAT | AAA | GGA | AAA | GCA | GAG | CTT | 3912 |
| Ala | Lys | Lys | Ala | Leu | Gln | Asp | Val | Val | Asp | Lys | Gly | Lys | Ala | Glu | Leu | |
| | 1125 | | | | 1135 | | | | 1135 | | | | | | | |
| GAA | GAC | GCA | GCT | AGG | GTA | GCA | ACA | AAT | GAG | ATT | CAT | GAA | GCT | ACT | ACT | 3960 |
| Glu | Asp | Ala | Ala | Arg | Val | Ala | Thr | Asn | Glu | Ile | His | Glu | Ala | Thr | Thr | |
| | 1140 | | | | 1145 | | | | 1150 | | | | | | | |
| ACA | GAA | AAA | GCG | AAA | GCG | GCG | GAA | CTT | GCT | GGC | GAA | AAG | AGC | TTG | ACA | 4008 |
| Thr | Glu | Lys | Ala | Lys | Ala | Ala | Glu | Leu | Ala | Gly | Glu | Lys | Ser | Leu | Thr | |
| 1155 | | | | 1165 | | | | 1165 | | | | 1170 | | | | |
| GAC | ACA | GGT | AAA | GAA | GCT | AGA | GAT | GCA | GTT | GAA | TTG | GCT | AAG | GAT | AAA | 4056 |
| Asp | Thr | Gly | Lys | Glu | Ala | Arg | Asp | Ala | Val | Glu | Leu | Ala | Lys | Asp | Lys | |
| | | | 1175 | | | | 1180 | | | | 1185 | | | | | |
| GAA | TTA | GCT | AAG | GAA | GCA | ATC | CGA | ACA | GAA | GAA | GAA | GAA | GCT | ACT | AAA | 4104 |
| Glu | Leu | Ala | Lys | Glu | Ala | Ile | Arg | Thr | Glu | Glu | Glu | Glu | Ala | Thr | Lys | |
| | | 1190 | | | | 1195 | | | | 1200 | | | | | | |
| ATA | GTA | GAG | AAA | CTT | GCA | GAA | GAT | ACG | CGC | AAA | GCT | ATC | GAG | GAC | AAT | 4152 |
| Ile | Val | Glu | Lys | Leu | Ala | Glu | Asp | Thr | Arg | Lys | Ala | Ile | Glu | Asp | Asn | |
| | 1205 | | | | 1210 | | | | 1215 | | | | | | | |
| CCA | AAC | TTG | TCA | GAT | GAA | GAT | AAG | CAA | GCG | GAA | ATT | AAA | AAG | CTA | ACT | 4200 |
| Pro | Asn | Leu | Ser | Asp | Glu | Asp | Lys | Gln | Ala | Glu | Ile | Lys | Lys | Leu | Thr | |
| 1220 | | | | 1225 | | | | 1230 | | | | | | | | |
| GAC | GCT | GTG | GCA | AAA | ACT | TTA | GCA | ACC | ATT | CGT | GAC | AAT | GCA | GAT | AAG | 4248 |
| Asp | Ala | Val | Ala | Lys | Thr | Leu | Ala | Thr | Ile | Arg | Asp | Asn | Ala | Asp | Lys | |
| 1235 | | | | 1240 | | | | 1245 | | | | 1250 | | | | |
| CGT | ACG | CAA | GAA | GCA | GAA | AAA | GCT | CAA | GCC | CTA | GCA | GAT | CTT | GAA | AAA | 4296 |
| Arg | Thr | Gln | Glu | Ala | Glu | Lys | Ala | Gln | Ala | Leu | Ala | Asp | Leu | Glu | Lys | |
| | | | 1255 | | | | 1260 | | | | 1265 | | | | | |
| GCT | AAA | GAA | ACA | CAG | AAA | ATT | GCA | GAT | AAA | GCT | GCG | ATT | GAT | AGG | TTG | 4344 |
| Ala | Lys | Glu | Thr | Gln | Lys | Ile | Ala | Asp | Lys | Ala | Ala | Ile | Asp | Arg | Leu | |
| | | 1270 | | | | 1275 | | | | 1280 | | | | | | |
| ACT | ATA | CTT | GTG | AAA | GAT | GGT | GAG | CTT | GAA | GCT | ACT | AAA | CAA | GAT | GCT | 4392 |
| Thr | Ile | Leu | Val | Lys | Asp | Gly | Glu | Leu | Glu | Ala | Thr | Lys | Gln | Asp | Ala | |
| | | 1285 | | | | 1290 | | | | 1295 | | | | | | |
| AAG | AAC | AAG | ATT | GCT | AAA | GAT | GCA | GCC | GCT | GCT | AAA | GAA | GCA | ATT | GCA | 4440 |
| Lys | Asn | Lys | Ile | Ala | Lys | Asp | Ala | Ala | Ala | Ala | Lys | Glu | Ala | Ile | Ala | |
| | 1300 | | | | 1305 | | | | 1310 | | | | | | | |
| AGC | AAT | CCA | AAC | TTG | ACA | GAC | GCA | GAG | AAG | AAA | ACC | TTC | ACC | GAT | GCG | 4488 |
| Ser | Asn | Pro | Asn | Leu | Thr | Asp | Ala | Glu | Lys | Lys | Thr | Phe | Thr | Asp | Ala | |
| 1315 | | | | 1320 | | | | 1325 | | | | 1330 | | | | |
| GTA | GAT | GCA | GAA | GTA | GCC | AAA | GCT | AAC | GAC | GCA | ATT | TCA | GCT | GCA | ACC | 4536 |
| Val | Asp | Ala | Glu | Val | Ala | Lys | Ala | Asn | Asp | Ala | Ile | Ser | Ala | Ala | Thr | |
| | | 1335 | | | | 1340 | | | | 1345 | | | | | | |

| | | | | | | | | | | | | | | | | |
|---|---|---|---|---|---|---|---|---|---|---|---|---|---|---|---|---|
| AGC | CCA | GCA | GAT | GTT | CAA | AAA | GAA | GAG | GAT | GCA | GGT | GTT | GCA | GCC | ATT | 4584 |
| Ser | Pro | Ala | Asp | Val | Gln | Lys | Glu | Glu | Asp | Ala | Gly | Val | Ala | Ala | Ile | |
| | | | 1350 | | | | 1355 | | | | | 1360 | | | | |
| GCA | GAA | GAT | GTT | CTT | GAC | GCA | GCT | AAA | CAA | GAT | GCT | AAG | AAT | AAG | ATT | 4632 |
| Ala | Glu | Asp | Val | Leu | Asp | Ala | Ala | Lys | Gln | Asp | Ala | Lys | Asn | Lys | Ile | |
| | | | 1365 | | | | 1370 | | | | | 1375 | | | | |
| GCT | AAA | GAT | GCA | GCC | GCT | GCT | AAA | GAA | GCA | ATT | GGC | TCC | AAT | CCA | AAC | 4680 |
| Ala | Lys | Asp | Ala | Ala | Ala | Ala | Lys | Glu | Ala | Ile | Gly | Ser | Asn | Pro | Asn | |
| | | 1380 | | | | | 1385 | | | | | 1390 | | | | |
| TTG | ACA | GAC | GCA | GAG | AAG | AAA | ACC | TTC | ACC | GAT | GCG | GTA | GAT | GCA | GAA | 4728 |
| Leu | Thr | Asp | Ala | Glu | Lys | Lys | Thr | Phe | Thr | Asp | Ala | Val | Asp | Ala | Glu | |
| 1395 | | | | | 1400 | | | | | 1405 | | | | | 1410 | |
| GTA | GCC | AAA | GCT | AAC | GAC | GCA | ATT | TCA | GCT | GCA | ACC | AGC | CCA | GCA | GAT | 4776 |
| Val | Ala | Lys | Ala | Asn | Asp | Ala | Ile | Ser | Ala | Ala | Thr | Ser | Pro | Ala | Asp | |
| | | | | 1415 | | | | | 1420 | | | | | 1425 | | |
| GTT | CAA | AAA | GAA | GAG | GAT | GCA | GGT | GTT | GCA | GCC | ATT | GCA | GAA | GAT | GTT | 4824 |
| Val | Gln | Lys | Glu | Glu | Asp | Ala | Gly | Val | Ala | Ala | Ile | Ala | Glu | Asp | Val | |
| | | | 1430 | | | | | 1435 | | | | | 1440 | | | |
| CTT | GAC | GCA | GCT | AAA | CAA | GAT | GCT | AAG | AAT | AAG | ATT | GCT | AAA | GAA | TCC | 4872 |
| Leu | Asp | Ala | Ala | Lys | Gln | Asp | Ala | Lys | Asn | Lys | Ile | Ala | Lys | Glu | Ser | |
| | | | 1445 | | | | | 1450 | | | | | 1455 | | | |
| GAC | GCT | GCT | AAG | TCA | GCC | ATT | GAC | GCG | AAT | CCA | AAC | TTG | ACA | GAT | GCA | 4920 |
| Asp | Ala | Ala | Lys | Ser | Ala | Ile | Asp | Ala | Asn | Pro | Asn | Leu | Thr | Asp | Ala | |
| | | | 1460 | | | | | 1465 | | | | 1470 | | | | |
| GAG | AAG | GAA | TCA | GCT | AAG | AAA | GCA | GTT | GAT | GCT | GAT | GCT | AAA | GCT | GCG | 4968 |
| Glu | Lys | Glu | Ser | Ala | Lys | Lys | Ala | Val | Asp | Ala | Asp | Ala | Lys | Ala | Ala | |
| 1475 | | | | | 1480 | | | | | 1485 | | | | | 1490 | |
| ACA | GAT | GCA | ATT | GAT | GCT | TCA | ACA | AGT | CCA | GTC | GAA | GCG | CAA | TCG | GCA | 5016 |
| Thr | Asp | Ala | Ile | Asp | Ala | Ser | Thr | Ser | Pro | Val | Glu | Ala | Gln | Ser | Ala | |
| | | | | 1495 | | | | | 1500 | | | | | 1505 | | |
| GAG | GAC | AAA | GGC | GTA | GGT | TCA | ATC | GCC | CAA | GAT | GTT | CTT | GAC | GCA | GCG | 5064 |
| Glu | Asp | Lys | Gly | Val | Gly | Ser | Ile | Ala | Gln | Asp | Val | Leu | Asp | Ala | Ala | |
| | | | 1510 | | | | | 1515 | | | | | 1520 | | | |
| AAA | CAA | GAT | GCT | AAG | AAC | AAG | ATT | GCC | AAA | GAA | GTT | GCC | GCA | GCT | AAA | 5112 |
| Lys | Gln | Asp | Ala | Lys | Asn | Lys | Ile | Ala | Lys | Glu | Val | Ala | Ala | Ala | Lys | |
| | | | 1525 | | | | | 1530 | | | | | 1535 | | | |
| GAA | GCA | ATT | GAT | GCC | AAT | CCG | AAC | TTA | TCA | GAT | GCA | GAG | AAG | GAA | GCT | 5160 |
| Glu | Ala | Ile | Asp | Ala | Asn | Pro | Asn | Leu | Ser | Asp | Ala | Glu | Lys | Glu | Ala | |
| | | | 1540 | | | | 1545 | | | | | 1550 | | | | |
| TCT | AAG | AAA | GCG | GTA | GAT | GCA | GAT | GCT | AAA | GCT | ACG | ACA | GAT | GCA | ATT | 5208 |
| Ser | Lys | Lys | Ala | Val | Asp | Ala | Asp | Ala | Lys | Ala | Thr | Thr | Asp | Ala | Ile | |
| 1555 | | | | | 1560 | | | | | 1565 | | | | | 1570 | |
| GAT | GCT | TCA | ACA | AGT | CCA | GTC | GAA | GCG | CAA | TCG | GCA | GAG | GAC | AAA | GGC | 5256 |
| Asp | Ala | Ser | Thr | Ser | Pro | Val | Glu | Ala | Gln | Ser | Ala | Glu | Asp | Lys | Gly | |
| | | | | 1575 | | | | | 1580 | | | | | 1585 | | |
| GTA | GGT | TCA | ATC | GCC | CAA | GAT | GTT | CTT | GAC | GCA | GCG | AAA | CAA | GAT | GCT | 5304 |
| Val | Gly | Ser | Ile | Arg | Gln | Asp | Val | Leu | Asp | Ala | Ala | Lys | Gln | Asp | Ala | |
| | | | 1590 | | | | | 1595 | | | | | 1600 | | | |
| AAG | AAT | AAG | ATT | GCT | AAA | GAA | TCC | GAC | GCT | GCT | AAG | TCA | GCC | ATT | GAC | 5352 |
| Lys | Asn | Lys | Ile | Ala | Lys | Glu | Ser | Asp | Ala | Ala | Lys | Ser | Ala | Ile | Asp | |
| | | | 1605 | | | | | 1610 | | | | | 1615 | | | |
| GCG | AAT | CCA | AAC | TTG | ACA | GAT | GCA | GAG | AAG | GAA | TCA | GCT | AAG | AAA | GCG | 5400 |
| Ala | Asn | Pro | Asn | Leu | Thr | Asp | Ala | Glu | Lys | Glu | Ser | Ala | Lys | Lys | Ala | |
| | 1620 | | | | | 1625 | | | | | 1630 | | | | | |
| GTA | GAT | GCA | GAT | GCT | AAA | GCT | GCG | ACA | GAT | GCA | ATT | GAT | GCT | TCA | ACA | 5448 |
| Val | Asp | Ala | Asp | Ala | Lys | Ala | Ala | Thr | Asp | Ala | Ile | Asp | Ala | Ser | Thr | |
| 1635 | | | | | 1640 | | | | | 1645 | | | | | 1650 | |
| AGT | CCA | GTC | GAA | GCG | CAA | TCG | GCA | GAG | GAC | AAA | GGC | GTA | GGC | GCC | ATC | 5496 |
| Ser | Pro | Val | Glu | Ala | Gln | Ser | Ala | Glu | Asp | Lys | Gly | Val | Gly | Ala | Ile | |
| | | | | 1655 | | | | | 1660 | | | | | 1665 | | |

| | | | | | | | | | | | | | | | |
|---|---|---|---|---|---|---|---|---|---|---|---|---|---|---|---|
| GCC | AAA | GAC | ATT | CTT | GAT | GCC | GCG | AAA | CAA | GAT | GCT | AAG | AAC | AAG | ATT | 5544
| Ala | Lys | Asp | Ile | Leu | Asp | Ala | Ala | Lys | Gln | Asp | Ala | Lys | Asn | Lys | Ile |
| | | | 1670 | | | | | 1675 | | | | | 1680 | | |
| GCT | AAA | GAG | GCA | GAA | TCC | GCT | AAG | TCA | GTC | ATT | GAC | TCC | AAT | CCG | AAC | 5592
| Ala | Lys | Glu | Ala | Glu | Ser | Ala | Lys | Ser | Val | Ile | Asp | Ser | Asn | Pro | Asn |
| | | 1685 | | | | | 1690 | | | | | 1695 | | | |
| TTG | ACA | GAT | GCA | GCT | AAG | GAA | GCG | GCT | AAA | TCT | GAA | ATT | GAT | AAA | GCT | 5640
| Leu | Thr | Asp | Ala | Ala | Lys | Glu | Ala | Ala | Lys | Ser | Glu | Ile | Asp | Lys | Ala |
| | 1700 | | | | | 1705 | | | | | 1710 | | | | |
| GTT | GAG | GAA | GCG | ATT | GTT | TTA | ATC | AAT | GGT | GTT | AGA | ACT | TAT | CAA | GAG | 5688
| Val | Glu | Glu | Ala | Ile | Val | Leu | Ile | Asn | Gly | Val | Arg | Thr | Tyr | Gln | Glu |
| 1715 | | | | | 1720 | | | | | 1725 | | | | | 1730 |
| TTG | GAA | AAA | ATC | AAA | CTT | CCA | ATG | GCA | GCT | CTA | ATT | AAA | CCA | GCT | GCG | 5736
| Leu | Glu | Lys | Ile | Lys | Leu | Pro | Met | Ala | Ala | Leu | Ile | Lys | Pro | Ala | Ala |
| | | | | 1735 | | | | | 1740 | | | | | 1745 | |
| AAA | GTA | ACA | CCA | GTG | GTT | GAT | CCA | AAT | AAC | TTG | ACT | GAA | AAA | GAA | ATT | 5784
| Lys | Val | Thr | Pro | Val | Val | Asp | Pro | Asn | Asn | Leu | Thr | Glu | Lys | Glu | Ile |
| | | | 1750 | | | | | 1755 | | | | | 1760 | | |
| GCT | CGT | ATC | AAG | GCA | TTC | CTT | AAA | GAG | AAC | AAT | AAC | CTC | CCA | TAA | | 5829
| Ala | Arg | Ile | Lys | Ala | Phe | Leu | Lys | Glu | Asn | Asn | Asn | Leu | Pro | | | |
| | | | 1765 | | | | | 1770 | | | | | 1775 | | | |

| | | | | |
|---|---|---|---|---|
| GGAACAGAGA | TTAATGTTTC | TAAAGATGCT | TCAGTGACAA | TTAAATATCC | AGATGGAACT | 5889
| ATTGATTTGC | TATCACCAGT | AGAAGTTGTG | AAGCAGGCAG | ATAAAACTGC | TCCTACGGTC | 5949
| GCAAATGATG | GCAAAGGTAA | TATTGTGATT | GTACCGTCTG | AAAAAGCTGT | TGAGCTTGTT | 6009
| GTTCATACG | TAGATAACAA | TGGTAAGTCG | CAAACTGTAG | TTGTTACGAA | AGGTACGGAT | 6069
| GGTTTATGGA | CAGCAAGTAA | TACAGTGGTG | ATTGTGGACC | CTGTGACTGG | GCAAGTAATC | 6129
| GTTCCAGGTT | CTGTTATTAA | GCCAGGTACA | GTTGTTACAG | CATACTCTAA | AGACGAGGTT | 6189
| GGAAATAGTT | CTGATTCAGC | AGAAGCTGAA | GTTGTAGCAG | TAGACGAAAA | TAATTCTGCA | 6249
| GCAGGAGTGA | AAGTTAAATC | AGTTACTACA | AATGCTAATA | ATGTTGAGAA | GAAAGCTAAG | 6309
| CAATTACCGA | ATACTGGTGA | GGAAGCAAAT | TCAGCAACTT | CACTCGGATT | AGTAGCTCTT | 6369
| GGACTCGGAT | TAGCACTTCT | TGCAGCAAAG | AGAAGAAGAG | ACGAAGAAGC | TTAAGATAAG | 6429
| CTCTTCCTCA | GAACTCTTTT | GGAAGCCGCA | ATTTTCCTAG | AAGATAGTAG | TATGATACTC | 6489
| TTTCATAGCA | AGGAAATTCC | CTCGCTATGA | TTGGTAGGTA | TCAGTTATTA | TCTATCGAAC | 6549
| CCCC<u>AAAATC</u> | <u>CAAAGTCATT</u> | C<u>GACTTTGGA</u> | <u>TTTTTTTGAT</u> | ACGACATGCT | CGTCATACCT | 6609
| A<u>AAAAACAGC</u> | <u>CTTCTCTTGC</u> | C<u>GAGAGGCTG</u> | <u>TTTTT</u>CATGC | TTTTAATCTA | AAAGTCTGCG | 6669
| GACGTTTTTT | CAATAAAATC | CAGTAACCGA | TGCTAACATA | GGCAATCATA | GCTAGGGAAA | 6729
| CCAGCAGGAT | ATAGG | | | | | 6744

( 2 ) INFORMATION FOR SEQ ID NO:3:

( i ) SEQUENCE CHARACTERISTICS:
        ( A ) LENGTH: 4118 base pairs
        ( B ) TYPE: Nucleic acid with corresponding amino acids
        ( C ) STRANDEDNESS: single stranded
        ( D ) TOPOLOGY: linear ( i i ) MOLECULE TYPE: genomic DNA ( v i ) ORIGINAL SOURCE:
        ( A ) ORGANISM: *Streptococcus suis* type II (pathogenic)

( i x ) FEATURE:
        ( D ) OTHER INFORMATION: Muramidase released protein (MRP) gene ( i x ) FEATURE:
        ( A ) NAME/KEY: promoter -35 region (B) LOCATION: bp 4 to 9

(ix) FEATURE:
(A) NAME/KEY: promoter -10 region
(B) LOCATION: bp 29 to 34

(ix) FEATURE:
(A) NAME/KEY: promoter -35 region
(B) LOCATION: bp 40 to 45

(ix) FEATURE:
(A) NAME/KEY: promoter -10 region
(B) LOCATION: bp 63 to 68

(ix) FEATURE:
(A) NAME/KEY: ribosome binding site
(B) LOCATION: bp 147 to 152

(ix) FEATURE:
(A) NAME/KEY: signal peptide
(B) LOCATION: bp 159 to 299

(ix) FEATURE:
(A) NAME/KEY: mature peptide
(B) LOCATION: bp 300 to 3926

(ix) FEATURE:
(A) NAME/KEY: proline rich region
(B) LOCATION: from bp 2757 to 3014

(ix) FEATURE:
(A) NAME/KEY: repetitive units
(B) LOCATION: from bp 3015 to 3176, 3423 to 3584 and 3585 to 3743

(ix) FEATURE:
(A) NAME/KEY: membrane anchor sequence
(B) LOCATION: from bp 3825 to 3926

(ix) FEATURE:
(A) NAME/KEY: dyad symmetry regions
(B) LOCATION: from bp 4069 to 4080 and from bp 4087 to 4098

(xi) SEQUENCE DESCRIPTION: SEQ ID NO:3:

```
GAATTCATAA TGTTTTTTTG AGGAATTTTA TAATATTACT TGGCATTTAA AGTTATTTGT        60

AGTATAATAC CTCGAATGAT TGCGGGAGTT TTCAAGGCTT TGATACAAAG AGTAGAAAAT       120

TTGTGTAATT AAATTAATAT TTATATGGGG GATTTTTT                               158
```

```
ATG  CGT  AGA  TCA  AAT  AAA  AAA  TCA  TTT  GAC  TGG  TAC  GGT  ACG  AAA  CAA    206
Met  Arg  Arg  Ser  Asn  Lys  Lys  Ser  Phe  Asp  Trp  Tyr  Gly  Thr  Lys  Gln
     -45            -40                      -35

CAA  TTT  TCG  ATT  CGT  AAG  TAT  CAT  TTT  GGG  GCA  GCA  AGC  GTT  TTG  CTT    254
Gln  Phe  Ser  Ile  Arg  Lys  Tyr  His  Phe  Gly  Ala  Ala  Ser  Val  Leu  Leu
     -30            -25                      -20

GGT  GTG  TCG  TTA  GTT  TTA  GGT  GCT  GGT  GCA  CAG  GTT  GTT  AAG  GCT  GAT    302
Gly  Val  Ser  Leu  Val  Leu  Gly  Ala  Gly  Ala  Gln  Val  Val  Lys  Ala  Asp
-15                 -10                       -5                          1

GAA  ACT  GTT  GCT  TCA  TCA  GAA  CCA  ACT  ATT  GCC  AGT  AGT  GTA  GCG  CCT    350
Glu  Thr  Val  Ala  Ser  Ser  Glu  Pro  Thr  Ile  Ala  Ser  Ser  Val  Ala  Pro
               5                        10                      15

GCT  TCA  ACA  GAA  GCG  GTT  GCA  GAA  GAA  GCA  GAA  AAA  ACA  AAT  GCT  GAA    398
Ala  Ser  Thr  Glu  Ala  Val  Ala  Glu  Glu  Ala  Glu  Lys  Thr  Asn  Ala  Glu
          20                      25                      30

AAT  ACG  AGT  GCA  GTA  GCT  ACG  ACT  TCA  ACA  GAA  GTT  GAA  AAA  GCG  AAA    446
Asn  Thr  Ser  Ala  Val  Ala  Thr  Thr  Ser  Thr  Glu  Val  Glu  Lys  Ala  Lys
     35                      40                      45

GCT  GTT  CTT  GAA  CAG  GTA  ACA  TCA  GAA  TCA  CCA  CTT  TTG  GCT  GGT  CTT    494
Ala  Val  Leu  Glu  Gln  Val  Thr  Ser  Glu  Ser  Pro  Leu  Leu  Ala  Gly  Leu
50                 55                      60                           65

GGT  CAA  AAA  GAG  TTG  GCT  AAA  ACT  GAA  GAT  GCA  ACT  CTT  GCA  AAA  GCT    542
```

| | | | | | | | | | | | | | | | | |
|---|---|---|---|---|---|---|---|---|---|---|---|---|---|---|---|---|
| Gly | Gln | Lys | Glu | Leu 70 | Ala | Lys | Thr | Glu 75 | Asp | Ala | Thr | Leu | Ala 80 | Lys | Ala | |
| ATA | GAG | GAT | GCT | CAA | ACA | AAA | CTT | GCA | GCA | GCT | AAG | GCA | ATT | TTG | GCT | 590 |
| Ile | Glu | Asp | Ala 85 | Gln | Thr | Lys | Leu | Ala 90 | Ala | Ala | Lys | Ala | Ile 95 | Leu | Ala | |
| GAC | TCA | GAA | GCA | ACT | GTT | GAG | CAA | GTT | GAA | GCG | CAA | GTC | GCA | GCG | GTT | 638 |
| Asp | Ser | Glu 100 | Ala | Thr | Val | Glu | Gln 105 | Val | Glu | Ala | Gln | Val 110 | Ala | Ala | Val | |
| AAA | GTA | GCC | AAC | GAG | GCG | CTA | GGG | AAT | GAA | TTG | CAA | AAA | TAC | ACT | GTA | 686 |
| Lys | Val 115 | Ala | Asn | Glu | Ala 120 | Leu | Gly | Asn | Glu | Leu 125 | Gln | Lys | Tyr | Thr | Val | |
| GAT | GGT | CTC | TTG | ACA | GCG | GCT | CTT | GAT | ACA | GTA | GCA | CCT | GAT | ACA | ACT | 734 |
| Asp 130 | Gly | Leu | Leu | Thr | Ala 135 | Ala | Leu | Asp | Thr | Val 140 | Ala | Pro | Asp | Thr | Thr 145 | |
| GCA | TCA | ACA | TTG | AAA | GTT | GGT | GAT | GGC | GAA | GGT | ACC | CTT | CTA | GAT | AGC | 782 |
| Ala | Ser | Thr | Leu | Lys 150 | Val | Gly | Asp | Gly | Glu 155 | Gly | Thr | Leu | Leu | Asp 160 | Ser | |
| ACT | ACA | ACA | GCA | ACG | CCT | TCA | ATG | GCT | GAG | CCA | AAT | GGT | GCA | GCA | ATT | 830 |
| Thr | Thr | Thr | Ala | Thr 165 | Pro | Ser | Met | Ala | Glu 170 | Pro | Asn | Gly | Ala | Ala 175 | Ile | |
| GCT | CCA | CAT | ACA | CTT | CGA | ACT | CAA | GAT | GGA | ATT | AAA | GCG | ACA | TCA | GAG | 878 |
| Ala | Pro | His | Thr 180 | Leu | Arg | Thr | Gln | Asp 185 | Gly | Ile | Lys | Ala | Thr 190 | Ser | Glu | |
| CCA | AAT | TGG | TAT | ACT | TTT | GAA | TCG | TAC | GAT | TTG | TAC | TCA | TAT | AAT | AAA | 926 |
| Pro | Asn | Trp 195 | Tyr | Thr | Phe | Glu | Ser 200 | Tyr | Asp | Leu | Tyr | Ser 205 | Tyr | Asn | Lys | |
| AAT | ATG | GCT | AGC | TCA | ACT | TAT | AAA | GGA | GCT | GAA | GTT | GAT | GCC | TAC | ATT | 974 |
| Asn 210 | Met | Ala | Ser | Ser | Thr 215 | Tyr | Lys | Gly | Ala | Glu 220 | Val | Asp | Ala | Tyr | Ile 225 | |
| CGT | TAC | TCT | TTG | GAT | AAT | GAT | TCG | TCA | ACA | ACT | GCT | GTT | TTA | GCA | GAG | 1022 |
| Arg | Tyr | Ser | Leu | Asp 230 | Asn | Asp | Ser | Ser | Thr 235 | Thr | Ala | Val | Leu | Ala 240 | Glu | |
| TTG | GTA | AGT | AGG | ACA | ACT | GGT | GAT | GTG | TTA | GAG | AAA | TAT | ACG | ATT | GAA | 1070 |
| Leu | Val | Ser | Arg 245 | Thr | Thr | Gly | Asp | Val 250 | Leu | Glu | Lys | Tyr | Thr 255 | Ile | Glu | |
| CCG | GGC | GAG | AGT | GTT | ACG | TTT | TCA | CAT | CCG | ACA | AAA | GTT | AAT | GCT | AAT | 1118 |
| Pro | Gly | Glu | Ser 260 | Val | Thr | Phe | Ser | His 265 | Pro | Thr | Lys | Val | Asn 270 | Ala | Asn | |
| AAT | AGC | AAT | ATA | ACT | GTG | ACT | TAT | GAT | ACC | TCA | TTA | GCT | TCT | GCT | AAT | 1166 |
| Asn | Ser | Asn 275 | Ile | Thr | Val | Thr | Tyr 280 | Asp | Thr | Ser | Leu | Ala 285 | Ser | Ala | Asn | |
| ACT | CCT | GGA | GCA | TTG | AAA | TTC | TCT | GCT | AAT | GAT | GAT | GTT | TAT | TCA | ACA | 1214 |
| Thr | Pro 290 | Gly | Ala | Leu | Lys 295 | Phe | Ser | Ala | Asn | Asp 300 | Asp | Val | Tyr | Ser | Thr 305 | |
| ATT | ATT | GTA | CCT | GCT | TAT | CAG | ATT | AAT | ACA | ACT | CGT | TAC | GTC | ACT | GAA | 1262 |
| Ile | Ile | Val | Pro | Ala 310 | Tyr | Gln | Ile | Asn | Thr 315 | Thr | Arg | Tyr | Val | Thr 320 | Glu | |
| AGT | GGC | AAA | GTT | TTG | GCA | ACC | TAT | GGT | CTT | CAA | ACT | ATT | GCA | GGA | CAG | 1310 |
| Ser | Gly | Lys | Val 325 | Leu | Ala | Thr | Tyr | Gly 330 | Leu | Gln | Thr | Ile | Ala 335 | Gly | Gln | |
| GTA | GTT | ACT | CCA | TCT | TCT | GTT | CGT | GTA | TTT | ACT | GGG | TAT | GAT | TAT | GTG | 1358 |
| Val | Val | Thr 340 | Pro | Ser | Ser | Val | Arg 345 | Val | Phe | Thr | Gly | Tyr 350 | Asp | Tyr | Val | |
| GCA | ACT | ACA | ACT | AAA | GCC | GTT | CAA | GGT | CCA | TAT | CCA | AAG | GGA | ACG | GTA | 1406 |
| Ala | Thr | Thr | Thr 355 | Lys | Ala | Val | Gln | Gly 360 | Pro | Tyr | Pro | Lys | Gly 365 | Thr | Val | |
| TAC | CTT | GCT | GGT | ACG | GTT | CAA | AAG | GAT | ACA | GTA | CAA | TAT | AAA | GTT | ATT | 1454 |
| Tyr 370 | Leu | Ala | Gly | Thr | Val 375 | Gln | Lys | Asp | Thr | Val 380 | Gln | Tyr | Lys | Val | Ile 385 | |
| CGT | GAA | ATT | GTG | GAG | AAC | GAC | CAA | GCA | GTT | CTT | AAA | TTC | TAT | TAT | TTA | 1502 |

|  |  |  |  |  |  |  |  |  |  |  |  |  |  |  |  |
|---|---|---|---|---|---|---|---|---|---|---|---|---|---|---|---|
| Arg | Glu | Ile | Val | Glu<br>390 | Asn | Asp | Gln | Ala | Val<br>395 | Leu | Lys | Phe | Tyr | Tyr<br>400 | Leu |

| GAT | CCT | ACC | TAT | AAG | GGT | GAA | GTA | GAT | TGG | AGA | GGA | ACT | GAT | ACG | ACT | 1550 |
|---|---|---|---|---|---|---|---|---|---|---|---|---|---|---|---|---|
| Asp | Pro | Thr | Tyr<br>405 | Lys | Gly | Glu | Val | Asp<br>410 | Trp | Arg | Gly | Thr | Asp<br>415 | Thr | Thr | |

| GGG | TTT | ATT | GAG | TTG | CTT | ACA | ACT | TCC | CCA | ACA | ACC | TAT | AAA | GTT | GGT | 1598 |
|---|---|---|---|---|---|---|---|---|---|---|---|---|---|---|---|---|
| Gly | Phe | Ile<br>420 | Glu | Leu | Leu | Thr | Thr<br>425 | Ser | Pro | Thr | Thr | Tyr<br>430 | Lys | Val | Gly | |

| ACT | ATA | TAC | GAT | TAC | AAT | ATT | AAT | TCA | AAA | ATT | ACA | GCT | CCA | TTT | ACT | 1646 |
|---|---|---|---|---|---|---|---|---|---|---|---|---|---|---|---|---|
| Thr | Ile<br>435 | Tyr | Asp | Tyr | Asn | Ile<br>440 | Asn | Ser | Lys | Ile | Thr<br>445 | Ala | Pro | Phe | Thr | |

| ATT | GAT | CCT | ACC | AAG | AAT | GTT | ATG | GTT | TTC | AAG | GAA | AGT | GAA | CAG | AAC | 1694 |
|---|---|---|---|---|---|---|---|---|---|---|---|---|---|---|---|---|
| Ile<br>450 | Asp | Pro | Thr | Lys | Asn<br>455 | Val | Met | Val | Phe | Lys<br>460 | Glu | Ser | Glu | Gln | Asn<br>465 | |

| GAG | CAA | GGT | AGC | AAA | TAT | CGC | GTC | ATT | GCT | CAA | TGG | TCA | GGA | GAT | GAA | 1742 |
|---|---|---|---|---|---|---|---|---|---|---|---|---|---|---|---|---|
| Glu | Gln | Gly | Ser | Lys<br>470 | Tyr | Arg | Val | Ile | Ala<br>475 | Gln | Trp | Ser | Gly | Asp<br>480 | Glu | |

| ACC | ACT | AAA | GGT | ATA | TAT | GGA | AAA | ATC | TAT | ATC | GCT | ACT | CAG | GTT | TGG | 1790 |
|---|---|---|---|---|---|---|---|---|---|---|---|---|---|---|---|---|
| Thr | Thr | Lys | Gly<br>485 | Ile | Tyr | Gly | Lys | Ile<br>490 | Tyr | Ile | Ala | Thr | Gln<br>495 | Val | Trp | |

| ACG | ACT | AAA | TTG | GGA | ACA | AAC | GAG | TGG | GGA | TGG | TTT | GAC | TAT | TCT | GAT | 1838 |
|---|---|---|---|---|---|---|---|---|---|---|---|---|---|---|---|---|
| Thr | Thr | Lys<br>500 | Leu | Gly | Thr | Asn | Glu<br>505 | Trp | Gly | Trp | Phe | Asp<br>510 | Tyr | Ser | Asp | |

| GAC | CAA | GCT | GGT | ATA | AAA | TTT | AAT | AAC | AAA | GGT | TTT | TGG | CCG | GCA | GGT | 1886 |
|---|---|---|---|---|---|---|---|---|---|---|---|---|---|---|---|---|
| Asp | Gln | Ala | Gly<br>515 | Ile | Lys | Phe | Asn | Asn<br>520 | Lys | Gly | Phe | Trp | Pro<br>525 | Ala | Gly | |

| GTT | CAA | AAT | ACA | CTT | CGA | AAT | GCT | ACT | CCA | GCT | ACA | GCT | GTA | GAG | ACT | 1934 |
|---|---|---|---|---|---|---|---|---|---|---|---|---|---|---|---|---|
| Val<br>530 | Gln | Asn | Thr | Leu | Arg<br>535 | Asn | Ala | Thr | Pro | Ala<br>540 | Thr | Ala | Val | Glu | Thr<br>545 | |

| ACT | TAT | ATC | TAC | AAA | GAA | AGT | TCC | AAG | TAT | GGT | GAT | GTC | ATT | GTT | GAG | 1982 |
|---|---|---|---|---|---|---|---|---|---|---|---|---|---|---|---|---|
| Thr | Tyr | Ile | Tyr | Lys<br>550 | Glu | Ser | Ser | Lys | Tyr<br>555 | Gly | Asp | Val | Ile | Val<br>560 | Glu | |

| TAC | TAC | GAT | ACT | GAC | GGA | AAA | CAA | ATT | GTA | AAT | TCA | GTT | GTA | GAT | ACT | 2030 |
|---|---|---|---|---|---|---|---|---|---|---|---|---|---|---|---|---|
| Tyr | Tyr | Asp | Thr<br>565 | Asp | Gly | Lys | Gln | Ile<br>570 | Val | Asn | Ser | Val | Val<br>575 | Asp | Thr | |

| CCT | AAG | TCA | GCT | CTT | GGC | ACA | GAG | TAT | AAT | ACA | GAT | GTG | GAC | CGT | AGA | 2078 |
|---|---|---|---|---|---|---|---|---|---|---|---|---|---|---|---|---|
| Pro | Lys | Ser | Ala<br>580 | Leu | Gly | Thr | Glu | Tyr<br>585 | Asn | Thr | Asp | Val | Asp<br>590 | Arg | Arg | |

| CCA | GCC | AGC | TTG | GTT | GCT | GCT | GAT | GGG | ACA | GTC | TAC | TTC | TAC | AAA | GAA | 2126 |
|---|---|---|---|---|---|---|---|---|---|---|---|---|---|---|---|---|
| Pro | Ala | Ser<br>595 | Leu | Val | Ala | Ala | Asp<br>600 | Gly | Thr | Val | Tyr | Phe<br>605 | Tyr | Lys | Glu | |

| GTT | AAG | TCT | GAT | TCA | GCT | AAG | ACA | ACC | GGT | ACA | GTA | GTT | GCA | GGT | ACG | 2174 |
|---|---|---|---|---|---|---|---|---|---|---|---|---|---|---|---|---|
| Val<br>610 | Lys | Ser | Asp | Ser | Ala<br>615 | Lys | Thr | Thr | Gly | Thr<br>620 | Val | Val | Ala | Gly | Thr<br>625 | |

| ACA | ACT | GTT | AAG | TAT | GTT | TAC | GAA | AAA | GCT | GGT | AGC | GTT | AAT | GTT | AAC | 2222 |
|---|---|---|---|---|---|---|---|---|---|---|---|---|---|---|---|---|
| Thr | Thr | Val | Lys | Tyr<br>630 | Val | Tyr | Glu | Lys | Ala<br>635 | Gly | Ser | Val | Asn | Val<br>640 | Asn | |

| TTC | GTT | GAC | ATC | AAT | GGT | AAA | GTA | ATC | AAA | GCT | CCT | GTT | TCA | GAT | GAA | 2270 |
|---|---|---|---|---|---|---|---|---|---|---|---|---|---|---|---|---|
| Phe | Val | Asp | Ile<br>645 | Asn | Gly | Lys | Val | Ile<br>650 | Lys | Ala | Pro | Val | Ser<br>655 | Asp | Glu | |

| AAA | GAT | GCG | AAA | CCT | GGT | TAC | AAT | TAT | GAT | ACC | GAC | TTG | GAT | CAG | AAA | 2318 |
|---|---|---|---|---|---|---|---|---|---|---|---|---|---|---|---|---|
| Lys | Asp | Ala | Lys<br>660 | Pro | Gly | Tyr | Asn | Tyr<br>665 | Asp | Thr | Asp | Leu | Asp<br>670 | Gln | Lys | |

| TTA | GCT | TCC | ATC | ACT | TTT | GAA | GGC | AAG | GAA | TAC | AAA | CTT | GTT | CCT | GCT | 2366 |
|---|---|---|---|---|---|---|---|---|---|---|---|---|---|---|---|---|
| Leu | Ala | Ser<br>675 | Ile | Thr | Phe | Glu | Gly<br>680 | Lys | Glu | Tyr | Lys | Leu<br>685 | Val | Pro | Ala | |

| GGT | GAT | TAT | CCG | GTT | GGT | AAA | GTT | GGC | AAG | GGA | AAT | AAC | TTG | ATT | GAA | 2414 |
|---|---|---|---|---|---|---|---|---|---|---|---|---|---|---|---|---|
| Gly<br>690 | Asp | Tyr | Pro | Val | Gly<br>695 | Lys | Val | Gly | Lys | Gly<br>700 | Asn | Asn | Leu | Ile | Glu<br>705 | |

| GTT | GGT | AAT | AAT | ACT | GCG | AAA | GGT | ATT | GAC | CCA | ACA | ACA | GGC | AAA | ATT | 2462 |

```
Val Gly Asn Asn Thr Ala Lys Gly Ile Asp Pro Thr Thr Gly Lys Ile
            710                 715                 720

GAA GCC GGT GTT AAC AAA GAA GTT ACC TAT GTC TAT AGA GCA GTG ACA    2510
Glu Ala Gly Val Asn Lys Glu Val Thr Tyr Val Tyr Arg Ala Val Thr
            725                 730                 735

GGT TCT GTA GTT GTA AAT TAC AAA GAT ACA GAA GGT AAT GTG ATT AAA    2558
Gly Ser Val Val Val Asn Tyr Lys Asp Thr Glu Gly Asn Val Ile Lys
            740                 745                 750

GAT CCA GAA ACG GAT GTG TCT GAT GCA CCG GTT GGA GAT GCT TAT ACT    2606
Asp Pro Glu Thr Asp Val Ser Asp Ala Pro Val Gly Asp Ala Tyr Thr
            755                 760                 765

ACA ACT GAC AAG AAA CCA AAC GAA ATC ATC ACA AAA GAT GGA TCA CGC    2654
Thr Thr Asp Lys Lys Pro Asn Glu Ile Ile Thr Lys Asp Gly Ser Arg
770             775                 780                 785

TAT GTT CTT GTT CCA TCT AAG ACA GAT GGT GAG GAA AAT GGT AAA GTT    2702
Tyr Val Leu Val Pro Ser Lys Thr Asp Gly Glu Glu Asn Gly Lys Val
                790                 795                 800

ATC GAA GGA ACA ATC ACA GTA ACT TAT GTT TAC CAG AAA GTT GCA AAC    2750
Ile Glu Gly Thr Ile Thr Val Thr Tyr Val Tyr Gln Lys Val Ala Asn
            805                 810                 815

TGG ATT CCA GAG ATT CCA AAT GTA CCA GAA ACA GAC CGT CCA AAA GTA    2798
Trp Ile Pro Glu Ile Pro Asn Val Pro Glu Thr Asp Arg Pro Lys Val
        820                 825                 830

CCT TAC CCA TTT GAC CCA ACA GAG CCA GAC GAG CCA ATC GAT CCA ACG    2846
Pro Tyr Pro Phe Asp Pro Thr Glu Pro Asp Glu Pro Ile Asp Pro Thr
        835                 840                 845

ACA CCA GGA ACA AAT GGC GAG GTT CCA AAT ATT CCT TAC GTT CCA GGA    2894
Thr Pro Gly Thr Asn Gly Glu Val Pro Asn Ile Pro Tyr Val Pro Gly
850             855                 860                 865

TAT ACA CCG GTT GAT CCT AAG GAT AAC ACG CCG TTG AAA CCA ATT GAT    2942
Tyr Thr Pro Val Asp Pro Lys Asp Asn Thr Pro Leu Lys Pro Ile Asp
                870                 875                 880

CCA AAT GAT CCA GGT AAG GGT TAT GTA CCA CCA ACA CCA GAA AAT CCA    2990
Pro Asn Asp Pro Gly Lys Gly Tyr Val Pro Pro Thr Pro Glu Asn Pro
            885                 890                 895

GGT GTT GAT ACA CCA ATT CCT TAT GTT CCA GTT AAA AAA GTC GTA ACT    3038
Gly Val Asp Thr Pro Ile Pro Tyr Val Pro Val Lys Lys Val Val Thr
        900                 905                 910

AAC CAC GTT GAT GAA GAG GGT AAC CCT ATT GCA CCG CAA GAA GAG GGA    3086
Asn His Val Asp Glu Glu Gly Asn Pro Ile Ala Pro Gln Glu Glu Gly
        915                 920                 925

ACA AAA CCA AAC AAA TCA ATC CCA GGT TAC GAG TTC ACA GGT AAA ACT    3134
Thr Lys Pro Asn Lys Ser Ile Pro Gly Tyr Glu Phe Thr Gly Lys Thr
930             935                 940                 945

GTT ACT GAC GAA GAT GGC AAC ACA ACT CAC ATC TAC AAG AAA ACA CCA    3182
Val Thr Asp Glu Asp Gly Asn Thr Thr His Ile Tyr Lys Lys Thr Pro
                950                 955                 960

GAA GTT AAG AAT GGT ACA GTT GTT GTT AAC TAT GTA ACA GAA GAT GGC    3230
Glu Val Lys Asn Gly Thr Val Val Val Asn Tyr Val Thr Glu Asp Gly
            965                 970                 975

ACA GTT ATC AAG GAA CCT GTA ACA GAT ACA CCA ACT TCT CCA GAA GGC    3278
Thr Val Ile Lys Glu Pro Val Thr Asp Thr Pro Thr Ser Pro Glu Gly
        980                 985                 990

ACA CCA TAC GAC ACT ACA GAC AAC AAA CCT AAG ACA ATC ACT TTC AAA    3326
Thr Pro Tyr Asp Thr Thr Asp Asn Lys Pro Lys Thr Ile Thr Phe Lys
        995                 1000                1005

GGT GAA GAG TAT GAA TTG GTT CGT GTT GAC GGT ACA GAA AAC GGT AAA    3374
Gly Glu Glu Tyr Glu Leu Val Arg Val Asp Gly Thr Glu Asn Gly Lys
1010            1015               1020                1025

GTT GTA GAA GGT GAA ACA GTT GTG ACT TAC GTT TAC CGT AAA GTC GAA    3422
```

| | | | | | | | | | | | | | | |
|---|---|---|---|---|---|---|---|---|---|---|---|---|---|---|
| Val | Val | Glu | Gly | Glu | Thr | Val | Val | Thr | Tyr | Val | Tyr | Arg | Lys | Val | Glu |
| | | | | 1030 | | | | | 1035 | | | | | 1040 | |

| ACA | CCT | GCT | AAG | AAA | GTT | GTA | ACT | AAC | CAC | GTT | GAT | GAA | GAG | GGT | AAC | 3470 |
|---|---|---|---|---|---|---|---|---|---|---|---|---|---|---|---|---|
| Thr | Pro | Ala | Lys | Lys | Val | Val | Thr | Asn | His | Val | Asp | Glu | Glu | Gly | Asn | |
| | | | 1045 | | | | | 1050 | | | | | 1055 | | | |

| CCT | GTT | GCG | CCG | CAA | GAA | GAG | GGA | ACA | AAA | CCA | AAC | AAA | TCA | ATC | CCA | 3518 |
|---|---|---|---|---|---|---|---|---|---|---|---|---|---|---|---|---|
| Pro | Val | Ala | Pro | Gln | Glu | Glu | Gly | Thr | Lys | Pro | Asn | Lys | Ser | Ile | Pro | |
| | | 1060 | | | | | 1065 | | | | | 1070 | | | | |

| GGT | TAC | GAA | TTT | ACA | GGT | AAA | ACT | GTT | ACT | GAC | GAA | GAT | GGC | AAC | ACA | 3566 |
|---|---|---|---|---|---|---|---|---|---|---|---|---|---|---|---|---|
| Gly | Tyr | Glu | Phe | Thr | Gly | Lys | Thr | Val | Thr | Asp | Glu | Asp | Gly | Asn | Thr | |
| | 1075 | | | | | 1080 | | | | | 1085 | | | | | |

| ACT | CAC | ATC | TAC | AAG | AAA | ACA | CCT | GCT | AAG | AAA | GTT | GTG | ACT | AAC | CAC | 3614 |
|---|---|---|---|---|---|---|---|---|---|---|---|---|---|---|---|---|
| Thr | His | Ile | Tyr | Lys | Lys | Thr | Pro | Ala | Lys | Lys | Val | Val | Thr | Asn | His | |
| 1090 | | | | | 1095 | | | | | 1100 | | | | | 1105 | |

| GTT | GAT | GAA | GAA | GGT | AAC | CCT | ATT | GCT | CCA | CAA | GAG | GAT | GGG | ACA | ACA | 3662 |
|---|---|---|---|---|---|---|---|---|---|---|---|---|---|---|---|---|
| Val | Asp | Glu | Glu | Gly | Asn | Pro | Ile | Ala | Pro | Gln | Glu | Asp | Gly | Thr | Thr | |
| | | | | 1110 | | | | | 1115 | | | | | 1120 | | |

| CCA | AAA | CGT | CAA | ATT | TCA | GGT | TAC | GAG | TAT | GTG | CGT | ACT | GTA | GTT | GAT | 3710 |
|---|---|---|---|---|---|---|---|---|---|---|---|---|---|---|---|---|
| Pro | Lys | Arg | Gln | Ile | Ser | Gly | Tyr | Glu | Tyr | Val | Arg | Thr | Val | Val | Asp | |
| | | | 1125 | | | | | 1130 | | | | | 1135 | | | |

| GAA | GAA | GGT | AAC | ACG | ACA | CAT | ATT | TAT | CGC | AAA | CTT | TCT | AAT | AAA | CCA | 3758 |
|---|---|---|---|---|---|---|---|---|---|---|---|---|---|---|---|---|
| Glu | Glu | Gly | Asn | Thr | Thr | His | Ile | Tyr | Arg | Lys | Leu | Ser | Asn | Lys | Pro | |
| | | 1140 | | | | | 1145 | | | | | 1150 | | | | |

| ACA | ACA | CCT | GAG | AAG | GAA | ACT | CCT | GCA | AAA | CCT | CAA | GCA | GGT | AAA | ACC | 3806 |
|---|---|---|---|---|---|---|---|---|---|---|---|---|---|---|---|---|
| Thr | Thr | Pro | Glu | Lys | Glu | Thr | Pro | Ala | Lys | Pro | Gln | Ala | Gly | Lys | Thr | |
| | 1155 | | | | | 1160 | | | | | 1165 | | | | | |

| GCT | TCA | GGT | AAA | GCT | CAA | TTG | CCA | AAT | ACT | GGT | GAG | GCT | TCA | TCT | GTG | 3854 |
|---|---|---|---|---|---|---|---|---|---|---|---|---|---|---|---|---|
| Ala | Ser | Gly | Lys | Ala | Gln | Leu | Pro | Asn | Thr | Gly | Glu | Ala | Ser | Ser | Val | |
| 1170 | | | | | 1175 | | | | | 1180 | | | | | 1185 | |

| GCA | GGT | GCG | CTT | GGT | ACA | GCA | ATG | CTT | GTC | GCA | ACA | CTT | GCG | TTT | GCA | 3902 |
|---|---|---|---|---|---|---|---|---|---|---|---|---|---|---|---|---|
| Ala | Gly | Ala | Leu | Gly | Thr | Ala | Met | Leu | Val | Ala | Thr | Leu | Ala | Phe | Ala | |
| | | | | 1190 | | | | | 1195 | | | | | 1200 | | |

| AGA | AAA | CGT | CGT | CGT | AAC | GAA | GAT | TAG | TCAAAATTCT | TTATACAGAC | 3949 |
|---|---|---|---|---|---|---|---|---|---|---|---|
| Arg | Lys | Arg | Arg | Arg | Asn | Glu | Asp | | | | |
| | | | 1205 | | | | | | | | |

| TTTATTCCCC | CACATAGAAA | GTATAAGAAT | TGTACGTAAC | ATGCAGGATT | GCCTTTCCGA | 4009 |
|---|---|---|---|---|---|---|
| AAAAATGAGG | CTGGGCAAAA | AGTCCAGAGT | TACATCTTAG | AGTTCGCTCC | ATTTCCAACC | 4069 |
| TCCAACAGTC | ACTACTCTGA | CTGTTGGAGC | TGTGTGGGGG | TGGAGACG | | 4118 |